(12) United States Patent
Sampson et al.

(10) Patent No.: US 8,759,619 B2
(45) Date of Patent: Jun. 24, 2014

(54) AXMI218, AXMI219, AXMI220, AXMI226, AXMI227, AXMI228, AXMI229, AXMI230, AND AXMI231, DELTA-ENDOTOXIN GENES AND METHODS FOR THEIR USE

(75) Inventors: Kimberly Sampson, Durham, NC (US); Daniel Tomso, Bahama, NC (US)

(73) Assignee: Athenix Corp., Morrisville, NC (US)

( * ) Notice: Subject to any disclaimer, the term of this patent is extended or adjusted under 35 U.S.C. 154(b) by 402 days.

(21) Appl. No.: 13/030,399

(22) Filed: Feb. 18, 2011

(65) Prior Publication Data

US 2011/0203014 A1 Aug. 18, 2011

Related U.S. Application Data

(60) Provisional application No. 61/305,808, filed on Feb. 18, 2010.

(51) Int. Cl.
*A01H 5/00* (2006.01)
*C12N 15/82* (2006.01)
*C12P 1/00* (2006.01)
*C07K 1/00* (2006.01)
*C07H 21/02* (2006.01)

(52) U.S. Cl.
USPC ............... 800/302; 435/320.1; 435/252.3; 435/419; 530/350; 536/23.71; 800/288

(58) Field of Classification Search
USPC .......................................... 800/302
See application file for complete search history.

(56) References Cited

U.S. PATENT DOCUMENTS

| 2004/0016020 | A1 | 1/2004 | Arnaut et al. |
| 2009/0100543 | A1 | 4/2009 | Carozzi et al. |
| 2010/0005543 | A1 | 1/2010 | Sampson et al. |
| 2010/0298207 | A1 | 11/2010 | Sampson et al. |

FOREIGN PATENT DOCUMENTS

| WO | 2006083891 | 8/2006 |
| WO | 2007147029 | 12/2007 |

OTHER PUBLICATIONS

Pardo Lopez et al, Strategies to Improve the Insecticidal Activity of Cry Toxins from *Bacillus thuringiensis*, Peptides (2009) 30:589-595.*
Aronson et al, Why *Bacillus thuringiensis* Insecticidal Toxins are so Effective: Unique Features of their Mode of Action, FEMS Microbiol. Lett. (2001) 195:1-8.*
Herrero et al, Mutations in the *Bacillus thuringiensis* Cry1Ca Toxin Demonstrate the Role of Domains II and III in Specificity Towards *Spodoptera exigua* Larvae, Biochem. J. (2004) 384:507-513.*
Abdul-Rauf et al, Mutations of Loop 2 and Loop 3 Residues in Domain II of *Bacillus thuringiensis* Cry1C delta-Endotoxin Affect Insecticidal Specificity and Inidial Binding to *Spodoptera littoralis* and *Aedes aegypti* Midgut Membranes, Curr. Microbiol. (1999) 39:94-98.*
De Maagd et al, How *Bacillus thuringiensis* has Evolved Specific Toxins to Colonize the Insect World, Trends Genet. (2001) 17:193-199.*
Sato, K et al., "Cloning and sequencing of the gene for a putatively nematode-toxic crystal protein, Cry21Ba1, from *Bacillus thuringiensis* serovar roskildiensis", Jpn. J. Nematol., vol. 34, p. 79-88, 2004, accession AB088406.1.
De Maagd, R. A. et al., "How *Bacillus thuringiensis* has evolved specific toxins to colonize the insect world", Trends in Genetics, vol. 17, No. 4, Apr. 1, 2001, p. 193-199.

* cited by examiner

*Primary Examiner* — David H Kruse
*Assistant Examiner* — Mykola Kovalenko

(57) ABSTRACT

Compositions and methods for conferring pesticidal activity to bacteria, plants, plant cells, tissues and seeds are provided. Compositions comprising a coding sequence for a toxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated toxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:13-30, or the nucleotide sequence set forth in SEQ ID NO:1-12, as well as variants and fragments thereof.

25 Claims, No Drawings

SEQUENCE LISTING

```
<160> NUMBER OF SEQ ID NOS: 37

<210> SEQ ID NO 1
<211> LENGTH: 3495
<212> TYPE: DNA
<213> ORGANISM: Bacillus thuringiensis

<400> SEQUENCE: 1
atgtctgaat atgaattaat agacgtatca cccaagcctt ataatgtttt aatgcagcgc      60
cccgatgagg ctggaggcat agattgggac gctgaaattt ctaaaatgat taaaacgtat     120
tatcaaaaag gtactttgc tgcggatttc gctacgatta ttcttccgct catattggct     180
cataatgtac agtggaatgt tgtactaaaa tctgtattaa gttttgctag cgctctacct     240
ggtattggca cagctgtttc tattttgtca ccgtttcttc aattgttatt tccgacagat     300
cctgcagcac atgacaaaca attaatgaaa ttaattttag accaaacaaa aatattaata     360
gatcaagctg tatcacaaga ggtaatgaac cgcatatctc aacaaattac aggattgtac     420
gcaaatttag cacgatttaa tcgaacaata gcagcgtatg aaacgttagc gcccacgact     480
atcattgcag agattcaggc tatagaggct gtatttgata atcaagttcc tcaacttgta     540
```

```
gatccaggat accttgctct aacattacct ctatacgttc aaggtataaa tctcaatctt    600
atgttttata aatcagtact agatcacgca gagcaattga aaataccggc gggggaacaa    660
aattattata aaacgtcatt gagagacaaa attaaaacag ccagtgcgca ggtatatact    720
tactttaaac aggtaccttg gcgtccaaat gaaattcgc cttcttctgc atctaaccag     780
gatattgtaa caagacaaac aatgtataca cattgtttag attacgtggc aatgtggcct    840
acttttaatc cggacctgta tccattatca gcagatatcg aacaaacgag agttctttct    900
tcaccgataa gcggactacc aggaaaacca ggtgcctacg gtccatttgt ggattttttg    960
ggattcgatg ataccttaga attaacaagc ataacctatt ggcaaggaga taggattgat    1020
cgtatagatc aaaatttttac atatggtcgc gttattcgtg gcggtagcgg tggtggcggt   1080
agccgacatg acatcccttc ttccagagcg aatcccattg catcactatg gatggattat   1140
aatagtaata attatcagtt tgtgtcctat cagatgtaca atacgctgat agattataca   1200
aaaccgcaaa caaatctact gctcgcacca cctaaccata aattacatcg gctatataca   1260
accgatgatc cttcattcgg aggacgtgtc ggtaccatag ggaatcaatt tatacaaaat   1320
actatatttc cagaaaacat aatggggact tttgatcaag attttagggggt tacacgaatt   1380 aaaggtattc catttgaaaa gagcccatcg acgacggcat tcacatacgc aaaagagcca   1440
ttaaatggcg cagaggccgt caagctaggt attcgtcaga cattagatct cccaattaca   1500
aacgtaacaa caggttggta ccaaattcga atccgatatg caagtacgga tttgacttct   1560
attgaattta aactagatgt tggcggacag agtctaatcg ataaaactgt agtgttacca   1620
gccactacaa caggtgatcc aactgggatt gaaggggcga atggaacgta tacgttactc   1680
accattcagg aaatatcgat tccagctgga aattttcatg tctatgtgac caataatttc   1740
ggtcccaatt tatttttaga tcggattgaa tttgttccta tgttaagctc agtagatatt   1800
gataaagatt ttaattttgg accaaaccca ggataccaac tggtttggga agatgataaa   1860
cgctatggga gaacggtaca tggaacaata gaatcagaag acggcgtact attgttcaca   1920
tctggtggca atgtggatat tcagcctggt acacagccta tagatcacga tttttgaagaa  1980 ccattcaatc aattatacgt tggcaaggtg ggcggtacaa aaggacatat aaaagctact   2040
atatatttgg ataatccaca aaaacaaggc atgttcacga ccgacgcaga tttagccaaa   2100
gtcacacaag tagtgaatgc tttatttata acagatacac aattagcacc aacggtaaca   2160
gattattgga ttgatcaagt ctatctaaaa gtgaaggctt tgtcggatga tctgtttgga   2220
gaagaaaaag aaaggttacg ccaacgtgta gctcgcgcta aacaaatcaa tactatgaaa   2280
aacaaattaa ttggtagttc attccaaaca ttgacgaatt ggcaacttag ctcggatgtc   2340
gcactcttag ctgacaatcc attattcgcg ggaacttatg tattactacc gccttccaca   2400
tatcctgata caagaccttc gtacgcgtat caaaaggtgg atgaaagtaa actgaaaccc   2460
tatacgcgct atatagtcag aggctttatt gggcaagcgc aagacttagc gctcctggtt   2520
tctcgatatg ggaaagaagt tgatacagct cttacggttc cgtatcaaga agcgttacca   2580
ttatcaccgg atagtacatc gaattgctgt ggaccagttg cttgtccgcc atgtgaagga   2640
catgagtatg atacacatct attttcatat acgattgatg taggagcttt acaatcagaa   2700
atcaatctgg gcattgaaat aggcttcaaa attactagcc caacagggtt tgcacacatt   2760
agcaaccttg aaattgtaga agaccgtcct ttaacagaag cggagacaat caaagtaaaa   2820
caacgcgaaa agaatggat gcgtctatct caaaaacaac aatcacaaat gcaagcacag   2880
tatgatcaaa cgatgcaata ctttgctaat ttatatacaa caccagacca aacagaactt   2940
```

-continued

```
caaaacaccg tacagtatac ggatattgca aaggttcaag ttgtaacatt cccatctcct   3000
atgcagtggt ttatcccgca attaccaaga tcatcgtctg caatggtaca ggagttaatc   3060
aatgcaaaag aaaaagcctt gcgattatat ccggccaatt tgacacaaaa tggagatttc   3120
gccacaggtt tatccaattg ggatgtgatt ccagatacga atgcaagtat agatactgta   3180
gatggcacat ctgttttacg tgtaccgtct tgggatgaaa ccgtatcgca aaccattaca   3240
ttaccaccgc atcaagaaga tgtcttatat caattacgcg taactgcaaa aggaaatggc   3300
agtgttggtc ttcagcataa tggcgaacaa gaaagactat attttaatca gaataatcca   3360
aatggaaata cctttgtaac aaaatcaact tcattttatc caacagcttc gactttatct   3420
atacaaattc aatctgaagg aacagatttt tatgtgaaaa cgatcgaagt gtttgtgcaa   3480
cccgtcccat tgaca                                                    3495
```

<210> SEQ ID NO 2
<211> LENGTH: 3729
<212> TYPE: DNA
<213> ORGANISM: Bacillus thuringiensis

<400> SEQUENCE: 2

```
atggaacaac atgcactggt accacagaat atgacaagca acacggggct cattccttat     60
aatgtatatg caacagcgcc atctaacttt gcttcattta cagatgtttt taatgattta    120
aaagaggctt atgatgagtt ttctaaaaca ggcgcaatag atgttttaaa acaacattta    180
aatgtagctt ggaacacata taaaaccaat tctgttgatt atttagcttt aataaaagcc    240
acaatctctt tacttggatt taccccagcg ggacctgcag tcccttttat taatatgttt    300
gtagatatgg tttttccaat gttatttggt ggttcagggg ctgataaaaa tacaatattc    360
ttcgagatga ttatggacca agttgaacag ttggtcgatc aaaaatttga agcgttcaca    420
ctgaataatt taaataacat tattgaggga atagaaacca atttagttga ttttcaaaat    480
gcaatccaaa tagcaatttg tcaaggagaa ggcccagggc ttcgatctga tccttgtaca    540
ccgagtatag accatttaca aaaggtatat acagcattta caacagctag atcacaaatt    600
caaactaatt tgccacattt caaaaatcca atggatttag ggaatacaaa tttccaaagt    660
gattttgtct tgttaacatt accactatac acaaatgtag caaatttaaa tttgttgtta    720
catcatggtt ttattcaatt tgccgaaaaa tggaaatctg tttattatga tgaaggaaca    780
atgaatcaag taaaagcaga tttacaacat cggattcaag aatattctac aactgtttta    840
aacacatata atcaatattt acctgctgtc ggttcaagta aaagtcaaac taatagacgt    900
attcgatata tacgtggtat gacaattggt gctcttgata ttgcatcttt atggccaaca    960
atggataatt tgtattaccc aatgcgtacg gatttagatc aaactcgttt aacttttatg   1020
gatgttgttg gtccaataga aggtcaggat tttactttga gttttccaaa tggagatatg   1080
gagagatatg gttattttgg cagagagtta acgaaaatag agccacatta tcgtaaagcc   1140
aaagctcata atacaggagc tcgcgagtat aacattacaa atgggatgcg taattctggt   1200
aaaaatgcac tgaatcaaga ctcaacagat acttggggac cgaacgatgt atcttatgct   1260 gatttttca acagctcagg ctatttacaa gtgtttgcac ccgtttcctt tgtcaatatg    1320
agctctggct caggcacgta ctatgattat aataaatttg cagcattggg tgtaaatggc   1380
aacatcgttt cccctcctta tgctgatagt cttggaaatc ctatatcttc taaaaacatt   1440
ccaattttag atcaaaaaat aaattatttg tatcctgtaa cagggtcagg gattgctgaa   1500
aaaatggggt ttttagcaag tattgttcaa gctgatttat atccggagaa cattattgga   1560
```

-continued

```
acaatagatc ctatagatgg atcgcaaagt ataaaaggta ttccgtttga caaatgtaca    1620
aatctccaga tttctcgttt aaaagaacca ttgaacggtg cgcctgccgt acaattaagt    1680
aatggatctt ctttaacgct ttccatcaca aatatggtat cccaaccgta tcaaattcga    1740
attcgatatg cgtgtccaac agatacaact attttttctga atgtagctac aggtggccat    1800
tctcctgttt atcaaagtat aacgttacca gcaacaaata gtggtactgg tcatacagtt    1860
ccaggaacga ataatggcat gttttataca gtatttccta cgaggactgg tacacccata    1920
acagcaacaa ttccatctgg aaacttcaat gtgtatgtga cacataatga tagtgctaat    1980
ttattattag atcgaattga atttattccg acagtgtcac caccaccgcc accaccatcg    2040
aatcaaatta taaagttttt agatttaacg ccacagcgtc cccaaaacat tggtcatat     2100 cctactggat gggctgatgc tgtagacata aatggtgttt ccaatggagc gttctcaatt    2160
caatatatca gtcgaggacg cgtaataaga aatgtcgaca aaactagtgg gccttttttca   2220 gacaaatatc cacccgcacc ggactcatgg tttaattttg atacaattca gtttgtagcc    2280
tattcaaatg tacattgcag tgtatcagga tctgtacaca tcatggaaac agtaaaaaat    2340
atatttgaaa cagaagaaga tttagccaaa gtaactgatg tagtgaacgc gttatttata    2400
acggatacac aattagcacc aaccgtgaca gattattgga ttgatcaagt ctatcttaaa    2460
gtcaatgcct tatctgatga atggtttgaa gaagaaaaaa cacaattacg tatcaaactg    2520
aatcgtgcga acaattacg tactatgcaa aatttactgg taggcggtga tttcacgaat     2580
cttatgcaat ggcgcatgag tccgtacacg acattacgta cagatagcga cttatttgtt    2640
gacaaatata tcttattaca accttcgatg gatccaataa caaaaccatc ctatgtgtat    2700
caaaaagtag aagaacagaa actaaaacca tatactcgct acactgttac aggttttctt    2760
gcacaagcgc aggactttac cttatggata tctcgctatg gaaacgaagt agaggaacaa    2820
attaaaattc cttatgaaga agcattacca ctttcacccg ataatgtgtc aaattgttgt    2880
ttacctgcga gtatctgttg cccagaacaa caaattaaac cacatgtgtt cacatatcac    2940
attgatgtag gtgaattaca attagaagct aatttaggca ttgaaatcgc aggtaaactt    3000
actacacgta gtggtttagc taaactaggt aatttagaaa ttgtcgaaga acgtcccctt    3060
acagtagatg aaatagccaa tgtacaacgt cgtgaaaaaa aatggaagcg tgcataccga    3120
acagagaaac aagaagcaca attagcatat caaaatatga aagaggtatt agcatctttc    3180
tatacaacac cggaacaaac acaattacga gacaatgtaa cgtatcaaga tatacaacag    3240
cttatcatgc cagcagaatt aataactatt catacgcgttta ttccgcaaat tctacaggat   3300
aatcagaatc tcgttatgca acttatggga gaaatggaac aggcacgtgc tctatatcca    3360
caaacacttt taataaatgg tgattttttcc atgggattac aaggatggga aggttcaggc    3420
gcaaccgtag atgtaagcca catgcaacca cagttagttt tatccaattg ggatgcaaga    3480
atgacacaaa cgattactgt atcacaagcc ccagttgata tagaaaaaac atatcaactg    3540
cgtgttacag cgtctggaaa aggaacggtt tctttatctg atcaagaaga tcaagtaaca    3600
ctcacgtttc atgaagattc ctttgtgaca aaacaaatag tcttgtattc caaccaagca    3660
ttattaaaat tagttgtaca atccgaagga agtcaattta ctatccaaac aattgaagtt    3720
tttgagata                                                           3729
```

<210> SEQ ID NO 3
<211> LENGTH: 3831
<212> TYPE: DNA
<213> ORGANISM: Bacillus thuringiensis

```
<400> SEQUENCE: 3
ttgaggagga gttgcatgga acaaaataat gtattatcgg aagaggggggc gcaatctatg      60 agtgtgtctt ctgtagagtc acctttgatt ccttataatg tatatgcgac agcaccgtca     120
ccattaccat ctaatttggc ttcatttaat gatattttta atgacctaaa agggcttat     180 gatgagtttt ctaaaacagg cgcaatagat gttttaaagc aacatttgaa tgtagcttgg     240
ggggcatata aaaacagcgc tgttgattat ttagctttaa taaaggcgac aatctcttta     300
cttggattta ccccagctgg acctgcggtt cctttttatta atatgtttgt ggatatgatt     360
tttccagttt tatttggtgg tacgactcaa gataaaaata agatattttt cgatatgatt     420
atggaacagg tcgaacagtt ggtcgatcag aaattccaaa atttcactat caataatttg     480
aataatatta ttgatggtat acaaaccgtt ttagttgatt ttcaaaatgc gattcaagta     540
gcgatttgtc agggagaaag cccagggctt cgatctgatc cttgtacacc gagtgcagca     600
catttagaac aggtgcatgt ggcatttaca acagcgagag ctaccataca aacgcagttg     660
ccacatttta aaacccaat ggatttaggg aatccaaact ttcaaagtga ttttgtcctg     720
ttaacgttac cactgtacac acatgcagcg aatttaaact tgttgttaca tcacggttat     780
attcaattta gagaaaaatg gaaatctgtt tcctatgatg aaggaacgat gaatcaaata     840
aaagcggatt tacagcatcg aattcaagaa tattctggaa ccgttttatc aacgtatacg     900
caatatttac cttctgtggg tgcgagtaaa tctcaaaccaa ataggcgtat tcgatatatt     960
cgtgggatga caataggcgc tcttgatatt gcggctttat ggccaacaat ggatgcggtt    1020
cactacccga ttcgaacgga cttagaccaa actcgtttag cattcttaga tgttgtgggg    1080
ccaatagaaa atcgggattt caacttaagt tttctaaatg gtgacatgga gggttacaat    1140
tatttcagca gagagttaac aaaaataacc ccgcattatc gtacggctaa aggcccaaat    1200
gtaggagatc gcaattatgg ccttacaaat gggatgcgta actacggtac agatgcgagt    1260
gaccaccaac agatagatac ttcgggaccg agtgatgaat atcacaataa ttttttacaac    1320 acagctggat atgcagaagt ggatgcaccg atttcctatg ttaatatgtg gagtgatgcg    1380
gccttatact atgattataa taaatttgga gcaactaatg ctaatggtga cgtagttgta    1440
cctcctaata ccgatgccat tggtaatcct gtatattcta aaaacatccc aattttaaat    1500
caaaaaataa attatatgta tcctgtaaca ggagccggta tttctgaaaa atgggattt    1560 ttagcgagtt tagtcccgta tgatctattt ccagaaaaacc tcattggcca gattgatcct    1620
atagatggat cgcagagtat aaaaggcatt ccttttgaaa aaagtacacc gctcacggtg    1680
cctcgtaaaa aggagcccat aaatggagca tctgcagtgc aacttcctaa gaatcaatac    1740
gtcaatatgg cccttacaaa tggtacttcc ggtgactatg aaatccgtat tcgatatgca    1800
agcgacacag ctgttacgat tactctcaac gtaacggctg gcagcaccac tatcatcaat    1860
aatcaagcca taacgttacc tgccacaaca ggcttgcaag ctagtgttcc aggtataaat    1920
ggatcctatg cacttaaccc aagcgattca tctctgaaaa cgcgcattcc agttggaaac    1980
tttcatgtct atgtgaccaa taatactggt gataatttgt ttttagatcg gattgaatt    2040 gctccgctag cttcgtcagg acctataata atacctaata cacctattaa aacttataca    2100
aatccaccaa atcctcaaca agtactttgg accgctcgtt caagtgtttt gggtgatata    2160
gtaaatttat ctggttatac taatggtgca aatggatatt ataccggtgt tatgcctgct    2220
attcgcattc aatttttccg aaacaatcaa ttagtggatc actatgatac ttccgaaggc    2280 agatacccctc ataatgctga ttttaatata tctaattata aaatcactgg tggatttgat    2340
```

```
aaaattgttt taattccact acatcaatat tacactgaac ctgtagaagg tcagataaat   2400
ggtacgataa caatgaatca aaacaaattc acaacagaag aagagttatc cgcagtcaca   2460
caagtagtga atgctttatt tataacagat acacaattgg cgccaacggt gaccgattat   2520
tggattgatc aagtctattt gaaagttaat gccttgtcag atgaatggtt tgaagaagaa   2580
aaagcgcagt tgcgtatgaa aatcaatcgt gccaaacagc ttcgtatgat gcaaaatcta   2640
ttagtgggtg gtgatttctc cactcttacg caatggcaaa agagtccgca tgcgagagtg   2700
gttgccaata gtgatctatt tgttgacaaa catttactgt tacaaccatc catgtaccct   2760
atgattgcac cgtcgtttgt gtatcaaaaa gtagaggaaa gaaaattaaa accatataca   2820
cgctataccg taaccggttt tgttgcccaa gcacagaaat tagagatttg ggtttctcgc   2880
tatggaaacg aagtgaagga acgaattgag attccatacg aagaaatgtt accactttca   2940
ccagacgctc aatcgaattg ttgtctacct gctcctgtct cttgcacagg acaacaaacg   3000
agtccacatg tatttacgta tcatattgat gtaggtgaat tgcaaccaga agcaaattta   3060
ggaattgaac ttgcatttaa actcactgct cgtagtggtg tagcgacaat cgggaatgta   3120
gaaatcgtag aagagcgtcc tttaacagcg gcggaaacac aaaaaataca gcagcgagaa   3180
agaaaatgga agcgtaccta tcaaaaaatg caccaagagg cacaaacgat gtatcaagaa   3240
actatggatg aattggcgtc gttatatacg acaccagaac aaacgcaatt acaggcaaac   3300
gtcacgtatc aggatattca aaatatcgag attccaatcg ctctgctagg cgctcatgcc   3360
tttatcccac aaatctcatc cgggtatgat gacttattcg cccaactgag tatcaaaaaa   3420
gacaatgcct tatatctata tccacagacg cttcttgtga acggtgattt ttctaggggg   3480
ttagcaggat ggaatggcac gggcgcgcaa gtcgctatga cagaggggca accgatgtta   3540
gtcttaacaa attgggatgc aaggctcacg caaagcatgt tgttaccaca aacagatagt   3600
ggaacagaga aagcctatca gctccgtgta acagcatctg gaaagggaac tgttgcttta   3660
tccgatacgg aaaatcaagt gaagctcact tttgatggag atacatttgt gacaaaaacaa   3720 atcattttgt atccagaaca ttcgatgtta gaattggccg tgcaatcgga tggcagtcaa   3780
tttataatcg aaagcattga agtatttgaa agccctattc ctttagtaga c            3831
```

<210> SEQ ID NO 4
<211> LENGTH: 3903
<212> TYPE: DNA
<213> ORGANISM: Bacillus thuringiensis

<400> SEQUENCE: 4

```
atgaatcaaa attacaataa caatgaatat gaaatcaagg atactgatac catgggctat     60
cagtcaaggt atccccttgc gaatacacca ggtgctgaat tacaacaaat gaattataaa    120
gattggatgg atagatgtac aaatggggaa tcaattgacg tattcggtga tacggcaggt    180
gctgttagga atacacttat tattggtacg ggtgtagcat gggcactcct tggtcttatt    240
ccagttgttg gtggtccagc atctgcaata gcgggactgt ttaatgtatt acttccatat    300
tggtggccag aacaagcagg ccctcctgga acccctcaag cacaatatac atggaagcag    360
ttgatggctg gtgcagaaga tattaccaat aaaaaaattc aagagagtgc aaaatcatac    420
gctactgcac aatggcaacg tgtacaaacc tatcaagcag actttaccca agcgcgctgt    480
gactggatac aagatcaaaa caatgaaata aagaaaagca gattacaaga tgcatttgat    540
gacttcaacg atgaattgca aggttcgatg ccattctttc gtgtgcaagg atttgaagtt    600
caaatgttat ccatgtatgc gcaagctgcg aatatgcact tgcttttgtt acgagatgtt    660
```

```
gtccaaaatg ggttgagttg gggatttctg caatccgaag ttgatcgcta ttatctcaat    720
ctcaatcccc aagggaatca ggggttacta caactattag gaacatacac aaactattgt    780
atagattggt ataataaagg tttacaggag caatatgcca ctggttactg gagtaaattc    840
aataatttcc gtataactat gactataacg gtacttgata ctgtatcagt atggccaaca    900
tttgatccaa aacactatgc gttacctaca aaatcacaac tgacacgaat ggtgtatacc    960
ccaaaagtag gagagacagc agcgtctttt aaaccatctc aacctatcaa tgtgatagaa   1020
aatagtatcg ttgctagtcc acgtttattt gcatggttaa ttgaagtgga atggttaat    1080 aaccaatata attatgtaca atattataaa caaactttcc aaaatacttt gcgtgacaca   1140
caatggtcga tatctaaggg aacaacttct ggaggtataa gtacaaatac ccttactatt   1200
ccatcaccac aatctcagga tgatgtttgg aaaattaaaa attactttag agacgatact   1260
ggtaatggtt cacatgatga taaaactgta acaggatgga cgtattcttt tacaaaatca   1320
cttgatcaaa cttttttttat tggtaacaga ggctactcta tcactcgatt gctcgggtta   1380
ccttgtagag gtaatgattc cggtatttgt gatccttgtg attttgagaa tccttgtgaa   1440
aatgaactcc ctaacacgac tatgccttgt gaggataaac aactatatag tcatcgactt   1500
tcatatttag gtgcgggtga acggaattat tacgatgccc ctcccgcatt aacctatttt   1560
ggttatggct ggacacacgt aagtgccgat gcacataact tggtagatgt taaaaagatt   1620
acccaaattc cagctgtcaa gggatcttcg ataagtggag atgccagagt cgtaaagggt   1680
tctggtagta caggaggaga tttaataaag ttgtctgcgg gtggtagcgt aactgtaaaa   1740
gtgacaatgc caataagtgt ttcaaaacaa acacaatggt atcagataag aatgcgttat   1800
gcaaatgacg aaactaattt attgaggtta gttgttaaaa gcgactttga agaatggtca   1860
agagtacagc aacttccagg tacctattta ggagaggagc taatattcca atcctttgca   1920
taccgaaatt tagtagacgg aatagctacc tatgaagaaa aatatattct tgaattaaca   1980
ttagagaatt taggaaaccc taatgatatt gatattaata ctaatctcct tatcgacaaa   2040
atcgaattca ttccaataga aggatccgtg ggagaatata aagcgaatca agctgtagaa   2100
gaagcacgga aggtagtgaa cgccttgttt acaggtgctg cgaaaaatgc tctgaagttg   2160
aatgtgacgg attatgctgt ggatcaagct tccaatcttg tcgagtgtgt gtcagatgaa   2220
ttccatgccc aagaaaaaat gatcctactg gatcaagtga aattcgccaa acgtctgagt   2280
caaacaagaa atctattaca ctatggagat tttgaatcct caaattggtc gggagagaat   2340
ggatggaaaa caagtcatca tgttcatgtt acggcgaata atccgatctt taaaggacgc   2400
tatctccaca tgccaggtgc gacaagctcc cagttctcta acactgtcta tccaacgtat   2460
atctatcaaa aagtggatga gtcaaaatta aaatcctata cccgttacct ggtacgcggg   2520
tttgtcggca atagtaagga cctagaatta ctggtggaac gatacggaaa agatgtacat   2580
gtagaaatgg atgtaccaaa tgacattcgg tattctttac caatgaatga atgtggtggc   2640
tttgatcgat gcaaatctgc atcggatcaa acaagaactc ctcacacatg cacatgtaaa   2700
gataccactt ccatgcatac ggattgtcaa tgtcaaaaca aagtgaatcg tacttcggca   2760
gacatgtata ccaatggatc gccaagtagt gtcatgtatg cggacggatt ccatgcccac   2820
aaatcctgtg gatgtaaaaa caacgacagg tatcaaaacg gaacacaccc acagaagtct   2880
tgtgaatgca agacccaca tgtcttctcg taccacattg acacaggatg tgtggaccag   2940
gaagaaaatc ttggtttgtg gttcgcgtta aagttgcaa cgaaaatgg tgtcgcaaac   3000 attgataact tagaaatcat cgaagcacaa ccactcacag gggaagcgtt agcccgcgtg   3060
```

```
aaaaaacgcg aacagaaatg gaaacaggaa atggcgcaaa aacgtttaca aacggacaaa    3120
gccgtacaag cagcgcaagg tgcgattcag cccctattca caaacgcgca gtacaatcgt    3180
ttacaatttg aaacattgtt cccgcaaatt gtcaatgcgg agatgttggt acaacagatt    3240
ccgtatatgt accatccatt cttgagcggg gcattgccaa ctgtaccagg tatgaatttt    3300
gaaatcattc aacgactatt ggcgttgacc ggaaatgccc gtggattata cgagcaacga    3360
aatctcgtgc gtaatggtac attcagctcc ggtacaggaa actggcacgt aacagaaggc    3420
gtaaaagtgc agccacttca aaatacatcc gtactcgttc tatcagagtg gaatcaggaa    3480
gcgtcccagc aattacacat tgatccagat cgcggatatg tattacgtgt cacagcgcga    3540
aaagaaggcg gaggaaaagg gactgtaaca atgagtgact gtgcagccta tacagagaca    3600
ttgaccttta catcatgtga ctttaacacg tttggttccc aaacgatgac aagtggtaca    3660
ttatctgggt ttgtgacgaa gacgttggag attttcccag atactgatcg tattcgaatt    3720
gatatggggg aaaccgaagg aacgtttcag attgaaagtg tggaactcat ttgtatggaa    3780
cagatggaag atgacttata tgatatggcg ggaaacttag aggaagagat gctggatcta    3840
gggatagaaa acatcaatgc agttacgaat aagatgtgct tctcatggga tattcagtgt    3900
cct                                                                  3903
```

<210> SEQ ID NO 5
<211> LENGTH: 3987
<212> TYPE: DNA
<213> ORGANISM: Bacillus thuringiensis

<400> SEQUENCE: 5

```
atggaaataa cttctgaaat ttatcctatt gcgtataatg ttttagcaaa tccacctact      60
ttagatacgg aagatcaaca aaatccttgg gatgcttatg taaattggag aaagcaacta     120
aatgatactt ggttaacata tgatcaaaac tttttaccag atcctgtaat ggcaattata     180
aatgatatgg caaatgcata tgcaggtaaa ccaggatctt atgttgcttt agcacaagaa     240
ggaattagaa ttgcattttt attttttacca ggaggtcaaa ctgcagcttt cgctataaat     300
aaagtaatag acttttttt ccctactcat cagccgtctt tatttgatca ataaaagat       360 cttgttgaac aaatgatcga tcaaaaattt gttgaacaag aaataaattc aaacataaat     420
caattaaatg gattaataac tcaattagga caatttagta attcaatgca acaagctatg     480
ggaaaaccaa tgaattttcc tgtaactcat tcatcttccg caacaactaa ttcatttgtt     540
gatacaaatg agttggatag ttacgattgt agtcaagatc ctgattgttc ttgttcagaa     600
gatcctaata gaacgagcaa ttcaccagtt tgtacacctt gtacttgtcg tattaaaggt     660
gtacaggatg aatttatagc tacaagaaaa gttatattag atattttaac cagtatgaaa     720
acttcattaa ctaatgtgtt aacaacagaa catgcaacaa cttatatgca aatatttta     780 cctatatata cgacagctgt aacactctat tttggtatgt ataaatctta tattgaattt     840
gcaacacaat atggttttga ataggtgtt aatggaaaca caatgaaata tgcaaatgaa     900
ttacaacaat atatttcagc agaatctgct tatgtttata atgaattcgc aatgtatttg     960
cctaattcta aaaatttaac aaaaggagat ttaaataaat atattcaata ttcaagaact    1020
ataactttaa acgctcttga tacattatct acgtggccat tatataatgt tttagattat    1080
cctatttcta caacattaaa tcagactaga cttgtattca atgatattat aagggcctgtt    1140 gagtgtagaa ctggtggaca gaatagtgat aattatcgt taatacgtt atatgattat    1200 agtggaaaca atcttcttaa taatgatatc actaattatt tctatgaaaa tacacaatta    1260
```

```
caaaatttat cttttcaaag atatacatct cctcaaggaa atatgatagc acaagatata    1320
attgttggag tttcagctaa ttattctaat ggagttaatt ttaaaaagac ggtatcttgg    1380
aatcctctta aaggatatac attaaaatgg gaaaataatg tattagaaga ctatccaact    1440
cttagtataa tgaacatgat atctgatcaa gattctagtg gatttgcagc tatagatatg    1500
tctgttcttt cttataatac tgctgttaaa gggacttgtg tatctcaaaa taatatagtt    1560
tttccgaatc agaaaattca atctatatct agtttaatcc caaataatac aaaaagttat    1620
tcatactatg gaaattcaga taaactaggt cttattacaa cacttatatc taatgatacg    1680
acttcatcga ttattttaag taatacaaca ggaattaata catttcctgc agaacaagca    1740
acaactacta caggaactaa attagtagaa tatgtgaatg gggcagctgc tcttcaactt    1800
aaacagaatg aatctgctgg atatattata gatactagtg caataccatc agggagatat    1860
aaagttcgtt ttagagcagc aatgaatggt ccgtataata ctgccatgtt atctttttaca   1920 attaataatt atgtagaaga taaactgta tctacggata caaaaccatt ggaaattatt     1980
gggaaacaag gcgcgtatat gctttcttct tctacatttt ttgaaatacc ttctacaaaa    2040
gcgttaccaa tgactatact gaattcgact tacaatgatg taattttaga tcgtattgaa    2100
tttattcctg cacctatgga agctattaaa aatcctattc ctattactta taatccaggt    2160
aatttatttt tcgaccctgg tgttaattat aatgatattt ggaataatcc agatcgtaaa    2220
attgcggata tagtcaattt atctggatct atcacttata gttatgccac agcccctact    2280
actaacgtaa gtacttcaat cgagttctta aaagttaatg cagttgttgc tacagtacct    2340
ttagaagaca gatcaggaac ttctggaagt tcaccagtac ctttgcctat caatattcaa    2400
aaaagtatca taggcggatt tgatcaaata cgtttaaaga ctacaactaa ttattttgt      2460 gaaggaactg caaatatatc aggaactgtc ggaaatcaaa attctgatcc taataacggt    2520
aataatggtt ctcctcctta ccatagttgt gagatggtta atggagagaa tctgtgtagt    2580
gggccaccta agttagaaca attaagtgat ttagaaaaaa taacatcttt tgtaacaaat    2640
ttatttgaat cttcaacata tatggaatta gcatcaaatg tttcaagtta taatattgat    2700
caagcagcaa tgaaagttga tgcattgtct tcttatatgt ttgctaaaga aaaagtatta    2760
ttacgtaaat tagtgaataa agcaaaggca ttaattcaaa aacgtaattt acttgtaaat    2820
ggagattttg gatcttataa gggatggtta tatggtacgc tagcaactat atctaatgat    2880
tcaccattat ttaaatgtaa ctatttatta ttagaacaac ttaatacacc agtatcatca    2940
tatgtttatc aaaaaataga agaatcacag ttaaaaccat atacgcgtta taagtttct     3000 ggttttatag cagaaagtaa agaattagaa cttgttgtat cccgatatga taaagaaatt    3060
tataagaaat taaatgtccc atatgcagat gcatttccta tttcttctga tcctactcca    3120
aattgttgtc aattaaattt atgttttaat gataattcag attctcattt ctttagctat    3180
agtattgatg ttggtgcact acatccaaaa tttaatccag gtattgaatt tggtctttgt    3240
gttgcagatg cgaatggtat tgcaaaagtg ggaaatttag aaattataga agaacgctca    3300
cttacagatc aagaaattca agttattcaa cagaaagaga aaaattggaa agttaaagta    3360
gatagagaat acaaagaaat cagttctgtt gtagaaccga tcatcaataa attgaattct    3420 tttttttaaaa atggagattg gaacgatgag gtttttatctc atgtgacata tcaagatgta   3480
tatagtattg ttttgccacg attatcaaaa tcagaacatt ggtttatgac aaatattcca    3540
gaagaagaag ctgttatttt acaagaaatg aagcaagcat taaaacgggt gttattctat    3600
ttagaagaga acaatcttgt acacaacggt aatttttatag atgattaaaa taattggatt   3660
```

-continued

```
gtagaaggta ctgttcaaat tataaatgga gataatggaa atttagcctt acaattttct   3720
tcgtggggag caactgtatc acaaactatt aatattttaa attttgatag agataaacaa   3780
tataaacttc gtttatatgg aaaaggaaaa ggtacggtta caattgaaca tggagaagaa   3840
atagaaaata taacatttga tacaaaccaa tttactacaa aagaacacat attttatttt   3900
gatgcatcat cttttatttt gagtattcaa tcagaatgtg atgtgtctat aatagatagt   3960
gttgaagtta cagaatattt agataaa                                       3987
```
<210> SEQ ID NO 6
<211> LENGTH: 3903
<212> TYPE: DNA
<213> ORGANISM: Bacillus thuringiensis

<400> SEQUENCE: 6
```
ttgcgtaatc taatcgatgt tccagttttt cttgaccaag ttataaagaa gatacgggga     60
ggtttataca tgaacataaa tgataacaag aatgaatatg aaatattgga tagtggaaat    120
ttgtcttatc agccaaggta tcctcttgcg cgagcaccag gttctgaatg ccaaaaacca    180
aatgccaaag atggaatata cacacctgtg ggcagagtgg atacagccct tcaaaatatc    240
gatatagggt tatctattcg tacagcgctt tctatcttac aaatgcttct atctgtaagt    300
tttccagcac taggaagagc cgctggacta ataaatatta tttttggatt tctgtgggga    360
acacttgctg gtcaatccgt ttgggaaaag tttatgagag cagtagaatc tcttgtaaat    420
caaaaaatta cagatgctgt cagagtgaaa gccctttcgg aattagaagg tgtacaaaat    480
gctttagaat tatatcaaga ggcagccgat gattggaatg aaaatccaac tgatgcatct    540
aataaagagc gtgttagaag acagtttaca tctacgaata caacaatcga gtatgctatg    600
ccatcatttc gagtcccaac ttttgaagta ccgttgttaa ctgtgtatgc acaagcggct    660
aatttacatt tacaattgtt acgggatgcc gttaagtttg gaaacgaatg gggtatgcct    720
tctgaggaag tagaggatat gtataataga ttaacaaggc gtacggcaga gtatacagat    780
cactgtgtag ctacctatga taaaggttta aaggaagctt atgacttagc accgaacccc    840
acagattaca ataaataccc ttatctcaat ccatactcta aagatccgat ttatggtaag    900
tattacacag ctccagttga ttggaatcta tttaatgact atcgaagaga tatgactctt    960
atggtgctag acattgtggc agtatggcca acctacaatc cgagaatcta tacaaaccca   1020
aatggcgtac aagtagaact ctcaagagaa gtatatagca cagtatatgg aagaggaggt   1080
agtaataatt catcttttga tgcaatcgaa tctcaaattg tcagaccacc tcatttagtg   1140
acagaactaa ccaatctaaa aattgagcag ggtgctactc tagatatgga acagatacaa   1200
tatcctaagt atatgaaggt tacgaatacg cttcattatg tagggagttc ttccacatgg   1260
gagcaaagct cttctgctat tcctattaga ccaattacgc agattcatac tatcccagcc   1320
aataatatag gtaatctttc cttatctcaa ttagatgtac cttaccgatt ttctttctat   1380
aacaaagatg atgctttgat tgctgcagtt ggagctgaat tccctccaaa cactgtaacc   1440
tggaacggga tacctaaagc cgaagatagt aatcaaaata gtcatcattt atcttatgtt   1500
ggtgccttag gtacacaatc ttcagctggg tttccttgga catatccgac ggagctttta   1560
ggagaatggg gatttggttg gttgcataac agtttaacac caactaacga gatactaagt   1620
gacaaaatca ctcaaattcc agcggtgaag gcattcaata tacaaggaaa cggaaaagta   1680
acaaaagggc ctggtagcac aggaggagac ttaatagcat tacctgcacc cagtggacaa   1740
attaacattt atctaaagga aacatcaaca aagaattatc gtgtgcgtct tcgatatgct   1800
```

```
gctactactg atggtcaatt acgagtagct cgagttcgaa atggtggagc tgttcgttgg    1860
tttgagaata taaatacgt tactactggt gcaagtgaaa actctttagc gtataatcag    1920
tttaaatatg tggatatttt cacatcagat ttcagtaata ttaatagctt ggtatttatt    1980
aaccaaagtg gtggcactat tcttattgac caaatcgaat tcattccaat tgaaggatcc    2040
ttagaagtct ttgaagcgga acaggattta gaaaatgcaa gaaaggccgt gaatgccttg    2100
tttacaggtg ctgcaaaaga tgtcctgaaa ttgaatgtga cggattatgc agtcgatcaa    2160
gcttccaatc ttgtcgaatg tgtatcggat gaattccatg cccaagaaaa aatgatccta    2220
ctggaccaag tcaagtttgc gaaacgtttg agtcaagcac gaaacctctt aaactatggg    2280
gattttgaat cttcagattg gtcaggagaa aatggatgga gaaccagtca tcacgtttct    2340
gtcagatcgg ataatccaac ctttaaaggg cactatctcc atatgccagg tgcgacaagt    2400
tcccagtttt ctaacaatgt ctatccaacg tatgtgtatc aaaaagtgga tgagtcaaaa    2460
ttaaaatcgt atacgata tctcgtacgc gggtttgtcg gcaatagtaa ggacctagaa    2520
ttactggtgg aacgatacgg aaaagatgta catgtagaaa tggatgtacc aaatgatatt    2580
cggtattctt taccaatgaa tgaatgtggt ggctttgatc gatgcaaatc tgcatcggat    2640
caaacaagac ctcctcatac atgcacatgt aaaaataccg ctgtagcgca tacagattgt    2700
cagtgtcaag ataagggaaa tcgtatttcg acgggcgtgt atacaaatgg accgacaggt    2760
agtgcagtgt atacaaatgg attccatacg caccaatcgt gtggctgtaa gaacaagaac    2820
agtgacaggt atcagagcgg aacacatcca cagaagtctt gtggatgcaa agacccacat    2880
gtcttctcgt accacattga cacagggtgt gtggaccagg aagaaaatct tggtttgtgg    2940
ttcgcgttaa aagttgcaag cgaaaatggt gtcgcaaaca ttgataactt agaaatcatc    3000
gaagcacaac cactcacagg ggaagcgtta gcccgcgtga aaaaacgcga acagaaatgg    3060
aaacaggaaa tggcgcaaaa acgtttacaa acgacaaag ccgtacaagc agcgcaaggt    3120
gcgattcagc ccctattcac aaacgcgcag tacaatcgtt tacaatttga acattgttc    3180
ccgcaaattg tcaatgcgga gatgttggta caacagattc cgtatatgta ccatccattc    3240
ttgagcgggg cattgccaac tgtaccaggt atgaattttg aaatcattca acgactattg    3300
gcggtgaccg gaaatgcccg tggattatac gagcaacgaa atctcgtgcg taatggtaca    3360
ttcagctccg gtacaggaag ctggcacgtg acagaaggga tagaggtgca gccacttcaa    3420
aacacatctg tgcttgttct atcagaatgg agtcatgaag cgtcccagca ggtacggatt    3480
gatccggatc gcggatatgt gttacgtgta acagcccgaa aagaaggtgc agggaaaggt    3540
actgtgacga tgagtgactg tgcagactat acagagacac tgacctttac atcttgtgac    3600
tacaatacgg tcggtaccca aacgatgaca ggtggtacat tatcgggatt tgtgaccaaa    3660
acgctggaaa tcttcccaga gacagatcgt attcgcattg acatcggaga aacagaaggt    3720
acgtttaaga ttgaaagtgt ggaactcatt tgtatggaac agatggaaga ccacttatat    3780
gatatggcag gaaacttaga ggaagagatg ctggatctgc agtcagctcg ttccggtagt    3840
ggtacgaaac ttataccacc attaacattt agtgattgct atacgaataa tgagtattgc    3900
tac                                                                 3903
```

<210> SEQ ID NO 7
<211> LENGTH: 3723
<212> TYPE: DNA
<213> ORGANISM: Bacillus thuringiensis

<400> SEQUENCE: 7

-continued

```
atggcgaatc aatatcaaaa tgaatttgaa atcttagatg cgaacccaag taaagatcca     60
attgccaatg gagcactacg atatccactc gcaacatcac cagaatctga actgcaaaac    120
atgaattata aagattggat ggatatgtgt gcagttggaa attctaccgg tgagagtcta    180
tcaacaaaag atgcggtcgt tacaagtatc aacatcacgt cctatcttct ttccgtcggc    240
ttcccagcag ctggagctgc ctttggaatc ctcggtgcac tgcttggttt tctttggcct    300
acgaatacgc aagagatatg gcaaaaattt atgaatgcgg ttgaggagct ggtggatcaa    360
aagattgaaa catttgcacg aaatcaagct atcgcaaggt tagccgggat acacggtgta    420
ttaaaggact accagggtgc agtgaatgat ttgaataagg atccaaacaa tcccttactg    480
caagaaatta ccagaacaca atttatagct gctgaaacgt ttattacagg ttctatgccc    540
ttgttccagg tcgtaggaca ggaagtaccc atgttaacaa tatttacaga agctgccaat    600
cttcatcttc ctctcctacg agatggggta acgtttggag caagttgggg tgtgccagta    660
gaaactagga atcgttatca attagagtta aagagaatc tctcgaaata cacagattat    720
tgtgtaaata tatataatat cggattacaa caagcacata aattaccacc gaattatgat    780
tacagatcgg ggaaaattcc atggatccca ccaaatcttt cgaatagttc atatagccgt    840
gaaatcccct attggaaccc tgtgatagat tggaacctct ataataatta tcgaagagac    900
atgacgttga tggtgttaga tgtagttgcg ctttggccga tgtataatcc caaactgtac    960
tcgaagcctg ttaaatcgga gcttacgcga gaattgtatt cagaacttat aggtcagaac   1020
aatatggagg atcagaacgc aatcgaaaat atgattgtcc gaccgccaca tttatttacc   1080
tggttggaca caatgaaatt tggttttcag agtcctaaac ctaatcctgg gaaccaaaga   1140
cagtatcggg atatacaagt cgtcttacac aagacgaacg acaacaactc atgggaggaa   1200
acaacggttt catgctatgg aacaagaact agcgaaactg ttcttaacaa tgctgcctac   1260
ggtcgcgtgg aattatccgg tgcttttttcg ccctgtatgt tacggtttta tacaccatat   1320 aatgggggg gatatttagt tggaaatgat gttccaaacg ttaccgctga cactccccat   1380
gctggtgggg ggaaccttgt aaattatgga acagctagat ggtacattgg aacagagata   1440
ccatacagca gtcttccaca taatcatcgt ttgtcttatg tggatggttg tagtacgtgg   1500
tttagttatc cgggcatagg caatacttt aactgggtaa gttcatttgt atttgcctgg   1560
acccataaca atgtagatcc aaacaacaca atagatccga ataagattac tcaaattcca   1620
gcggtgaaag gttatggatt aggagggaat gctacagtta ccgagggcc tggtagtaca   1680 ggggggatt tagttcaact acctaaccct ggatctgtaa agatacaact tcctgtcgca   1740
agtaagagtc aaagttaccg tgttagaatt cgttatgcga gtagtggaaa tgggacactg   1800
agggtagtta aatggaatca tggctactat tcacatgcat attataacgt ttctacaacc   1860
tattcaagtg cattaacata taattcattt aaatatttag aatcttacgc tataacaatg   1920
tatccagcag ataatgatct tgaaatctgg cttgaaaatt ctggtggtgg accaatcatc   1980
atcgacaaaa tcgaattcat tccaatccaa ggaactttgg cagaatatga agcggatcaa   2040
agtttagaaa aggcgagaaa ggcagtgaac gccttgttta cgaatgatgt gaaaaatgtc   2100
ctacagttga agatcacaga ttacgaagtg gatcaagctg ccaatcttgt ggagtgtgta   2160
tcagaggaat ccatgcaca agaaaaaatg atccttctgg atcaagtcaa gtttgcgaaa   2220
cgtctgagtc aatcgcgaaa tctattaaac tacggagatt ttgaatcgtc agattggtcg   2280
ggagagaatg gatggagaac cagttctcat gtccatgttg cggcggataa cccgatcttt   2340
aaaggacgat atcttcacat gccaggtgca atgagcccgc aattctctaa caatatctat   2400
```

```
ccaacgtatg cctaccaaaa agtggatgag tcaaaattaa aatcttatac tcgttacctt    2460
gtaaggggat ttgtagggaa tagtaaagac ctggaattat tagtagaacg atacggaaaa    2520
gaagtacatg tggaaatgga tgtacaaaat gatatccagt atacgttacc aatgaatgaa    2580
tgtggtggct ttgatcgatg caaaccagca tcctatcaag aaagacttcc tcatacatgc    2640
acatgtaaaa atgccgctgt agcgcataca gattgtcagt gtaaagataa ggtgaatcgt    2700
acttcggcag acgtttatac caacggattg acaagtcggg gcatgtatgc agatggattc    2760
ccttcgcaca gtcgtgtggg atgcaagaac cagaacagtg acatgtatca gaacggaaca    2820
cattcgcata gtcttgtggg atgcaaagac ccacatgtct tcacgtacca tattgacaca    2880
ggatgtgtgg atccagaaga aaacgtaggt ctattctttg ctttaaaaat tgcgagcgaa    2940
aatggtatcg ccaacattga taacttagaa atcattgaag cacagccact cacagggggaa    3000 gcgttagctc gtgtgaaaaa acgagaacag aaatggaaac acgaaatggc gcaaaaacgc    3060
ttgcaaacag agaaagccgt acaagcagcg aaaggtgcga ttcagaatct gtttacaaac    3120
gcgcagcaaa cccaactcaa acacaaaaca ttgtttcctg agattctaaa cgcagggaga    3180
ttggtccaac acattccata tgtgcatcac ccattcttga gcgggcact gccagccgta    3240 ccgggcatga atttcgatag gttccaacaa ttttccttct tggttgagac agcaagggga    3300
ttatatgagc aacgaaactt tgtatcaaac ggtacgttta gtgctggaat cgcaaattgg    3360
aatgcgacag atggtgtgac tgtacagcca gaggggccga catccgtact ggttttatcc    3420
aattggagtg acaaaacgtt ccaaaatctg cgcctcgatc cagaccgtgg gtatgtccta    3480
cgtgtgacgg caagaaaaga aggagcagga aaaggcactg tgacgataag tgactgtgcg    3540
gcgtctccag aaaccctcac ttttacctct tgtgacgaga atacaagtgg tacgtttgtg    3600
acaaaaacgc tggaaatctt cccagacaca gatcgcatcc gtattgacat cggtgaaaca    3660
gaaggaacgt tccgagtaga aagtgtggaa ctgatttgta tggaacagat ggaggacaac    3720
aga                                                                 3723

<210> SEQ ID NO 8
<211> LENGTH: 3936
<212> TYPE: DNA
<213> ORGANISM: Bacillus thuringiensis

<400> SEQUENCE: 8
atgagaacaa atttgacaga acatagaaaa ataaaaaaag gaggcttata catgaatcca      60
aattacaaca ataaacatga gatcttagat acgaataaca gaagctatca aaccagatat    120 cccccttgcga atgcaccagg tgttgaatta caacaaatga gttataagga ttggatggat    180
aggtgtgccg gtgtggaatc aggagaatta tttaggggacg ctacagatgc aattaggtat    240
agtcttattg ttgggacagg gattggatgg gctctctttag gattcgttcc aggtgttggt    300
ccagcattat ctgccgcagc aggtgtattg aatgtaatca ttccatatct atggccagag    360
gaagtcggac ctcctggaac tccccaagcg caacttacgt gggaacagct gatgaatgct    420
gtggaacaaa tgatagatca aaaagttgat accttaataa gagaccgagc tatcgaaaca    480
acccgaatct tacagtcacg tttaagagat tatcaacaag cactttgtaa tttgcaaagt    540
gatccaaata tgaagcttta aaagcggac gtaagaagag agttcaatga tgctgaggat    600
caagcaaagg cagctatcat tcaatttagt cctacaactg gaaatacaac tgaagataca    660
aaaaataata ttctactatt agctgattac acgcaagcta cgaatgtgca tttaattta    720 ttgcgagatg ttatcaaatt tggagaaagt tggggatttt catcacttga agtccaacaa    780
```

```
tattattcca atacaagtcc aatagggaac ccaggtatgt tacaactatt aaacatatat    840
acagagcatt gtttaaattg gtatgataag ggattacagc aacaatatgg aacgggtgac    900
tggaataaat tcaacaattt ccgtagaaat atgacaatca tggcacttga tacagtatca    960
gtatggccaa cctttaatcc gaagcactat tcgctaccta caaaatcaca acttacaagg   1020
acgctgaata catcttttat tagagctcat ggcaacacct ctaagatctc agacatagaa   1080
aataatgtag ttgctcctac aggtctattt aaatggttgc gtaaggtaga ttattatgcg   1140
gcgactgatt tttctcatcc tgccctgtgg tgcggtctag tacaatacta ccatcctact   1200
ctgagtgatg tattggaaga ggatgtgaag gggtctcgtg atacatatat gggatccctt   1260
actgttccag aacctgtact cgaagatgat gtttcgttga ttacgactaa ctattcttat   1320
atgggttatc caccgaatga ggagattagt tatttcaatg aagttacatt tcatttgacc   1380
aaatctgcgg atcagacggt aacatttaat tctactactt accccctattc tagaaaattc   1440
ggattccctt gtagaccgaa taatgctact gcttgtgatc cttgtgattc tgataatcct   1500
tgtacaaatg aaattcctaa tctcacggat ccttgtgatg acaaatcgct ttatagtcat   1560
cgattctcat atatgggtgc gggatttcct tataatctag gtggttttag tttcggatgg   1620
acacacgtaa gtgcagatgc aaacaacctt atagatccta aaaagattac ccaaattcca   1680
gcggtgaagg catacaattt agaaaatgct agggtgataa aaggacctgg gagcacggga   1740
ggagatttag tagaattctc taatggggct acacaaggaa aaatgtatat ggccatcaca   1800
tcgccaaaag gggaagacca gtattataat ttaaggttac gttatgcaag taataatccg   1860
acgactacca taagcattaa tcagggagga cctagttatg cccattctac tgcaactgac   1920
attacaaatc tcacgtatga taaatttggg tacgcaaata tcaactatag aataggtttg   1980
ctaccagaaa gtatagatta tttcactctc gaagttacag gtactgattc aggaacattc   2040
atcctcgaca aaatcgaatt cattccaata gaaggatccg tggaagaatt tgaagcgaat   2100
caggatatag aaaaagcaag aaaggcagtg aatgccttgt ttacaggtga tgcgaaaagt   2160
gctctaaaat tgaacatcac agattatgca gtggatcaag ctgccaattt ggtagaatgt   2220
gtatcagagg aattccatgc ccaagaaaaa ataatcctcc tggatcaagt gaaaatggca   2280
aaacgactca gtcaagtacg gaatctatta aactatggtg attttgaatc gccagattgg   2340
tcgggagaga acggatggaa aacaagcaca catgtttctg tcagagccga taacccagtc   2400
tttaaaggac gctatctcca tatgccaggt gggatgagcc ctcaattctc taacaatatc   2460
tatccaacgt atgcgtatca aaaagtggat gagtcaaaat taaatcccta tacacgttac   2520
ctcgtacgtg gatttgttgg aaatagtaaa gatctagaat tactggtaga acgatatgga   2580
aaagatgtac atgtcgaaat ggatgtacca aatgacatcc gatattcttt accaatgaat   2640
gaatgtggtg gttttgatcg gtgcaaacca gcatcctatc aagcaagaac acgtcatgca   2700
tgcacatgta aaaataacgc tgtagcgcat acggattgtc agtgcaaaga caagaaaaaa   2760
cgtacttcga cgaacatgta tacaaatgtg ccagcagata gtgcagtgta tacgaatgga   2820
ttccatgccc acaagtcctg tgaatgcaag aacaatgaca tgtatcagaa cggaacacag   2880
tcgcataaat cgtgtggata caaagaccca catgtcttca cgtaccatat tgacacagga   2940
tgtgtggaca tggaagaaaa cgtaggtcta ttctttgctt taaaaattgc gagcgaaaat   3000
ggtgtcgcaa acatcaataa tttagaaatc attgaggctc agccgctaac aggagaagca   3060
ttagcacgtg tgaaaaaacg ggaacagaaa tggaaacagg aaatagcgca aaaacgttta   3120
cgaacagaga aagctgtaca agcagcgaaa ggtgcactgc agactctatt cgcaaacgcg   3180
```

-continued

| | |
|---|---|
| cagtacaatc gtctcaaatt tgaaaccctg ttcccacaaa ttgtccatgc agagaaactc | 3240 |
| gtacagcaga tcccatatgc gtaccatcca ttcttgagcg gggcgctgcc aactgtacca | 3300 |
| ggtatgaatt ttgaaatcat ccaacaacta ttggcagtga tcggaaatgc ccgtacatta | 3360 |
| tacgagaaac gaaatctcgt gcgtactggt acattcagct caggtaccgg aagttggaaa | 3420 |
| gtgacagaag gtgtaaaggt gcagccactg caagacacat ctgttctggt tctgtcggaa | 3480 |
| tggagtcatg aagcgtccca gcagttccgt attgatccag atcgcggata tgtattacgt | 3540 |
| gtaacagcgc gaaaagaagg cggaggaaaa gggactgtca ctatgagtga ctgtgcagac | 3600 |
| tatacagaga cactgacctt tacatcatgt gactataaca cgtatggtcc cccaacgctg | 3660 |
| acaagtggta cattatctgg atttgtgacg aagacgttag aagttttccc agatacggat | 3720 |
| cggattcgaa ttgatatggg ggaaaccgaa ggaacgttcc aagtagaaag tgtgaactc | 3780 |
| atttgtatgg aacagatgga agatgactta tatgatatgg cgggaaactt agaggaagag | 3840 |
| atgcagtatt tggagcaatc ccgttcgatg ggcaatacag aatttatacc accactcacc | 3900 |
| tctcaagctt ccggatgtgt agacactatc tggtgc | 3936 |

```
<210> SEQ ID NO 9
<211> LENGTH: 4278
<212> TYPE: DNA
<213> ORGANISM: Bacillus thuringiensis

<400> SEQUENCE: 9
```

| | |
|---|---|
| atgaacctaa atggtaacaa gaatgaattt gaaatcctag atactggtaa catggcctat | 60 |
| cagccaaggt accctcttac ccagtcacca gcttctgaat tgcaagggat gaattataaa | 120 |
| gagtggataa ataggtgtga agatcaggag ttaggtgaat tatttgtaga ttcaaatgct | 180 |
| gtgagaaatg ccgttgttat aggagcaaag attacagcaa caatcgtagg tatagctttt | 240 |
| ccacctttaa aaataccagc acagatccta agtacgttga ttccagtctt atggccaaaa | 300 |
| gaggcaggcc ctcctggaac tgctgaagcg caatttacat gggagcaaat gatgagtgct | 360 |
| gtggaagaaa tgattgatca aaaagttgag attgcagtaa aagaccgtgc tattgaaacc | 420 |
| ttacaaatct tacaatcacg tataagagat tatcaacaag cactttgtaa tttacaaaca | 480 |
| gatcctgata tgagagatt taaagaggac gtaagaaggg aatttaatga tgccgaagat | 540 |
| caggcgaaag ccgctgtcat ccaatttgga aacccgaatt atgcgattcc attactacct | 600 |
| gattatgcac aagcagctaa tatacactta cttttattac gagatgtcgt acaatacgga | 660 |
| gaaatctggg gattttcgtt cgttgaagtt caacaatatt actttaataa ccaaatagga | 720 |
| aaccccggca tgaaacaact attagcaacc tatacggatc attgtgtacg ttggtataat | 780 |
| aatggtttaa caaatagata cgaaacgggc ggctggaata cattcaatga tttccgtaga | 840 |
| aatatgaccc taatggtaat ggatgttgtg tcattctggc caacctatga tcccatgctc | 900 |
| tataagatac ccacaaaatc acaacttacc cggattgtat atactccctt aattggaagg | 960 |
| gcagacgact ttccaggtat ccagcacca actattggtg agaaagaaag tacactcact | 1020 |
| cagcccccac gtttatttgc atggttacgt gagttatcta ttggcgagac aactttccca | 1080 |
| tattatttct ctacaggttt ctgtggtcgc aaacaaattt ttcagaacac tatggataac | 1140 |
| aatttatggg aggaaccata caagggtct cctggagtca aagacacaca gactcttatt | 1200 |
| attccggcac cagaagttaa cgatgatgta tggcgtatcg tcacttactt aaaaaagatg | 1260 |
| gcggggagca tacagtacga cgagatcatg ggatgggatt tttcttttac taaatcatta | 1320 |
| gatcaacgct tatacagata ccatcttcgt tcggtatcgt caggaatgcc ttgcggtggt | 1380 |

```
tcttttccgg gtccttgcga cccttgtaat tctgtagatc cttgtagctt tgaacttccg    1440
aaccctacga ttccttgtga tgacaaagca ctttatagtc atcgatttgc ttatatgggt    1500
gccggttttg tctccaatct agcagcaatg acatatttta gctacggatg acacacgta    1560 agtgcagatg caaacaatct gatagatgct gagaggatca cccaaattcc agcggtgaag    1620
ggatccgaaa tggagggcac tgcaaaagta atccaaggtc ctggtagcac aggaggagat    1680
ttagtacagt tagattacag aggaaaaata caaatttcta tgacagcgcc agtccgaaaa    1740
ggatatcaat tacgaattcg ttatgcaact gcctccacag cagagataca tgtaagcaga    1800
gtatccatta gagaagatga ttcttcaaat gaagactatt atcacttcga atttttaccg    1860
caaacatatt tggctggatc gttaaatttc aactcctttg gttatactac gatgtctatt    1920
ccattacctc ctggtgctgg tgaacaatgg gatatgtcat ccagtggtt cggtacagat    1980 tcaccaatca tcatcgataa aatcgaattc attccaatag aaggatctgt ggaagaattt    2040
gaagcaaatc aagctgtaga aaagcacgg aaggcagtga acgccttgtt tacgaatgat    2100
gcaaagaatg ccttacaact gaatgtcaca gattatgcag tggatcaagc tgccaatctt    2160
gtggagtgtg tatcagagga attccatgca caagaaaaaa tgattcttct ggatcaagtc    2220
aagtttgcga acgtctgag tcaagagcga aatctattaa actacggaga ttttgaatcg    2280
tcagattggt cggagagaa tggatggaga accagtcctc atgtccatgt gacatctgat    2340
aatccaatat ttaaagggcg atatctccac atgccaggtg caatgagccc tcaattctct    2400
aacaatatct atctaacgta tgcctaccaa aagtggatg agtcaaaatt aaaatcttat    2460
actcgttacc ttgtaagggg atttgtaggg aatagtaaag acctggaatt attagtagaa    2520
cgatatggaa aagaagtaca tgtggaaatg gatgtaccca tgatatacg gtactcttta    2580 ccaatgaatg actgtggtgg ctttgatcga tgcaaaccag tatcctatca agaaagactt    2640
cctcatacat gcacatgtaa agataccgct gtagcgcata cagattgtga gtgtaaagac    2700
aaagtgaatc gtacttcggc ggatgtatat acaaatatga tgacagatca tgcggtagat    2760
acgaatggat tccattcgca ccaatcctgt ggatgcaaga ataacgacac gtctcggaac    2820
ggaaaacatc cgcataagtc ttgtggatgc caagacccac atgtcttcac gtaccatatt    2880
gacacagggt gtgtagatca agaagaaaac ttaggtctat tctttgcttt aaaaatcgcg    2940
agcgaaaatg gtatcgcaaa cattgataac ttagaaatca ttgaagcgca gccactcaca    3000
ggggaagcat tggctcgtgt aaaaaaacga gaacacaaat ggaaacaaga atgatacaa    3060 aaacgtttac aaacagagaa agccgtacaa gcagcgaggg gtgcgattca gaatctgttc    3120
acaaacgcgc aacaaaccca actgaaacac gaaaccttgt ttcctgagat tctaaacgca    3180
gggaaattgg tccaagacat tccctatgtg catcacccat tcttgagcgg ggcactgcta    3240
accgtaccgg gcatgaattt cgatgttttc caacaacttt ccttcttgag tgagacagca    3300
agaggattat atgagcaacg aaaccttgtc tcaaacggta cgtttggtgc tggaatcgca    3360
aattggaatg cgacggatgg tgtgactgta cagccggagg ggccaacatc cgtactggtt    3420
ttatccaatt ggagtgacaa agcgttccaa aatctgcgat tagatccaga ccgtgggtat    3480
gtcctacgtg tgacagcacg aaaagaaggc agaggaaaag ggactgtgac gatcagtgac    3540
tgtacggcgt atccagaaac actcctcttt acatcttgtg acaagaacac aatcgatacg    3600
tttgtgacaa aaacgctgga aattttcccg gatacagatc gtatccgtat tgacatcggt    3660
gaaacagaag gcatgttcaa aatcgaaagt gtggaactga tttgtatagaa acacatggaa    3720 gaccatatat atgatatggc tagagtaggt ccagcaaaag ccgaagaaca tccaattta    3780
```

-continued

```
aaagatgcaa acggtagtcc ggttgtatat ggacaggaat attacatgga gccctacgaa    3840
tttccaggtt ataaattagg agaaagcatt aatgtggggg gaatcaatga gattgcatta    3900
gcacctagta tgtatatgaa accgatggaa cttacattcg aaaaaaatgt tacaactcca    3960
gaagatatgg tattcataca acataaagcc actggcccgg ggtcaggttt acatgggatt    4020
cattatgtgt ctgtatttga ttccagtaca tcgtatcttc aattgatgta tccctccacg    4080
gatgctaatc aatctatgtg gaaaccgatt cttccatctg tagatatgga ttctaaattt    4140
atagatggca attattttgc atttaaaaat gaaaatctta atgtatttct tgcgtatcaa    4200
aacctaaatg agcgtcatag ctatgcacat gttggtacta tgaattcaaa aacgatgtgg    4260
cgtttaattc caatacaa                                                 4278
```

<210> SEQ ID NO 10
<211> LENGTH: 1782
<212> TYPE: DNA
<213> ORGANISM: Artificial Sequence
<220> FEATURE:
<223> OTHER INFORMATION: synthetic nucleotide sequence encoding AXMI218
      (axmi218v01.02)

<400> SEQUENCE: 10

```
atgtcagaat atgaattgat tgatgtttct ccaaaacctt acaatgtttt gatgcaaaga      60
ccagatgaag ctggaggaat tgattgggat gctgaaattt caaagatgat caaaacatat     120
tatcaaaaag gaacatttgc tgctgatttt gcaacaatca ttcttccatt gattcttgct     180
cacaatgttc aatggaatgt tgttttgaag agtgttcttt cttttgcttc tgctcttcct     240
ggaattggaa ctgctgtttc aattctttct ccatttcttc aattgttgtt tccaacagat     300
cctgctgctc atgacaagca attgatgaag ctcattttgg atcaaacaaa gattttgatt     360
gatcaagctg tttctcaaga agtgatgaac agaatttctc aacaaatcac tggattatat     420
gcaaatttgg caagattcaa cagaacaatt gctgcttatg aaactttggc tccaacaaca     480
atcattgctg aaattcaagc aattgaagct gttttttgaca atcaagttcc tcaattggtt     540
gatcctggat atttggcttt gacacttcct ctttatgttc aaggaatcaa tttgaatttg     600
atgttttaca aatcagtttt ggatcatgct gaacaattga agattcctgc tggagaacaa     660
aattattaca aaacttcttt gagagacaaa atcaaaactg cttctgctca agttacacaa     720
tatttcaaac aagttccttg gaggccaaat gaaatcactc cttcttctgc ttcaaatcaa     780
gatattgtga caagacaaac aatgtacact cattgttttgg attatgttgc aatgtggcca     840
acattcaatc cagatcttta tcctctttct gctgatattg aacaaacaag agttctttct     900
tcaccaattt ctggattgcc aggaaaacct ggagcttatg gaccatttgt tgattttctt     960
ggatttgatg atactttgga attgacaagc atcacatatt ggcaaggaga cagaattgac    1020
agaattgatc aaaatttcac atatggaaga gtgatcagag gaggaagtgg aggaggagga    1080
agcagacatg atattccttc ttcaagagca atccaattgc ttctctttg gatggattac    1140 aattcaaaca attatcaatt tgtttcttat caaatgtaca acactctcat agattacaca    1200
aaacctcaaa caaatcttct tcttgctcct ccaaatcaca aattgcacag attgtacaca    1260
acagatgatc cttcatttgg aggaagagtt ggaacaattg gaaatcaatt cattcaaaac    1320
acaatttttc cagaaaacat catgggaaca tttgatcaag atcttggagt gacaagaatc    1380
aaagggattc catttgaaaa atctccttca caactgctt tcacatatgc aaaagaacca    1440
ttgaatggag cagaagctgt gaaacttgga atcagacaaa ctttggatct tccaatcaca    1500
aatgtgacaa ctggatggta tcaaatcaga atcagatatg cttcaacaga tttgacaagc    1560
```

```
attgagttca aattggatgt tggaggacaa agtttgattg acaaaactgt tgttcttcct    1620
gcaacaacaa ctggagatcc aactggaatt gaaggagcaa atggaacata cactttgttg    1680
acaattcaag aaatttcaat tcctgctgga aattttcatg tttatgtgac aaacaatttt    1740
ggaccaaatt tgttttttgga cagaattgaa tttgttccaa tg                      1782
```

<210> SEQ ID NO 11
<211> LENGTH: 2013
<212> TYPE: DNA
<213> ORGANISM: Artificial Sequence
<220> FEATURE:
<223> OTHER INFORMATION: synthetic nucleotide sequence encoding AXMI219
      (axmi219v01.02)

<400> SEQUENCE: 11

```
atggaacaac atgctttggt tcctcaaaac atgacaagca cactggatt gattccttac       60 aatgtttatg caactgctcc ttcaaatttt gcttctttca ctgatgtttt caatgatttg     120
aaagaagcat atgatgaatt tcaaaaaact ggagcaattg atgttttgaa gcaacatttg     180
aatgttgctt ggaacactta caaaacaaat tctgttgatt atttggcttt gatcaaagca     240
acaatttctc ttcttggatt cactcctgct ggacctgctg ttccttttcat caacatgttt    300 gttgatatgg tttttccaat gttgtttgga ggatcaggag ctgacaagaa cacaattttc     360
tttgaaatga tcatggatca agttgaacaa ttggttgatc aaaaatttga agcattcact     420
ttgaacaatt gaacaacat cattgaagga attgaaacaa atttggtgga ttttcaaaat      480
gcaattcaaa ttgcaatttg ccaaggagaa ggacctggat tgagaagtga tccttgcact    540
ccttcaattg atcatcttca aaagtttac actgctttca caacagcaag aagccaaatt      600
caaacaaatc ttcctcattt caagaatcca atggatcttg aaacacaaa ttttcaatca      660 gattttgttc ttctcactct tcctctttac acaaatgttg caaatttgaa tcttcttctt     720
catcatggat tcattcaatt tgctgaaaaa tggaaaagtg tttattatga tgaaggaaca     780
atgaatcaag tgaaagctga tcttcaacac aggattcaag aatattcaac aacagttttg     840
aacacttaca tcaatatct tcctgctgtt ggaagttcaa atctcaaac aaacagaaga       900 atcagatata tcagaggaat gacaattgga gctcttgata ttgcttctct ttggccaaca     960
atggacaatc tttattatcc aatgagaaca gatttggatc aaacaagatt gacattcatg    1020
gatgttgttg gaccaattga aggacaagat ttcactcttt catttccaaa tggagatatg    1080
gaaagatatg gatattttgg aagagaattg acaaaaattg aacctcatta cagaaaagca    1140
aaagctcaca cactggagc aagagaatac aacatcacaa atggaatgag aaattctgga    1200
aagaatgctt tgaatcaaga ttcaacagat acttggggac aaatgatgt ttcttatgct     1260 gatttcttca attcttctgg atatcttcaa gttttgctc cagtttcttt tgtcaacatg     1320
tcaagtggaa gtggaacata ttatgattac aacaaatttg ctgctcttgg agtgaatgga    1380
aacattgttt ctcctccata tgctgattct cttggaaatc caatttcttc aaagaacatt    1440
ccaattttgg atcaaaagat caattatctt tatccagtga ctggaagtgg aattgctgaa    1500
aagatgggat tcttgcttc aattgttcaa gctgatcttt atccagaaaa catcattgga    1560
acaattgatc caattgatgg aagccaaagc atcaagggga ttccatttga caatgcaca    1620 aatcttcaaa tttcaagatt gaaagaacca ttgaatggag ctcctgctgt tcaactttca    1680
aatggaagtt ctttgacatt gagcatcaca aacatggttt ctcaaccata tcaaatcaga    1740
atcagatatg cttgtccaac tgatacaaca attttcttga atgttgcaac tggtggacat    1800
```

```
tcaccagttt atcaaagcat cactcttcct gcaacaaatt ctggaactgg acacactgtt    1860
cctggaacaa acaatggaat gttttacact gtttttccaa caagaactgg aactccaatc    1920
actgcaacaa ttccttctgg aaatttcaat gtttatgtga cacacaatga ttctgcaaat    1980
ttgttgttgg acagaattga atttattcca aca                                 2013
```

<210> SEQ ID NO 12
<211> LENGTH: 2034
<212> TYPE: DNA
<213> ORGANISM: Artificial Sequence
<220> FEATURE:
<223> OTHER INFORMATION: synthetic nucleotide sequence encoding AXMI220
      (axmi220v01.02)

<400> SEQUENCE: 12

```
atggaacaaa acaatgttct ttcagaagaa ggagctcaat caatgagtgt ttcttctgtt      60
gaatctccat tgattcctta caatgtttat gcaactgctc cttctcctct tccttcaaat     120
ttggcttctt tcaatgatat tttcaatgat ttgaaaggag cttatgatga attttcaaaa     180
actggagcaa ttgatgtttt gaagcaacat ttgaatgttg cttggggagc ttacaaaaat     240
tctgctgttg attatttggc tttgatcaaa gcaacaattt cattgcttgg attcactcct     300
gctggacctg ctgttccttt catcaacatg tttgttgata tgattttttcc tgttttgttt     360 ggaggaacaa ctcaagacaa gaacaaaatt tcctttgata tgatcatgga acaagttgaa     420
caattagttg atcaaaaatt tcaaaatttc acaatcaaca atttgaacaa catcattgat     480
ggaatccaaa ctgttttggt ggattttcaa aatgcaattc aagttgcaat tgccaagga     540 gaatcaccag gattgagaag tgatccttgc actccttctg ctgctcattt ggaacaagtt     600
catgttgctt tcacaacagc aagagcaaca attcaaactc aacttcctca tttcaagaat     660
ccaatggatc ttggaaatcc aaattttcaa tcagattttg ttttgttgac acttcctctt     720
tacactcatg ctgctaattt gaatcttctt cttcatcatg gatatattca attcagagaa     780
aaatggaaaa gtgtttctta tgatgaagga acaatgaatc aaatcaaagc tgatcttcaa     840
cacaggattc aagaatattc tggaactgtt ctttcaacat acactcaata tcttccttct     900
gttggagctt caaaatctca acaaacaga agaatcagat atatcagagg aatgacaatt     960
ggagctttgg atattgctgc tctttggcca acatggatg ctgttcatta tccaatcaga    1020
acagatttgg atcaaacaag attggctttt cttgatgttg ttggaccaat tgaaaacaga    1080
gatttcaatt tgagcttctt gaatggagat atggaaggat acaattattt ttcaagagaa    1140
ttgacaaaga tcactcctca ttacagaact gcaaaaggac caaatgttgg agacagaaat    1200
tatggattga caaatggaat gagaaattat ggaactgatg cttctgatca tcaacaaatt    1260
gatacaagtg gaccttcaga tgaatatcac aacaatttct acaacactgc tggatatgct    1320
gaagttgatg ctccaatcag ttatgtgaac atgtggagtg atgctgctct ttattatgat    1380
tacaacaaat ttggagcaac aaatgcaaat ggagatgttg ttgttcctcc aaacactgat    1440
gcaattggaa atccagtttta ttcaagaac attccaattt tgaatcaaaa gatcaattat    1500
atgtatcctg tcactggtgc tggaatttca gaaagatgg gatttcttgc ttctttggtt    1560
ccatatgatt tgtttccaga aaatttgatt ggacaaattg atccaattga tggaagccaa    1620
agcatcaaag ggattccatt tgaaaaatca acaccattga cagttccaag aaagaaagaa    1680
ccaatcaatg gagcttctgc tgttcaactt ccaagaatc aatatgtcaa catggctttg    1740
acaaatggaa caagtggaga ttatgaaatc agaatcagat atgcttctga tactgctgtg    1800
acaatcactt tgaatgtcac tgctggttca acaacaatca tcaacaatca agcaatcact    1860
```

```
cttcctgcaa caactggatt gcaagcaagt gttcctggaa tcaatggaag ctatgctttg    1920
aatccttctg attcttcttt gaaaacaagg attcctgttg gaaattttca tgtttatgtg    1980
acaaacaaca ctggagacaa tttgtttttg gacagaattg aatttgctcc attg          2034
```

<210> SEQ ID NO 13
<211> LENGTH: 1165
<212> TYPE: PRT
<213> ORGANISM: Bacillus thuringiensis

<400> SEQUENCE: 13

```
Met Ser Glu Tyr Glu Leu Ile Asp Val Ser Pro Lys Pro Tyr Asn Val
 1               5                   10                  15

Leu Met Gln Arg Pro Asp Glu Ala Gly Gly Ile Asp Trp Asp Ala Glu
             20                  25                  30

Ile Ser Lys Met Ile Lys Thr Tyr Tyr Gln Lys Gly Thr Phe Ala Ala
         35                  40                  45

Asp Phe Ala Thr Ile Ile Leu Pro Leu Ile Leu Ala His Asn Val Gln
     50                  55                  60

Trp Asn Val Val Leu Lys Ser Val Leu Ser Phe Ala Ser Ala Leu Pro
 65                  70                  75                  80

Gly Ile Gly Thr Ala Val Ser Ile Leu Ser Pro Phe Leu Gln Leu Leu
                 85                  90                  95

Phe Pro Thr Asp Pro Ala Ala His Asp Lys Gln Leu Met Lys Leu Ile
            100                 105                 110

Leu Asp Gln Thr Lys Ile Leu Ile Asp Gln Ala Val Ser Gln Glu Val
        115                 120                 125

Met Asn Arg Ile Ser Gln Gln Ile Thr Gly Leu Tyr Ala Asn Leu Ala
    130                 135                 140

Arg Phe Asn Arg Thr Ile Ala Ala Tyr Glu Thr Leu Ala Pro Thr Thr
145                 150                 155                 160

Ile Ile Ala Glu Ile Gln Ala Ile Glu Ala Val Phe Asp Asn Gln Val
                165                 170                 175

Pro Gln Leu Val Asp Pro Gly Tyr Leu Ala Leu Thr Leu Pro Leu Tyr
            180                 185                 190

Val Gln Gly Ile Asn Leu Asn Leu Met Phe Tyr Lys Ser Val Leu Asp
        195                 200                 205

His Ala Glu Gln Leu Lys Ile Pro Ala Gly Glu Gln Asn Tyr Tyr Lys
    210                 215                 220

Thr Ser Leu Arg Asp Lys Ile Lys Thr Ala Ser Ala Gln Val Tyr Thr
225                 230                 235                 240

Tyr Phe Lys Gln Val Pro Trp Arg Pro Asn Glu Ile Thr Pro Ser Ser
                245                 250                 255

Ala Ser Asn Gln Asp Ile Val Thr Arg Gln Thr Met Tyr Thr His Cys
            260                 265                 270

Leu Asp Tyr Val Ala Met Trp Pro Thr Phe Asn Pro Asp Leu Tyr Pro
        275                 280                 285

Leu Ser Ala Asp Ile Glu Gln Thr Arg Val Leu Ser Ser Pro Ile Ser
    290                 295                 300

Gly Leu Pro Gly Lys Pro Gly Ala Tyr Gly Pro Phe Val Asp Phe Leu
305                 310                 315                 320

Gly Phe Asp Asp Thr Leu Glu Leu Thr Ser Ile Thr Tyr Trp Gln Gly
                325                 330                 335

Asp Arg Ile Asp Arg Ile Asp Gln Asn Phe Thr Tyr Gly Arg Val Ile
            340                 345                 350
```

```
Arg Gly Gly Ser Gly Gly Gly Ser Arg His Asp Ile Pro Ser Ser
            355                 360                 365
Arg Ala Asn Pro Ile Ala Ser Leu Trp Met Asp Tyr Asn Ser Asn Asn
370                 375                 380
Tyr Gln Phe Val Ser Tyr Gln Met Tyr Asn Thr Leu Ile Asp Tyr Thr
385                 390                 395                 400
Lys Pro Gln Thr Asn Leu Leu Leu Ala Pro Pro Asn His Lys Leu His
                405                 410                 415
Arg Leu Tyr Thr Thr Asp Asp Pro Ser Phe Gly Gly Arg Val Gly Thr
            420                 425                 430
Ile Gly Asn Gln Phe Ile Gln Asn Thr Ile Phe Pro Glu Asn Ile Met
            435                 440                 445
Gly Thr Phe Asp Gln Asp Leu Gly Val Thr Arg Ile Lys Gly Ile Pro
            450                 455                 460
Phe Glu Lys Ser Pro Ser Thr Thr Ala Phe Thr Tyr Ala Lys Glu Pro
465                 470                 475                 480
Leu Asn Gly Ala Glu Ala Val Lys Leu Gly Ile Arg Gln Thr Leu Asp
                485                 490                 495
Leu Pro Ile Thr Asn Val Thr Thr Gly Trp Tyr Gln Ile Arg Ile Arg
            500                 505                 510
Tyr Ala Ser Thr Asp Leu Thr Ser Ile Glu Phe Lys Leu Asp Val Gly
            515                 520                 525
Gly Gln Ser Leu Ile Asp Lys Thr Val Val Leu Pro Ala Thr Thr Thr
            530                 535                 540
Gly Asp Pro Thr Gly Ile Glu Gly Ala Asn Gly Thr Tyr Thr Leu Leu
545                 550                 555                 560
Thr Ile Gln Glu Ile Ser Ile Pro Ala Gly Asn Phe His Val Tyr Val
                565                 570                 575
Thr Asn Asn Phe Gly Pro Asn Leu Phe Leu Asp Arg Ile Glu Phe Val
            580                 585                 590
Pro Met Leu Ser Ser Val Asp Ile Asp Lys Asp Phe Asn Phe Gly Pro
            595                 600                 605
Asn Pro Gly Tyr Gln Leu Val Trp Glu Asp Asp Lys Arg Tyr Gly Arg
            610                 615                 620
Thr Val His Gly Thr Ile Glu Ser Glu Asp Gly Val Leu Leu Phe Thr
625                 630                 635                 640
Ser Gly Gly Asn Val Asp Ile Gln Pro Gly Thr Gln Pro Ile Asp His
                645                 650                 655
Asp Phe Glu Glu Pro Phe Asn Gln Leu Tyr Val Gly Lys Val Gly Gly
            660                 665                 670
Thr Lys Gly His Ile Lys Ala Thr Ile Tyr Leu Asp Asn Pro Gln Lys
            675                 680                 685
Gln Gly Met Phe Thr Thr Asp Ala Asp Leu Ala Lys Val Thr Gln Val
            690                 695                 700
Val Asn Ala Leu Phe Ile Thr Asp Thr Gln Leu Ala Pro Thr Val Thr
705                 710                 715                 720
Asp Tyr Trp Ile Asp Gln Val Tyr Leu Lys Val Lys Ala Leu Ser Asp
                725                 730                 735
Asp Leu Phe Gly Glu Lys Glu Arg Leu Arg Gln Arg Val Ala Arg
            740                 745                 750
Ala Lys Gln Ile Asn Thr Met Lys Asn Lys Leu Ile Gly Ser Ser Phe
            755                 760                 765
Gln Thr Leu Thr Asn Trp Gln Leu Ser Ser Asp Val Ala Leu Leu Ala
```

```
                        770                 775                 780
Asp Asn Pro Leu Phe Ala Gly Thr Tyr Val Leu Pro Pro Ser Thr
785                 790                 795                 800

Tyr Pro Asp Thr Arg Pro Ser Tyr Ala Tyr Gln Lys Val Asp Glu Ser
                805                 810                 815

Lys Leu Lys Pro Tyr Thr Arg Tyr Ile Val Arg Gly Phe Ile Gly Gln
                820                 825                 830

Ala Gln Asp Leu Ala Leu Leu Val Ser Arg Tyr Gly Lys Glu Val Asp
                835                 840                 845

Thr Ala Leu Thr Val Pro Tyr Gln Glu Ala Leu Pro Leu Ser Pro Asp
                850                 855                 860

Ser Thr Ser Asn Cys Cys Gly Pro Val Ala Cys Pro Pro Cys Glu Gly
865                 870                 875                 880

His Glu Tyr Asp Thr His Leu Phe Ser Tyr Thr Ile Asp Val Gly Ala
                    885                 890                 895

Leu Gln Ser Glu Ile Asn Leu Gly Ile Glu Ile Gly Phe Lys Ile Thr
                900                 905                 910

Ser Pro Thr Gly Phe Ala His Ile Ser Asn Leu Glu Ile Val Glu Asp
                915                 920                 925

Arg Pro Leu Thr Glu Ala Glu Thr Ile Lys Val Lys Gln Arg Glu Lys
                930                 935                 940

Lys Trp Met Arg Leu Ser Gln Lys Gln Ser Gln Met Gln Ala Gln
945                 950                 955                 960

Tyr Asp Gln Thr Met Gln Tyr Phe Ala Asn Leu Tyr Thr Thr Pro Asp
                    965                 970                 975

Gln Thr Glu Leu Gln Asn Thr Val Gln Tyr Thr Asp Ile Ala Lys Val
                980                 985                 990

Gln Val Val Thr Phe Pro Ser Pro Met Gln Trp Phe Ile Pro Gln Leu
                995                 1000                1005

Pro Arg Ser Ser Ser Ala Met Val Gln Glu Leu Ile Asn Ala Lys Glu
     1010                1015                1020

Lys Ala Leu Arg Leu Tyr Pro Ala Asn Leu Thr Gln Asn Gly Asp Phe
1025                1030                1035                1040

Ala Thr Gly Leu Ser Asn Trp Asp Val Ile Pro Asp Thr Asn Ala Ser
                1045                1050                1055

Ile Asp Thr Val Asp Gly Thr Ser Val Leu Arg Val Pro Ser Trp Asp
                1060                1065                1070

Glu Thr Val Ser Gln Thr Ile Thr Leu Pro Pro His Gln Glu Asp Val
                1075                1080                1085

Leu Tyr Gln Leu Arg Val Thr Ala Lys Gly Asn Gly Ser Val Gly Leu
                1090                1095                1100

Gln His Asn Gly Glu Gln Glu Arg Leu Tyr Phe Asn Gln Asn Asn Pro
1105                1110                1115                1120

Asn Gly Asn Thr Phe Val Thr Lys Ser Thr Ser Phe Tyr Pro Thr Ala
                1125                1130                1135

Ser Thr Leu Ser Ile Gln Ile Gln Ser Glu Gly Thr Asp Phe Tyr Val
                1140                1145                1150

Lys Thr Ile Glu Val Phe Val Gln Pro Val Pro Leu Thr
            1155                1160                1165

<210> SEQ ID NO 14
<211> LENGTH: 594
<212> TYPE: PRT
<213> ORGANISM: Bacillus thuringiensis
```

<400> SEQUENCE: 14

```
Met Ser Glu Tyr Glu Leu Ile Asp Val Ser Pro Lys Pro Tyr Asn Val
 1               5                  10                  15

Leu Met Gln Arg Pro Asp Glu Ala Gly Gly Ile Asp Trp Asp Ala Glu
             20                  25                  30

Ile Ser Lys Met Ile Lys Thr Tyr Tyr Gln Lys Gly Thr Phe Ala Ala
         35                  40                  45

Asp Phe Ala Thr Ile Ile Leu Pro Leu Ile Leu Ala His Asn Val Gln
     50                  55                  60

Trp Asn Val Val Leu Lys Ser Val Leu Ser Phe Ala Ser Ala Leu Pro
 65                  70                  75                  80

Gly Ile Gly Thr Ala Val Ser Ile Leu Ser Pro Phe Leu Gln Leu Leu
                 85                  90                  95

Phe Pro Thr Asp Pro Ala Ala His Asp Lys Gln Leu Met Lys Leu Ile
            100                 105                 110

Leu Asp Gln Thr Lys Ile Leu Ile Asp Gln Ala Val Ser Gln Glu Val
        115                 120                 125

Met Asn Arg Ile Ser Gln Gln Ile Thr Gly Leu Tyr Ala Asn Leu Ala
130                 135                 140

Arg Phe Asn Arg Thr Ile Ala Ala Tyr Glu Thr Leu Ala Pro Thr Thr
145                 150                 155                 160

Ile Ile Ala Glu Ile Gln Ala Ile Glu Ala Val Phe Asp Asn Gln Val
                165                 170                 175

Pro Gln Leu Val Asp Pro Gly Tyr Leu Ala Leu Thr Leu Pro Leu Tyr
            180                 185                 190

Val Gln Gly Ile Asn Leu Asn Leu Met Phe Tyr Lys Ser Val Leu Asp
        195                 200                 205

His Ala Glu Gln Leu Lys Ile Pro Ala Gly Glu Gln Asn Tyr Tyr Lys
210                 215                 220

Thr Ser Leu Arg Asp Lys Ile Lys Thr Ala Ser Ala Gln Val Tyr Thr
225                 230                 235                 240

Tyr Phe Lys Gln Val Pro Trp Arg Pro Asn Glu Ile Thr Pro Ser Ser
                245                 250                 255

Ala Ser Asn Gln Asp Ile Val Thr Arg Gln Thr Met Tyr Thr His Cys
            260                 265                 270

Leu Asp Tyr Val Ala Met Trp Pro Thr Phe Asn Pro Asp Leu Tyr Pro
        275                 280                 285

Leu Ser Ala Asp Ile Glu Gln Thr Arg Val Leu Ser Ser Pro Ile Ser
290                 295                 300

Gly Leu Pro Gly Lys Pro Gly Ala Tyr Gly Pro Phe Val Asp Phe Leu
305                 310                 315                 320

Gly Phe Asp Asp Thr Leu Glu Leu Thr Ser Ile Thr Tyr Trp Gln Gly
                325                 330                 335

Asp Arg Ile Asp Arg Ile Asp Gln Asn Phe Thr Tyr Gly Arg Val Ile
            340                 345                 350

Arg Gly Gly Ser Gly Gly Gly Ser Arg His Asp Ile Pro Ser Ser
        355                 360                 365

Arg Ala Asn Pro Ile Ala Ser Leu Trp Met Asp Tyr Asn Ser Asn
370                 375                 380

Tyr Gln Phe Val Ser Tyr Gln Met Tyr Asn Thr Leu Ile Asp Tyr Thr
385                 390                 395                 400

Lys Pro Gln Thr Asn Leu Leu Leu Ala Pro Pro Asn His Lys Leu His
                405                 410                 415
```

```
Arg Leu Tyr Thr Thr Asp Asp Pro Ser Phe Gly Gly Arg Val Gly Thr
                420                 425                 430

Ile Gly Asn Gln Phe Ile Gln Asn Thr Ile Phe Pro Glu Asn Ile Met
            435                 440                 445

Gly Thr Phe Asp Gln Asp Leu Gly Val Thr Arg Ile Lys Gly Ile Pro
450                 455                 460

Phe Glu Lys Ser Pro Ser Thr Thr Ala Phe Thr Tyr Ala Lys Glu Pro
465                 470                 475                 480

Leu Asn Gly Ala Glu Ala Val Lys Leu Gly Ile Arg Gln Thr Leu Asp
                485                 490                 495

Leu Pro Ile Thr Asn Val Thr Thr Gly Trp Tyr Gln Ile Arg Ile Arg
            500                 505                 510

Tyr Ala Ser Thr Asp Leu Thr Ser Ile Glu Phe Lys Leu Asp Val Gly
        515                 520                 525

Gly Gln Ser Leu Ile Asp Lys Thr Val Val Leu Pro Ala Thr Thr Thr
    530                 535                 540

Gly Asp Pro Thr Gly Ile Glu Gly Ala Asn Gly Thr Tyr Thr Leu Leu
545                 550                 555                 560

Thr Ile Gln Glu Ile Ser Ile Pro Ala Gly Asn Phe His Val Tyr Val
                565                 570                 575

Thr Asn Asn Phe Gly Pro Asn Leu Phe Leu Asp Arg Ile Glu Phe Val
            580                 585                 590

Pro Met

<210> SEQ ID NO 15
<211> LENGTH: 1243
<212> TYPE: PRT
<213> ORGANISM: Bacillus thuringiensis

<400> SEQUENCE: 15

Met Glu Gln His Ala Leu Val Pro Gln Asn Met Thr Ser Asn Thr Gly
  1               5                  10                  15

Leu Ile Pro Tyr Asn Val Tyr Ala Thr Ala Pro Ser Asn Phe Ala Ser
                20                  25                  30

Phe Thr Asp Val Phe Asn Asp Leu Lys Glu Ala Tyr Asp Glu Phe Ser
            35                  40                  45

Lys Thr Gly Ala Ile Asp Val Leu Lys Gln His Leu Asn Val Ala Trp
        50                  55                  60

Asn Thr Tyr Lys Thr Asn Ser Val Asp Tyr Leu Ala Leu Ile Lys Ala
 65                  70                  75                  80

Thr Ile Ser Leu Leu Gly Phe Thr Pro Ala Gly Pro Ala Val Pro Phe
                 85                  90                  95

Ile Asn Met Phe Val Asp Met Val Phe Pro Met Leu Phe Gly Gly Ser
            100                 105                 110

Gly Ala Asp Lys Asn Thr Ile Phe Phe Glu Met Ile Met Asp Gln Val
        115                 120                 125

Glu Gln Leu Val Asp Gln Lys Phe Glu Ala Phe Thr Leu Asn Asn Leu
    130                 135                 140

Asn Asn Ile Ile Glu Gly Ile Glu Thr Asn Leu Val Asp Phe Gln Asn
145                 150                 155                 160

Ala Ile Gln Ile Ala Ile Cys Gln Gly Glu Gly Pro Gly Leu Arg Ser
                165                 170                 175

Asp Pro Cys Thr Pro Ser Ile Asp His Leu Gln Lys Val Tyr Thr Ala
            180                 185                 190

Phe Thr Thr Ala Arg Ser Gln Ile Gln Thr Asn Leu Pro His Phe Lys
```

```
                195                 200                 205
Asn Pro Met Asp Leu Gly Asn Thr Asn Phe Gln Ser Asp Phe Val Leu
    210                 215                 220

Leu Thr Leu Pro Leu Tyr Thr Asn Val Ala Asn Leu Asn Leu Leu Leu
225                 230                 235                 240

His His Gly Phe Ile Gln Phe Ala Glu Lys Trp Lys Ser Val Tyr Tyr
                245                 250                 255

Asp Glu Gly Thr Met Asn Gln Val Lys Ala Asp Leu Gln His Arg Ile
                260                 265                 270

Gln Glu Tyr Ser Thr Thr Val Leu Asn Thr Tyr Asn Gln Tyr Leu Pro
                275                 280                 285

Ala Val Gly Ser Ser Lys Ser Gln Thr Asn Arg Arg Ile Arg Tyr Ile
    290                 295                 300

Arg Gly Met Thr Ile Gly Ala Leu Asp Ile Ala Ser Leu Trp Pro Thr
305                 310                 315                 320

Met Asp Asn Leu Tyr Tyr Pro Met Arg Thr Asp Leu Asp Gln Thr Arg
                325                 330                 335

Leu Thr Phe Met Asp Val Val Gly Pro Ile Glu Gly Gln Asp Phe Thr
                340                 345                 350

Leu Ser Phe Pro Asn Gly Asp Met Glu Arg Tyr Gly Tyr Phe Gly Arg
                355                 360                 365

Glu Leu Thr Lys Ile Glu Pro His Tyr Arg Lys Ala Lys Ala His Asn
    370                 375                 380

Thr Gly Ala Arg Glu Tyr Asn Ile Thr Asn Gly Met Arg Asn Ser Gly
385                 390                 395                 400

Lys Asn Ala Leu Asn Gln Asp Ser Thr Asp Thr Trp Gly Pro Asn Asp
                405                 410                 415

Val Ser Tyr Ala Asp Phe Phe Asn Ser Ser Gly Tyr Leu Gln Val Phe
                420                 425                 430

Ala Pro Val Ser Phe Val Asn Met Ser Ser Gly Ser Gly Thr Tyr Tyr
                435                 440                 445

Asp Tyr Asn Lys Phe Ala Ala Leu Gly Val Asn Gly Asn Ile Val Ser
    450                 455                 460

Pro Pro Tyr Ala Asp Ser Leu Gly Asn Pro Ile Ser Ser Lys Asn Ile
465                 470                 475                 480

Pro Ile Leu Asp Gln Lys Ile Asn Tyr Leu Tyr Pro Val Thr Gly Ser
                485                 490                 495

Gly Ile Ala Glu Lys Met Gly Phe Leu Ala Ser Ile Val Gln Ala Asp
                500                 505                 510

Leu Tyr Pro Glu Asn Ile Ile Gly Thr Ile Asp Pro Ile Asp Gly Ser
                515                 520                 525

Gln Ser Ile Lys Gly Ile Pro Phe Asp Lys Cys Thr Asn Leu Gln Ile
    530                 535                 540

Ser Arg Leu Lys Glu Pro Leu Asn Gly Ala Pro Ala Val Gln Leu Ser
545                 550                 555                 560

Asn Gly Ser Ser Leu Thr Leu Ser Ile Thr Asn Met Val Ser Gln Pro
                565                 570                 575

Tyr Gln Ile Arg Ile Arg Tyr Ala Cys Pro Thr Asp Thr Thr Ile Phe
                580                 585                 590

Leu Asn Val Ala Thr Gly Gly His Ser Pro Val Tyr Gln Ser Ile Thr
                595                 600                 605

Leu Pro Ala Thr Asn Ser Gly Thr Gly His Thr Val Pro Gly Thr Asn
    610                 615                 620
```

-continued

```
Asn Gly Met Phe Tyr Thr Val Phe Pro Thr Arg Thr Gly Thr Pro Ile
625                 630                 635                 640

Thr Ala Thr Ile Pro Ser Gly Asn Phe Asn Val Tyr Val Thr His Asn
            645                 650                 655

Asp Ser Ala Asn Leu Leu Leu Asp Arg Ile Glu Phe Ile Pro Thr Val
        660                 665                 670

Ser Pro Pro Pro Pro Pro Ser Asn Gln Ile Asn Lys Val Leu Asp
    675                 680                 685

Leu Thr Pro Gln Arg Pro Gln Asn Ile Trp Ser Tyr Pro Thr Gly Trp
690                 695                 700

Ala Asp Ala Val Asp Ile Asn Gly Val Ser Asn Gly Ala Phe Ser Ile
705                 710                 715                 720

Gln Tyr Ile Ser Arg Gly Arg Val Ile Arg Asn Val Asp Lys Thr Ser
                725                 730                 735

Gly Pro Phe Ser Asp Lys Tyr Pro Pro Ala Pro Asp Ser Trp Phe Asn
            740                 745                 750

Phe Asp Thr Ile Gln Phe Val Ala Tyr Ser Asn Val His Cys Ser Val
        755                 760                 765

Ser Gly Ser Val His Ile Met Glu Thr Val Lys Asn Ile Phe Glu Thr
770                 775                 780

Glu Glu Asp Leu Ala Lys Val Thr Asp Val Val Asn Ala Leu Phe Ile
785                 790                 795                 800

Thr Asp Thr Gln Leu Ala Pro Thr Val Thr Asp Tyr Trp Ile Asp Gln
                805                 810                 815

Val Tyr Leu Lys Val Asn Ala Leu Ser Asp Glu Trp Phe Glu Glu
            820                 825                 830

Lys Thr Gln Leu Arg Ile Lys Leu Asn Arg Ala Lys Gln Leu Arg Thr
        835                 840                 845

Met Gln Asn Leu Leu Val Gly Gly Asp Phe Thr Asn Leu Met Gln Trp
850                 855                 860

Arg Met Ser Pro Tyr Thr Thr Leu Arg Thr Asp Ser Asp Leu Phe Val
865                 870                 875                 880

Asp Lys Tyr Ile Leu Leu Gln Pro Ser Met Asp Pro Ile Thr Lys Pro
                885                 890                 895

Ser Tyr Val Tyr Gln Lys Val Glu Glu Gln Lys Leu Lys Pro Tyr Thr
            900                 905                 910

Arg Tyr Thr Val Thr Gly Phe Leu Ala Gln Ala Gln Asp Phe Thr Leu
        915                 920                 925

Trp Ile Ser Arg Tyr Gly Asn Glu Val Glu Glu Gln Ile Lys Ile Pro
930                 935                 940

Tyr Glu Glu Ala Leu Pro Leu Ser Pro Asp Asn Val Ser Asn Cys Cys
945                 950                 955                 960

Leu Pro Ala Ser Ile Cys Cys Pro Gln Gln Ile Lys Pro His Val
                965                 970                 975

Phe Thr Tyr His Ile Asp Val Gly Glu Leu Gln Leu Glu Ala Asn Leu
            980                 985                 990

Gly Ile Glu Ile Ala Gly Lys Leu Thr Thr Arg Ser Gly Leu Ala Lys
        995                 1000                1005

Leu Gly Asn Leu Glu Ile Val Glu Glu Arg Pro Leu Thr Val Asp Glu
    1010                1015                1020

Ile Ala Asn Val Gln Arg Arg Glu Lys Lys Trp Lys Arg Ala Tyr Arg
1025                1030                1035                1040

Thr Glu Lys Gln Glu Ala Gln Leu Ala Tyr Gln Asn Met Lys Glu Val
                1045                1050                1055
```

```
Leu Ala Ser Phe Tyr Thr Thr Pro Glu Gln Thr Gln Leu Arg Asp Asn
            1060                1065                1070

Val Thr Tyr Gln Asp Ile Gln Gln Leu Ile Met Pro Ala Glu Leu Ile
        1075                1080                1085

Thr Ile His Thr Phe Ile Pro Gln Ile Leu Gln Asp Asn Gln Asn Leu
    1090                1095                1100

Val Met Gln Leu Met Gly Glu Met Gln Ala Arg Ala Leu Tyr Pro
1105                1110                1115                1120

Gln Thr Leu Leu Ile Asn Gly Asp Phe Ser Met Gly Leu Gln Gly Trp
                1125                1130                1135

Glu Gly Ser Gly Ala Thr Val Asp Val Ser His Met Gln Pro Gln Leu
            1140                1145                1150

Val Leu Ser Asn Trp Asp Ala Arg Met Thr Gln Thr Ile Thr Val Ser
        1155                1160                1165

Gln Ala Pro Val Asp Ile Glu Lys Thr Tyr Gln Leu Arg Val Thr Ala
    1170                1175                1180

Ser Gly Lys Gly Thr Val Ser Leu Ser Asp Gln Glu Asp Gln Val Thr
1185                1190                1195                1200

Leu Thr Phe His Glu Asp Ser Phe Val Thr Lys Gln Ile Val Leu Tyr
                1205                1210                1215

Ser Asn Gln Ala Leu Leu Lys Leu Val Val Gln Ser Glu Gly Ser Gln
            1220                1225                1230

Phe Thr Ile Gln Thr Ile Glu Val Phe Glu Ile
        1235                1240

<210> SEQ ID NO 16
<211> LENGTH: 671
<212> TYPE: PRT
<213> ORGANISM: Bacillus thuringiensis

<400> SEQUENCE: 16

Met Glu Gln His Ala Leu Val Pro Gln Asn Met Thr Ser Asn Thr Gly
1               5                   10                  15

Leu Ile Pro Tyr Asn Val Tyr Ala Thr Ala Pro Ser Asn Phe Ala Ser
            20                  25                  30

Phe Thr Asp Val Phe Asn Asp Leu Lys Glu Ala Tyr Asp Glu Phe Ser
        35                  40                  45

Lys Thr Gly Ala Ile Asp Val Leu Lys Gln His Leu Asn Val Ala Trp
    50                  55                  60

Asn Thr Tyr Lys Thr Asn Ser Val Asp Tyr Leu Ala Leu Ile Lys Ala
65                  70                  75                  80

Thr Ile Ser Leu Leu Gly Phe Thr Pro Ala Gly Pro Ala Val Pro Phe
                85                  90                  95

Ile Asn Met Phe Val Asp Met Val Phe Pro Met Leu Phe Gly Gly Ser
            100                 105                 110

Gly Ala Asp Lys Asn Thr Ile Phe Phe Glu Met Ile Met Asp Gln Val
        115                 120                 125

Glu Gln Leu Val Asp Gln Lys Phe Glu Ala Phe Thr Leu Asn Asn Leu
    130                 135                 140

Asn Asn Ile Ile Glu Gly Ile Glu Thr Asn Leu Val Asp Phe Gln Asn
145                 150                 155                 160

Ala Ile Gln Ile Ala Ile Cys Gln Gly Glu Gly Pro Gly Leu Arg Ser
                165                 170                 175

Asp Pro Cys Thr Pro Ser Ile Asp His Leu Gln Lys Val Tyr Thr Ala
            180                 185                 190
```

```
Phe Thr Thr Ala Arg Ser Gln Ile Gln Thr Asn Leu Pro His Phe Lys
            195                 200                 205

Asn Pro Met Asp Leu Gly Asn Thr Asn Phe Gln Ser Asp Phe Val Leu
    210                 215                 220

Leu Thr Leu Pro Leu Tyr Thr Asn Val Ala Asn Leu Asn Leu Leu Leu
225                 230                 235                 240

His His Gly Phe Ile Gln Phe Ala Glu Lys Trp Lys Ser Val Tyr Tyr
                245                 250                 255

Asp Glu Gly Thr Met Asn Gln Val Lys Ala Asp Leu Gln His Arg Ile
                260                 265                 270

Gln Glu Tyr Ser Thr Thr Val Leu Asn Thr Tyr Asn Gln Tyr Leu Pro
            275                 280                 285

Ala Val Gly Ser Ser Lys Ser Gln Thr Asn Arg Arg Ile Arg Tyr Ile
    290                 295                 300

Arg Gly Met Thr Ile Gly Ala Leu Asp Ile Ala Ser Leu Trp Pro Thr
305                 310                 315                 320

Met Asp Asn Leu Tyr Tyr Pro Met Arg Thr Asp Leu Asp Gln Thr Arg
                325                 330                 335

Leu Thr Phe Met Asp Val Val Gly Pro Ile Glu Gly Gln Asp Phe Thr
            340                 345                 350

Leu Ser Phe Pro Asn Gly Asp Met Glu Arg Tyr Gly Tyr Phe Gly Arg
    355                 360                 365

Glu Leu Thr Lys Ile Glu Pro His Tyr Arg Lys Ala Lys Ala His Asn
            370                 375                 380

Thr Gly Ala Arg Glu Tyr Asn Ile Thr Asn Gly Met Arg Asn Ser Gly
385                 390                 395                 400

Lys Asn Ala Leu Asn Gln Asp Ser Thr Asp Thr Trp Gly Pro Asn Asp
                405                 410                 415

Val Ser Tyr Ala Asp Phe Phe Asn Ser Ser Gly Tyr Leu Gln Val Phe
            420                 425                 430

Ala Pro Val Ser Phe Val Asn Met Ser Ser Gly Ser Gly Thr Tyr Tyr
    435                 440                 445

Asp Tyr Asn Lys Phe Ala Ala Leu Gly Val Asn Gly Asn Ile Val Ser
    450                 455                 460

Pro Pro Tyr Ala Asp Ser Leu Gly Asn Pro Ile Ser Ser Lys Asn Ile
465                 470                 475                 480

Pro Ile Leu Asp Gln Lys Ile Asn Tyr Leu Tyr Pro Val Thr Gly Ser
                485                 490                 495

Gly Ile Ala Glu Lys Met Gly Phe Leu Ala Ser Ile Val Gln Ala Asp
            500                 505                 510

Leu Tyr Pro Glu Asn Ile Ile Gly Thr Ile Asp Pro Ile Asp Gly Ser
    515                 520                 525

Gln Ser Ile Lys Gly Ile Pro Phe Asp Lys Cys Thr Asn Leu Gln Ile
    530                 535                 540

Ser Arg Leu Lys Glu Pro Leu Asn Gly Ala Pro Ala Val Gln Leu Ser
545                 550                 555                 560

Asn Gly Ser Ser Leu Thr Leu Ser Ile Thr Asn Met Val Ser Gln Pro
                565                 570                 575

Tyr Gln Ile Arg Ile Arg Tyr Ala Cys Pro Thr Asp Thr Thr Ile Phe
            580                 585                 590

Leu Asn Val Ala Thr Gly Gly His Ser Pro Val Tyr Gln Ser Ile Thr
    595                 600                 605

Leu Pro Ala Thr Asn Ser Gly Thr Gly His Thr Val Pro Gly Thr Asn
```

```
                    610                 615                 620
Asn Gly Met Phe Tyr Thr Val Phe Pro Thr Arg Thr Gly Thr Pro Ile
625                 630                 635                 640

Thr Ala Thr Ile Pro Ser Gly Asn Phe Asn Val Tyr Val Thr His Asn
                645                 650                 655

Asp Ser Ala Asn Leu Leu Asp Arg Ile Glu Phe Ile Pro Thr
                660                 665                 670

<210> SEQ ID NO 17
<211> LENGTH: 1277
<212> TYPE: PRT
<213> ORGANISM: Bacillus thuringiensis

<400> SEQUENCE: 17

Met Arg Arg Ser Cys Met Glu Gln Asn Asn Val Leu Ser Glu Gly Gly
1               5                   10                  15

Ala Gln Ser Met Ser Val Ser Ser Val Glu Ser Pro Leu Ile Pro Tyr
                20                  25                  30

Asn Val Tyr Ala Thr Ala Pro Ser Pro Leu Pro Ser Asn Leu Ala Ser
                35                  40                  45

Phe Asn Asp Ile Phe Asn Asp Leu Lys Gly Ala Tyr Asp Glu Phe Ser
            50                  55                  60

Lys Thr Gly Ala Ile Asp Val Leu Lys Gln His Leu Asn Val Ala Trp
65              70                  75                  80

Gly Ala Tyr Lys Asn Ser Ala Val Asp Tyr Leu Ala Leu Ile Lys Ala
                85                  90                  95

Thr Ile Ser Leu Leu Gly Phe Thr Pro Ala Gly Pro Ala Val Pro Phe
                100                 105                 110

Ile Asn Met Phe Val Asp Met Ile Phe Pro Val Leu Phe Gly Gly Thr
                115                 120                 125

Thr Gln Asp Lys Asn Lys Ile Phe Phe Asp Met Ile Met Glu Gln Val
                130                 135                 140

Glu Gln Leu Val Asp Gln Lys Phe Gln Asn Phe Thr Ile Asn Asn Leu
145                 150                 155                 160

Asn Asn Ile Ile Asp Gly Ile Gln Thr Val Leu Val Asp Phe Gln Asn
                165                 170                 175

Ala Ile Gln Val Ala Ile Cys Gln Gly Glu Ser Pro Gly Leu Arg Ser
                180                 185                 190

Asp Pro Cys Thr Pro Ser Ala Ala His Leu Glu Gln Val His Val Ala
                195                 200                 205

Phe Thr Thr Ala Arg Ala Thr Ile Gln Thr Gln Leu Pro His Phe Lys
                210                 215                 220

Asn Pro Met Asp Leu Gly Asn Pro Asn Phe Gln Ser Asp Phe Val Leu
225                 230                 235                 240

Leu Thr Leu Pro Leu Tyr Thr His Ala Ala Asn Leu Asn Leu Leu Leu
                245                 250                 255

His His Gly Tyr Ile Gln Phe Arg Glu Lys Trp Lys Ser Val Ser Tyr
                260                 265                 270

Asp Glu Gly Thr Met Asn Gln Ile Lys Ala Asp Leu Gln His Arg Ile
                275                 280                 285

Gln Glu Tyr Ser Gly Thr Val Leu Ser Thr Tyr Thr Gln Tyr Leu Pro
                290                 295                 300

Ser Val Gly Ala Ser Lys Ser Gln Thr Asn Arg Arg Ile Arg Tyr Ile
305                 310                 315                 320

Arg Gly Met Thr Ile Gly Ala Leu Asp Ile Ala Ala Leu Trp Pro Thr
```

```
                    325                 330                 335
Met Asp Ala Val His Tyr Pro Ile Arg Thr Asp Leu Asp Gln Thr Arg
                340                 345                 350

Leu Ala Phe Leu Asp Val Val Gly Pro Ile Glu Asn Arg Asp Phe Asn
                355                 360                 365

Leu Ser Phe Leu Asn Gly Asp Met Glu Gly Tyr Asn Tyr Phe Ser Arg
    370                 375                 380

Glu Leu Thr Lys Ile Thr Pro His Tyr Arg Thr Ala Lys Gly Pro Asn
385                 390                 395                 400

Val Gly Asp Arg Asn Tyr Gly Leu Thr Asn Gly Met Arg Asn Tyr Gly
                405                 410                 415

Thr Asp Ala Ser Asp His Gln Gln Ile Asp Thr Ser Gly Pro Ser Asp
                420                 425                 430

Glu Tyr His Asn Asn Phe Tyr Asn Thr Ala Gly Tyr Ala Glu Val Asp
                435                 440                 445

Ala Pro Ile Ser Tyr Val Asn Met Trp Ser Asp Ala Ala Leu Tyr Tyr
                450                 455                 460

Asp Tyr Asn Lys Phe Gly Ala Thr Asn Ala Asn Gly Asp Val Val Val
465                 470                 475                 480

Pro Pro Asn Thr Asp Ala Ile Gly Asn Pro Val Tyr Ser Lys Asn Ile
                485                 490                 495

Pro Ile Leu Asn Gln Lys Ile Asn Tyr Met Tyr Pro Val Thr Gly Ala
                500                 505                 510

Gly Ile Ser Glu Lys Met Gly Phe Leu Ala Ser Leu Val Pro Tyr Asp
                515                 520                 525

Leu Phe Pro Glu Asn Leu Ile Gly Gln Ile Asp Pro Ile Asp Gly Ser
                530                 535                 540

Gln Ser Ile Lys Gly Ile Pro Phe Glu Lys Ser Thr Pro Leu Thr Val
545                 550                 555                 560

Pro Arg Lys Lys Glu Pro Ile Asn Gly Ala Ser Ala Val Gln Leu Pro
                565                 570                 575

Lys Asn Gln Tyr Val Asn Met Ala Leu Thr Asn Gly Thr Ser Gly Asp
                580                 585                 590

Tyr Glu Ile Arg Ile Arg Tyr Ala Ser Asp Thr Ala Val Thr Ile Thr
                595                 600                 605

Leu Asn Val Thr Ala Gly Ser Thr Thr Ile Ile Asn Asn Gln Ala Ile
                610                 615                 620

Thr Leu Pro Ala Thr Thr Gly Leu Gln Ala Ser Val Pro Gly Ile Asn
625                 630                 635                 640

Gly Ser Tyr Ala Leu Asn Pro Ser Asp Ser Ser Leu Lys Thr Arg Ile
                645                 650                 655

Pro Val Gly Asn Phe His Val Tyr Val Thr Asn Asn Thr Gly Asp Asn
                660                 665                 670

Leu Phe Leu Asp Arg Ile Glu Phe Ala Pro Leu Ala Ser Ser Gly Pro
                675                 680                 685

Ile Ile Ile Pro Asn Thr Pro Ile Lys Thr Tyr Thr Asn Pro Pro Asn
                690                 695                 700

Pro Gln Gln Val Leu Trp Thr Ala Arg Ser Ser Val Leu Gly Asp Ile
705                 710                 715                 720

Val Asn Leu Ser Gly Tyr Thr Asn Gly Ala Asn Gly Tyr Tyr Thr Gly
                725                 730                 735

Val Met Pro Ala Ile Arg Ile Gln Phe Phe Arg Asn Asn Gln Leu Val
                740                 745                 750
```

```
Asp His Tyr Asp Thr Ser Glu Gly Arg Tyr Pro His Asn Ala Asp Phe
        755                 760                 765

Asn Ile Ser Asn Tyr Lys Ile Thr Gly Gly Phe Asp Lys Ile Val Leu
770                 775                 780

Ile Pro Leu His Gln Tyr Tyr Thr Glu Pro Val Glu Gly Gln Ile Asn
785                 790                 795                 800

Gly Thr Ile Thr Met Asn Gln Asn Lys Phe Thr Thr Glu Glu Glu Leu
                805                 810                 815

Ser Ala Val Thr Gln Val Val Asn Ala Leu Phe Ile Thr Asp Thr Gln
                820                 825                 830

Leu Ala Pro Thr Val Thr Asp Tyr Trp Ile Asp Gln Val Tyr Leu Lys
                835                 840                 845

Val Asn Ala Leu Ser Asp Glu Trp Phe Glu Glu Lys Ala Gln Leu
850                 855                 860

Arg Met Lys Ile Asn Arg Ala Lys Gln Leu Arg Met Met Gln Asn Leu
865                 870                 875                 880

Leu Val Gly Gly Asp Phe Ser Thr Leu Thr Gln Trp Gln Lys Ser Pro
                885                 890                 895

His Ala Arg Val Val Ala Asn Ser Asp Leu Phe Val Asp Lys His Leu
                900                 905                 910

Leu Leu Gln Pro Ser Met Tyr Pro Met Ile Ala Pro Ser Phe Val Tyr
                915                 920                 925

Gln Lys Val Glu Glu Arg Lys Leu Lys Pro Tyr Thr Arg Tyr Thr Val
                930                 935                 940

Thr Gly Phe Val Ala Gln Ala Gln Lys Leu Glu Ile Trp Val Ser Arg
945                 950                 955                 960

Tyr Gly Asn Glu Val Lys Glu Arg Ile Glu Ile Pro Tyr Glu Glu Met
                965                 970                 975

Leu Pro Leu Ser Pro Asp Ala Gln Ser Asn Cys Cys Leu Pro Ala Pro
                980                 985                 990

Val Ser Cys Thr Gly Gln Gln Thr Ser Pro His Val Phe Thr Tyr His
                995                 1000                1005

Ile Asp Val Gly Glu Leu Gln Pro Glu Ala Asn Leu Gly Ile Glu Leu
        1010                1015                1020

Ala Phe Lys Leu Thr Ala Arg Ser Gly Val Ala Thr Ile Gly Asn Val
1025                1030                1035                1040

Glu Ile Val Glu Glu Arg Pro Leu Thr Ala Ala Glu Thr Gln Lys Ile
                1045                1050                1055

Gln Gln Arg Glu Arg Lys Trp Lys Arg Thr Tyr Gln Lys Met His Gln
                1060                1065                1070

Glu Ala Gln Thr Met Tyr Gln Glu Thr Met Asp Glu Leu Ala Ser Leu
                1075                1080                1085

Tyr Thr Thr Pro Glu Gln Thr Gln Leu Gln Ala Asn Val Thr Tyr Gln
                1090                1095                1100

Asp Ile Gln Asn Ile Glu Ile Pro Ile Ala Leu Leu Gly Ala His Ala
1105                1110                1115                1120

Phe Ile Pro Gln Ile Ser Ser Gly Tyr Asp Asp Leu Phe Ala Gln Leu
                1125                1130                1135

Ser Ile Lys Lys Asp Asn Ala Leu Tyr Leu Tyr Pro Gln Thr Leu Leu
                1140                1145                1150

Val Asn Gly Asp Phe Ser Arg Gly Leu Ala Gly Trp Asn Gly Thr Gly
                1155                1160                1165

Ala Gln Val Ala Met Thr Glu Gly Gln Pro Met Leu Val Leu Thr Asn
                1170                1175                1180
```

-continued

```
Trp Asp Ala Arg Leu Thr Gln Ser Met Leu Pro Gln Thr Asp Ser
1185                1190                1195                1200

Gly Thr Glu Lys Ala Tyr Gln Leu Arg Val Thr Ala Ser Gly Lys Gly
            1205                1210                1215

Thr Val Ala Leu Ser Asp Thr Glu Asn Gln Val Lys Leu Thr Phe Asp
        1220                1225                1230

Gly Asp Thr Phe Val Thr Lys Gln Ile Ile Leu Tyr Pro Glu His Ser
        1235                1240                1245

Met Leu Glu Leu Ala Val Gln Ser Asp Gly Ser Gln Phe Ile Ile Glu
        1250                1255                1260

Ser Ile Glu Val Phe Glu Ser Pro Ile Pro Leu Val Asp
1265                1270                1275
```

<210> SEQ ID NO 18
<211> LENGTH: 683
<212> TYPE: PRT
<213> ORGANISM: Bacillus thuringiensis

<400> SEQUENCE: 18

```
Met Arg Arg Ser Cys Met Glu Gln Asn Asn Val Leu Ser Glu Glu Gly
 1               5                  10                  15

Ala Gln Ser Met Ser Val Ser Ser Val Glu Ser Pro Leu Ile Pro Tyr
            20                  25                  30

Asn Val Tyr Ala Thr Ala Pro Ser Pro Leu Pro Ser Asn Leu Ala Ser
        35                  40                  45

Phe Asn Asp Ile Phe Asn Asp Leu Lys Gly Ala Tyr Asp Glu Phe Ser
    50                  55                  60

Lys Thr Gly Ala Ile Asp Val Leu Lys Gln His Leu Asn Val Ala Trp
65                  70                  75                  80

Gly Ala Tyr Lys Asn Ser Ala Val Asp Tyr Leu Ala Leu Ile Lys Ala
                85                  90                  95

Thr Ile Ser Leu Leu Gly Phe Thr Pro Ala Gly Pro Ala Val Pro Phe
            100                 105                 110

Ile Asn Met Phe Val Asp Met Ile Phe Pro Val Leu Phe Gly Gly Thr
        115                 120                 125

Thr Gln Asp Lys Asn Lys Ile Phe Phe Asp Met Ile Met Glu Gln Val
    130                 135                 140

Glu Gln Leu Val Asp Gln Lys Phe Gln Asn Phe Thr Ile Asn Asn Leu
145                 150                 155                 160

Asn Asn Ile Ile Asp Gly Ile Gln Thr Val Leu Val Asp Phe Gln Asn
                165                 170                 175

Ala Ile Gln Val Ala Ile Cys Gln Gly Glu Ser Pro Gly Leu Arg Ser
            180                 185                 190

Asp Pro Cys Thr Pro Ser Ala Ala His Leu Glu Gln Val His Val Ala
        195                 200                 205

Phe Thr Thr Ala Arg Ala Thr Ile Gln Thr Gln Leu Pro His Phe Lys
    210                 215                 220

Asn Pro Met Asp Leu Gly Asn Pro Asn Phe Gln Ser Asp Phe Val Leu
225                 230                 235                 240

Leu Thr Leu Pro Leu Tyr Thr His Ala Ala Asn Leu Asn Leu Leu
                245                 250                 255

His His Gly Tyr Ile Gln Phe Arg Glu Lys Trp Lys Ser Val Ser Tyr
            260                 265                 270

Asp Glu Gly Thr Met Asn Gln Ile Lys Ala Asp Leu Gln His Arg Ile
        275                 280                 285
```

```
Gln Glu Tyr Ser Gly Thr Val Leu Ser Thr Tyr Thr Gln Tyr Leu Pro
    290                 295                 300

Ser Val Gly Ala Ser Lys Ser Gln Thr Asn Arg Arg Ile Arg Tyr Ile
305                 310                 315                 320

Arg Gly Met Thr Ile Gly Ala Leu Asp Ile Ala Ala Leu Trp Pro Thr
                325                 330                 335

Met Asp Ala Val His Tyr Pro Ile Arg Thr Asp Leu Asp Gln Thr Arg
            340                 345                 350

Leu Ala Phe Leu Asp Val Val Gly Pro Ile Glu Asn Arg Asp Phe Asn
        355                 360                 365

Leu Ser Phe Leu Asn Gly Asp Met Glu Gly Tyr Asn Tyr Phe Ser Arg
370                 375                 380

Glu Leu Thr Lys Ile Thr Pro His Tyr Arg Thr Ala Lys Gly Pro Asn
385                 390                 395                 400

Val Gly Asp Arg Asn Tyr Gly Leu Thr Asn Gly Met Arg Asn Tyr Gly
                405                 410                 415

Thr Asp Ala Ser Asp His Gln Gln Ile Asp Thr Ser Gly Pro Ser Asp
            420                 425                 430

Glu Tyr His Asn Asn Phe Tyr Asn Thr Ala Gly Tyr Ala Glu Val Asp
        435                 440                 445

Ala Pro Ile Ser Tyr Val Asn Met Trp Ser Ala Ala Leu Tyr Tyr
450                 455                 460

Asp Tyr Asn Lys Phe Gly Ala Thr Asn Ala Asn Gly Asp Val Val Val
465                 470                 475                 480

Pro Pro Asn Thr Asp Ala Ile Gly Asn Pro Val Tyr Ser Lys Asn Ile
                485                 490                 495

Pro Ile Leu Asn Gln Lys Ile Asn Tyr Met Tyr Pro Val Thr Gly Ala
            500                 505                 510

Gly Ile Ser Glu Lys Met Gly Phe Leu Ala Ser Leu Val Pro Tyr Asp
        515                 520                 525

Leu Phe Pro Glu Asn Leu Ile Gly Gln Ile Asp Pro Ile Asp Gly Ser
530                 535                 540

Gln Ser Ile Lys Gly Ile Pro Phe Glu Lys Ser Thr Pro Leu Thr Val
545                 550                 555                 560

Pro Arg Lys Lys Glu Pro Ile Asn Gly Ala Ser Ala Val Gln Leu Pro
                565                 570                 575

Lys Asn Gln Tyr Val Asn Met Ala Leu Thr Asn Gly Thr Ser Gly Asp
            580                 585                 590

Tyr Glu Ile Arg Ile Arg Tyr Ala Ser Asp Thr Ala Val Thr Ile Thr
        595                 600                 605

Leu Asn Val Thr Ala Gly Ser Thr Thr Ile Ile Asn Asn Gln Ala Ile
610                 615                 620

Thr Leu Pro Ala Thr Thr Gly Leu Gln Ala Ser Val Pro Gly Ile Asn
625                 630                 635                 640

Gly Ser Tyr Ala Leu Asn Pro Ser Asp Ser Ser Leu Lys Thr Arg Ile
                645                 650                 655

Pro Val Gly Asn Phe His Val Tyr Val Thr Asn Asn Thr Gly Asp Asn
            660                 665                 670

Leu Phe Leu Asp Arg Ile Glu Phe Ala Pro Leu
        675                 680

<210> SEQ ID NO 19
<211> LENGTH: 1301
<212> TYPE: PRT
```

<213> ORGANISM: Bacillus thuringiensis

<400> SEQUENCE: 19

```
Met Asn Gln Asn Tyr Asn Asn Glu Tyr Glu Ile Lys Asp Thr Asp
1               5                   10                  15

Thr Met Gly Tyr Gln Ser Arg Tyr Pro Leu Ala Asn Thr Pro Gly Ala
            20                  25                  30

Glu Leu Gln Gln Met Asn Tyr Lys Asp Trp Met Asp Arg Cys Thr Asn
        35                  40                  45

Gly Glu Ser Ile Asp Val Phe Gly Asp Thr Ala Gly Ala Val Arg Asn
50                  55                  60

Thr Leu Ile Ile Gly Thr Gly Val Ala Trp Ala Leu Leu Gly Leu Ile
65                  70                  75                  80

Pro Val Val Gly Gly Pro Ala Ser Ala Ile Ala Gly Leu Phe Asn Val
                85                  90                  95

Leu Leu Pro Tyr Trp Trp Pro Glu Gln Ala Gly Pro Pro Gly Thr Pro
            100                 105                 110

Gln Ala Gln Tyr Thr Trp Lys Gln Leu Met Ala Gly Ala Glu Asp Ile
        115                 120                 125

Thr Asn Lys Lys Ile Gln Glu Ser Ala Lys Ser Tyr Ala Thr Ala Gln
130                 135                 140

Trp Gln Arg Val Gln Thr Tyr Gln Ala Asp Phe Thr Gln Ala Arg Cys
145                 150                 155                 160

Asp Trp Ile Gln Asp Gln Asn Asn Glu Ile Lys Lys Ser Arg Leu Gln
                165                 170                 175

Asp Ala Phe Asp Asp Phe Asn Asp Glu Leu Gln Gly Ser Met Pro Phe
            180                 185                 190

Phe Arg Val Gln Gly Phe Glu Val Gln Met Leu Ser Met Tyr Ala Gln
        195                 200                 205

Ala Ala Asn Met His Leu Leu Leu Leu Arg Asp Val Val Gln Asn Gly
210                 215                 220

Leu Ser Trp Gly Phe Leu Gln Ser Glu Val Asp Arg Tyr Tyr Leu Asn
225                 230                 235                 240

Leu Asn Pro Gln Gly Asn Gly Leu Leu Gln Leu Gly Thr Tyr
                245                 250                 255

Thr Asn Tyr Cys Ile Asp Trp Tyr Asn Lys Gly Leu Gln Glu Gln Tyr
            260                 265                 270

Ala Thr Gly Tyr Trp Ser Lys Phe Asn Asn Phe Arg Ile Thr Met Thr
        275                 280                 285

Ile Thr Val Leu Asp Thr Val Ser Val Trp Pro Thr Phe Asp Pro Lys
290                 295                 300

His Tyr Ala Leu Pro Thr Lys Ser Gln Leu Thr Arg Met Val Tyr Thr
305                 310                 315                 320

Pro Lys Val Gly Glu Thr Ala Ala Ser Phe Lys Pro Ser Gln Pro Ile
                325                 330                 335

Asn Val Ile Glu Asn Ser Ile Val Ala Ser Pro Arg Leu Phe Ala Trp
            340                 345                 350

Leu Ile Glu Val Glu Met Val Asn Asn Gln Tyr Asn Tyr Val Gln Tyr
        355                 360                 365

Tyr Lys Gln Thr Phe Gln Asn Thr Leu Arg Asp Thr Gln Trp Ser Ile
370                 375                 380

Ser Lys Gly Thr Thr Ser Gly Gly Ile Ser Thr Asn Thr Leu Thr Ile
385                 390                 395                 400

Pro Ser Pro Gln Ser Gln Asp Asp Val Trp Lys Ile Lys Asn Tyr Phe
```

```
                405                 410                 415
Arg Asp Asp Thr Gly Asn Gly Ser His Asp Asp Lys Thr Val Thr Gly
            420                 425                 430

Trp Thr Tyr Ser Phe Thr Lys Ser Leu Asp Gln Thr Phe Phe Ile Gly
            435                 440                 445

Asn Arg Gly Tyr Ser Ile Thr Arg Leu Leu Gly Leu Pro Cys Arg Gly
450                 455                 460

Asn Asp Ser Gly Ile Cys Asp Pro Cys Asp Phe Glu Asn Pro Cys Glu
465                 470                 475                 480

Asn Glu Leu Pro Asn Thr Thr Met Pro Cys Glu Asp Lys Gln Leu Tyr
                485                 490                 495

Ser His Arg Leu Ser Tyr Leu Gly Ala Gly Glu Arg Asn Tyr Tyr Asp
            500                 505                 510

Ala Pro Pro Ala Leu Thr Tyr Phe Gly Tyr Gly Trp Thr His Val Ser
            515                 520                 525

Ala Asp Ala His Asn Leu Val Asp Val Lys Lys Ile Thr Gln Ile Pro
            530                 535                 540

Ala Val Lys Gly Ser Ser Ile Ser Gly Asp Ala Arg Val Val Lys Gly
545                 550                 555                 560

Ser Gly Ser Thr Gly Gly Asp Leu Ile Lys Leu Ser Ala Gly Gly Ser
                565                 570                 575

Val Thr Val Lys Val Thr Met Pro Ile Ser Val Ser Lys Gln Thr Gln
            580                 585                 590

Trp Tyr Gln Ile Arg Met Arg Tyr Ala Asn Asp Glu Thr Asn Leu Leu
            595                 600                 605

Arg Leu Val Val Lys Ser Asp Phe Glu Glu Trp Ser Arg Val Gln Gln
    610                 615                 620

Leu Pro Gly Thr Tyr Leu Gly Glu Glu Leu Ile Phe Gln Ser Phe Ala
625                 630                 635                 640

Tyr Arg Asn Leu Val Asp Gly Ile Ala Thr Tyr Glu Glu Lys Tyr Ile
                645                 650                 655

Leu Glu Leu Thr Leu Glu Asn Leu Gly Asn Pro Asn Asp Ile Asp Ile
            660                 665                 670

Asn Thr Asn Leu Leu Ile Asp Lys Ile Glu Phe Ile Pro Ile Glu Gly
            675                 680                 685

Ser Val Gly Glu Tyr Lys Ala Asn Gln Ala Val Glu Glu Ala Arg Lys
    690                 695                 700

Val Val Asn Ala Leu Phe Thr Gly Ala Ala Lys Asn Ala Leu Lys Leu
705                 710                 715                 720

Asn Val Thr Asp Tyr Ala Val Asp Gln Ala Ser Asn Leu Val Glu Cys
                725                 730                 735

Val Ser Asp Glu Phe His Ala Gln Glu Lys Met Ile Leu Leu Asp Gln
            740                 745                 750

Val Lys Phe Ala Lys Arg Leu Ser Gln Thr Arg Asn Leu Leu His Tyr
            755                 760                 765

Gly Asp Phe Glu Ser Ser Asn Trp Ser Gly Glu Asn Gly Trp Lys Thr
    770                 775                 780

Ser His His Val His Val Thr Ala Asn Asn Pro Ile Phe Lys Gly Arg
785                 790                 795                 800

Tyr Leu His Met Pro Gly Ala Thr Ser Ser Gln Phe Ser Asn Thr Val
                805                 810                 815

Tyr Pro Thr Tyr Ile Tyr Gln Lys Val Asp Glu Ser Lys Leu Lys Ser
            820                 825                 830
```

```
Tyr Thr Arg Tyr Leu Val Arg Gly Phe Val Gly Asn Ser Lys Asp Leu
        835                 840                 845

Glu Leu Leu Val Glu Arg Tyr Gly Lys Asp Val His Val Glu Met Asp
    850                 855                 860

Val Pro Asn Asp Ile Arg Tyr Ser Leu Pro Met Asn Glu Cys Gly Gly
865                 870                 875                 880

Phe Asp Arg Cys Lys Ser Ala Ser Asp Gln Thr Arg Thr Pro His Thr
                885                 890                 895

Cys Thr Cys Lys Asp Thr Thr Ser Met His Thr Asp Cys Gln Cys Gln
                900                 905                 910

Asn Lys Val Asn Arg Thr Ser Ala Asp Met Tyr Thr Asn Gly Ser Pro
            915                 920                 925

Ser Ser Val Met Tyr Ala Asp Gly Phe His Ala His Lys Ser Cys Gly
    930                 935                 940

Cys Lys Asn Asn Asp Arg Tyr Gln Asn Gly Thr His Pro Gln Lys Ser
945                 950                 955                 960

Cys Glu Cys Lys Asp Pro His Val Phe Ser Tyr His Ile Asp Thr Gly
                965                 970                 975

Cys Val Asp Gln Glu Glu Asn Leu Gly Leu Trp Phe Ala Leu Lys Val
            980                 985                 990

Ala Ser Glu Asn Gly Val Ala Asn Ile Asp Asn Leu Glu Ile Ile Glu
    995                 1000                1005

Ala Gln Pro Leu Thr Gly Glu Ala Leu Ala Arg Val Lys Lys Arg Glu
    1010                1015                1020

Gln Lys Trp Lys Gln Glu Met Ala Gln Lys Arg Leu Gln Thr Asp Lys
1025                1030                1035                1040

Ala Val Gln Ala Ala Gln Gly Ala Ile Gln Pro Leu Phe Thr Asn Ala
                1045                1050                1055

Gln Tyr Asn Arg Leu Gln Phe Glu Thr Leu Phe Pro Gln Ile Val Asn
                1060                1065                1070

Ala Glu Met Leu Val Gln Gln Ile Pro Tyr Met Tyr His Pro Phe Leu
            1075                1080                1085

Ser Gly Ala Leu Pro Thr Val Pro Gly Met Asn Phe Glu Ile Ile Gln
    1090                1095                1100

Arg Leu Leu Ala Leu Thr Gly Asn Ala Arg Gly Leu Tyr Glu Gln Arg
1105                1110                1115                1120

Asn Leu Val Arg Asn Gly Thr Phe Ser Ser Gly Thr Gly Asn Trp His
                1125                1130                1135

Val Thr Glu Gly Val Lys Val Gln Pro Leu Gln Asn Thr Ser Val Leu
            1140                1145                1150

Val Leu Ser Glu Trp Asn Gln Glu Ala Ser Gln Leu His Ile Asp
            1155                1160                1165

Pro Asp Arg Gly Tyr Val Leu Arg Val Thr Ala Arg Lys Glu Gly Gly
    1170                1175                1180

Gly Lys Gly Thr Val Thr Met Ser Asp Cys Ala Ala Tyr Thr Glu Thr
1185                1190                1195                1200

Leu Thr Phe Thr Ser Cys Asp Phe Asn Thr Phe Gly Ser Gln Thr Met
                1205                1210                1215

Thr Ser Gly Thr Leu Ser Gly Phe Val Thr Lys Thr Leu Glu Ile Phe
                1220                1225                1230

Pro Asp Thr Asp Arg Ile Arg Ile Asp Met Gly Glu Thr Glu Gly Thr
            1235                1240                1245

Phe Gln Ile Glu Ser Val Glu Leu Ile Cys Met Glu Gln Met Glu Asp
            1250                1255                1260
```

Asp Leu Tyr Asp Met Ala Gly Asn Leu Glu Glu Met Leu Asp Leu
1265                1270                1275                1280

Gly Ile Glu Asn Ile Asn Ala Val Thr Asn Lys Met Cys Phe Ser Trp
                1285                1290                1295

Asp Ile Gln Cys Pro
            1300

<210> SEQ ID NO 20
<211> LENGTH: 686
<212> TYPE: PRT
<213> ORGANISM: Bacillus thuringiensis

<400> SEQUENCE: 20

Met Asn Gln Asn Tyr Asn Asn Glu Tyr Glu Ile Lys Asp Thr Asp
  1               5                  10                 15

Thr Met Gly Tyr Gln Ser Arg Tyr Pro Leu Ala Asn Thr Pro Gly Ala
             20                  25                  30

Glu Leu Gln Gln Met Asn Tyr Lys Asp Trp Met Asp Arg Cys Thr Asn
         35                  40                  45

Gly Glu Ser Ile Asp Val Phe Gly Asp Thr Ala Gly Ala Val Arg Asn
     50                  55                  60

Thr Leu Ile Ile Gly Thr Gly Val Ala Trp Ala Leu Leu Gly Leu Ile
65                  70                  75                  80

Pro Val Val Gly Gly Pro Ala Ser Ala Ile Ala Gly Leu Phe Asn Val
                 85                  90                  95

Leu Leu Pro Tyr Trp Trp Pro Glu Gln Ala Gly Pro Pro Gly Thr Pro
            100                 105                 110

Gln Ala Gln Tyr Thr Trp Lys Gln Leu Met Ala Gly Ala Glu Asp Ile
        115                 120                 125

Thr Asn Lys Lys Ile Gln Glu Ser Ala Lys Ser Tyr Ala Thr Ala Gln
130                 135                 140

Trp Gln Arg Val Gln Thr Tyr Gln Ala Asp Phe Thr Gln Ala Arg Cys
145                 150                 155                 160

Asp Trp Ile Gln Asp Gln Asn Asn Glu Ile Lys Lys Ser Arg Leu Gln
                165                 170                 175

Asp Ala Phe Asp Asp Phe Asn Asp Glu Leu Gln Gly Ser Met Pro Phe
            180                 185                 190

Phe Arg Val Gln Gly Phe Glu Val Gln Met Leu Ser Met Tyr Ala Gln
        195                 200                 205

Ala Ala Asn Met His Leu Leu Leu Arg Asp Val Val Gln Asn Gly
210                 215                 220

Leu Ser Trp Gly Phe Leu Gln Ser Glu Val Asp Arg Tyr Tyr Leu Asn
225                 230                 235                 240

Leu Asn Pro Gln Gly Asn Gln Gly Leu Leu Gln Leu Gly Thr Tyr
                245                 250                 255

Thr Asn Tyr Cys Ile Asp Trp Tyr Asn Lys Gly Leu Gln Glu Gln Tyr
            260                 265                 270

Ala Thr Gly Tyr Trp Ser Lys Phe Asn Asn Phe Arg Ile Thr Met Thr
        275                 280                 285

Ile Thr Val Leu Asp Thr Val Ser Val Trp Pro Thr Phe Asp Pro Lys
290                 295                 300

His Tyr Ala Leu Pro Thr Lys Ser Gln Leu Thr Arg Met Val Tyr Thr
305                 310                 315                 320

Pro Lys Val Gly Glu Thr Ala Ala Ser Phe Lys Pro Ser Gln Pro Ile
                325                 330                 335

```
Asn Val Ile Glu Asn Ser Ile Val Ala Ser Pro Arg Leu Phe Ala Trp
            340                 345                 350

Leu Ile Glu Val Glu Met Val Asn Asn Gln Tyr Asn Tyr Val Gln Tyr
            355                 360                 365

Tyr Lys Gln Thr Phe Gln Asn Thr Leu Arg Asp Thr Gln Trp Ser Ile
        370                 375                 380

Ser Lys Gly Thr Thr Ser Gly Gly Ile Ser Thr Asn Thr Leu Thr Ile
385                 390                 395                 400

Pro Ser Pro Gln Ser Gln Asp Asp Val Trp Lys Ile Lys Asn Tyr Phe
                405                 410                 415

Arg Asp Asp Thr Gly Asn Gly Ser His Asp Asp Lys Thr Val Thr Gly
                420                 425                 430

Trp Thr Tyr Ser Phe Thr Lys Ser Leu Asp Gln Thr Phe Phe Ile Gly
            435                 440                 445

Asn Arg Gly Tyr Ser Ile Thr Arg Leu Leu Gly Leu Pro Cys Arg Gly
        450                 455                 460

Asn Asp Ser Gly Ile Cys Asp Pro Cys Asp Phe Glu Asn Pro Cys Glu
465                 470                 475                 480

Asn Glu Leu Pro Asn Thr Thr Met Pro Cys Glu Asp Lys Gln Leu Tyr
                485                 490                 495

Ser His Arg Leu Ser Tyr Leu Gly Ala Gly Glu Arg Asn Tyr Tyr Asp
            500                 505                 510

Ala Pro Pro Ala Leu Thr Tyr Phe Gly Tyr Gly Trp Thr His Val Ser
        515                 520                 525

Ala Asp Ala His Asn Leu Val Asp Val Lys Lys Ile Thr Gln Ile Pro
530                 535                 540

Ala Val Lys Gly Ser Ser Ile Ser Gly Asp Ala Arg Val Val Lys Gly
545                 550                 555                 560

Ser Gly Ser Thr Gly Gly Asp Leu Ile Lys Leu Ser Ala Gly Gly Ser
                565                 570                 575

Val Thr Val Lys Val Thr Met Pro Ile Ser Val Ser Lys Gln Thr Gln
            580                 585                 590

Trp Tyr Gln Ile Arg Met Arg Tyr Ala Asn Asp Glu Thr Asn Leu Leu
        595                 600                 605

Arg Leu Val Val Lys Ser Asp Phe Glu Glu Trp Ser Arg Val Gln Gln
610                 615                 620

Leu Pro Gly Thr Tyr Leu Gly Glu Glu Leu Ile Phe Gln Ser Phe Ala
625                 630                 635                 640

Tyr Arg Asn Leu Val Asp Gly Ile Ala Thr Tyr Glu Glu Lys Tyr Ile
                645                 650                 655

Leu Glu Leu Thr Leu Glu Asn Leu Gly Asn Pro Asn Asp Ile Asp Ile
            660                 665                 670

Asn Thr Asn Leu Leu Ile Asp Lys Ile Glu Phe Ile Pro Ile
        675                 680                 685

<210> SEQ ID NO 21
<211> LENGTH: 1329
<212> TYPE: PRT
<213> ORGANISM: Bacillus thuringiensis

<400> SEQUENCE: 21

Met Glu Ile Thr Ser Glu Ile Tyr Pro Ile Ala Tyr Asn Val Leu Ala
1               5                   10                  15

Asn Pro Pro Thr Leu Asp Thr Glu Asp Gln Gln Asn Pro Trp Asp Ala
            20                  25                  30
```

```
Tyr Val Asn Trp Arg Lys Gln Leu Asn Asp Thr Trp Leu Thr Tyr Asp
         35                  40                  45

Gln Asn Phe Leu Pro Asp Pro Val Met Ala Ile Ile Asn Asp Met Ala
 50                  55                  60

Asn Ala Tyr Ala Gly Lys Pro Gly Ser Tyr Val Ala Leu Ala Gln Glu
 65                  70                  75                  80

Gly Ile Arg Ile Ala Phe Leu Phe Leu Pro Gly Gly Gln Thr Ala Ala
                 85                  90                  95

Phe Ala Ile Asn Lys Val Ile Gly Leu Phe Phe Pro Thr His Gln Pro
                100                 105                 110

Ser Leu Phe Asp Gln Ile Lys Asp Leu Val Glu Gln Met Ile Asp Gln
             115                 120                 125

Lys Phe Val Glu Gln Glu Ile Asn Ser Asn Ile Asn Gln Leu Asn Gly
         130                 135                 140

Leu Ile Thr Gln Leu Gly Gln Phe Ser Asn Ser Met Gln Gln Ala Met
145                 150                 155                 160

Gly Lys Pro Met Asn Phe Pro Val Thr His Ser Ser Ala Thr Thr
                 165                 170                 175

Asn Ser Phe Val Asp Thr Asn Glu Leu Asp Ser Tyr Asp Cys Ser Gln
             180                 185                 190

Asp Pro Asp Cys Ser Cys Ser Glu Asp Pro Asn Arg Thr Ser Asn Ser
         195                 200                 205

Pro Val Cys Thr Pro Cys Thr Cys Arg Ile Lys Gly Val Gln Asp Glu
         210                 215                 220

Phe Ile Ala Thr Arg Lys Val Ile Leu Asp Ile Leu Thr Ser Met Lys
225                 230                 235                 240

Thr Ser Leu Thr Asn Val Leu Thr Thr Glu His Ala Thr Thr Tyr Met
                 245                 250                 255

Gln Ile Phe Leu Pro Ile Tyr Thr Thr Ala Val Thr Leu Tyr Phe Gly
             260                 265                 270

Met Tyr Lys Ser Tyr Ile Glu Phe Ala Thr Gln Tyr Gly Phe Glu Ile
         275                 280                 285

Gly Val Asn Gly Asn Thr Met Lys Tyr Ala Asn Glu Leu Gln Gln Tyr
         290                 295                 300

Ile Ser Ala Glu Ser Ala Tyr Val Tyr Asn Glu Phe Ala Met Tyr Leu
305                 310                 315                 320

Pro Asn Ser Lys Asn Leu Thr Lys Gly Asp Leu Asn Lys Tyr Ile Gln
                 325                 330                 335

Tyr Ser Arg Thr Ile Thr Leu Asn Ala Leu Asp Thr Leu Ser Thr Trp
             340                 345                 350

Pro Leu Tyr Asn Val Leu Asp Tyr Pro Ile Ser Thr Thr Leu Asn Gln
         355                 360                 365

Thr Arg Leu Val Phe Asn Asp Ile Ile Gly Pro Val Glu Cys Arg Thr
         370                 375                 380

Gly Gly Gln Asn Ser Asp Asn Leu Ser Phe Asn Thr Leu Tyr Asp Tyr
385                 390                 395                 400

Ser Gly Asn Asn Leu Leu Asn Asn Asp Ile Thr Asn Tyr Phe Tyr Glu
                 405                 410                 415

Asn Thr Gln Leu Gln Asn Leu Ser Phe Gln Arg Tyr Thr Ser Pro Gln
             420                 425                 430

Gly Asn Met Ile Ala Gln Asp Ile Ile Val Gly Val Ser Ala Asn Tyr
         435                 440                 445

Ser Asn Gly Val Asn Phe Lys Lys Thr Val Ser Trp Asn Pro Leu Lys
```

```
                450                 455                 460
Gly Tyr Thr Leu Lys Trp Glu Asn Asn Val Leu Glu Asp Tyr Pro Thr
465                 470                 475                 480

Leu Ser Ile Met Asn Met Ile Ser Asp Gln Asp Ser Ser Gly Phe Ala
                485                 490                 495

Ala Ile Asp Met Ser Val Leu Ser Tyr Asn Thr Ala Val Lys Gly Thr
                500                 505                 510

Cys Val Ser Gln Asn Asn Ile Val Phe Pro Asn Gln Lys Ile Gln Ser
                515                 520                 525

Ile Ser Ser Leu Ile Pro Asn Asn Thr Lys Ser Tyr Ser Tyr Tyr Gly
530                 535                 540

Asn Ser Asp Lys Leu Gly Leu Ile Thr Thr Leu Ile Ser Asn Asp Thr
545                 550                 555                 560

Thr Ser Ser Ile Ile Leu Ser Asn Thr Thr Gly Ile Asn Thr Phe Pro
                565                 570                 575

Ala Glu Gln Ala Thr Thr Thr Gly Thr Lys Leu Val Glu Tyr Val
                580                 585                 590

Asn Gly Ala Ala Ala Leu Gln Leu Lys Gln Asn Glu Ser Ala Gly Tyr
                595                 600                 605

Ile Ile Asp Thr Ser Ala Ile Pro Ser Gly Arg Tyr Lys Val Arg Phe
610                 615                 620

Arg Ala Ala Met Asn Gly Pro Tyr Asn Thr Ala Met Leu Ser Phe Thr
625                 630                 635                 640

Ile Asn Asn Tyr Val Glu Asp Ile Thr Val Ser Thr Asp Thr Lys Pro
                645                 650                 655

Leu Glu Ile Ile Gly Lys Gln Gly Ala Tyr Met Leu Ser Ser Ser Thr
                660                 665                 670

Phe Phe Glu Ile Pro Ser Thr Lys Ala Leu Pro Met Thr Ile Leu Asn
                675                 680                 685

Ser Thr Tyr Asn Asp Val Ile Leu Asp Arg Ile Glu Phe Ile Pro Ala
                690                 695                 700

Pro Met Glu Ala Ile Lys Asn Pro Ile Pro Ile Thr Tyr Asn Pro Gly
705                 710                 715                 720

Asn Leu Phe Phe Asp Pro Gly Val Asn Tyr Asn Asp Ile Trp Asn Asn
                725                 730                 735

Pro Asp Arg Lys Ile Ala Asp Ile Val Asn Leu Ser Gly Ser Ile Thr
                740                 745                 750

Tyr Ser Tyr Ala Thr Ala Pro Thr Thr Asn Val Ser Thr Ser Ile Glu
                755                 760                 765

Phe Leu Lys Val Asn Ala Val Val Ala Thr Val Pro Leu Glu Asp Arg
770                 775                 780

Ser Gly Thr Ser Gly Ser Pro Val Pro Leu Pro Ile Asn Ile Gln
785                 790                 795                 800

Lys Ser Ile Ile Gly Gly Phe Asp Gln Ile Arg Leu Lys Thr Thr Thr
                805                 810                 815

Asn Tyr Phe Cys Glu Gly Thr Ala Asn Ile Ser Gly Thr Val Gly Asn
                820                 825                 830

Gln Asn Ser Asp Pro Asn Asn Gly Asn Asn Gly Ser Pro Pro Tyr His
                835                 840                 845

Ser Cys Glu Met Val Asn Gly Glu Asn Leu Cys Ser Gly Pro Pro Lys
                850                 855                 860

Leu Glu Gln Leu Ser Asp Leu Glu Lys Ile Thr Ser Phe Val Thr Asn
865                 870                 875                 880
```

```
Leu Phe Glu Ser Ser Thr Tyr Met Glu Leu Ala Ser Asn Val Ser Ser
                885                 890                 895
Tyr Asn Ile Asp Gln Ala Ala Met Lys Val Asp Ala Leu Ser Ser Tyr
            900                 905                 910
Met Phe Ala Lys Glu Lys Val Leu Leu Arg Lys Leu Val Asn Lys Ala
        915                 920                 925
Lys Ala Leu Ile Gln Lys Arg Asn Leu Leu Val Asn Gly Asp Phe Gly
    930                 935                 940
Ser Tyr Lys Gly Trp Leu Tyr Gly Thr Leu Ala Thr Ile Ser Asn Asp
945                 950                 955                 960
Ser Pro Leu Phe Lys Cys Asn Tyr Leu Leu Glu Gln Leu Asn Thr
                965                 970                 975
Pro Val Ser Ser Tyr Val Tyr Gln Lys Ile Glu Glu Ser Gln Leu Lys
            980                 985                 990
Pro Tyr Thr Arg Tyr Lys Val Ser Gly Phe Ile Ala Glu Ser Lys Glu
        995                 1000                1005
Leu Glu Leu Val Val Ser Arg Tyr Asp Lys Glu Ile Tyr Lys Lys Leu
    1010                1015                1020
Asn Val Pro Tyr Ala Asp Ala Phe Pro Ile Ser Ser Asp Pro Thr Pro
1025                1030                1035                1040
Asn Cys Cys Gln Leu Asn Leu Cys Phe Asn Asp Asn Ser Asp Ser His
                1045                1050                1055
Phe Phe Ser Tyr Ser Ile Asp Val Gly Ala Leu His Pro Lys Phe Asn
            1060                1065                1070
Pro Gly Ile Glu Phe Gly Leu Cys Val Ala Asp Ala Asn Gly Ile Ala
        1075                1080                1085
Lys Val Gly Asn Leu Glu Ile Ile Glu Glu Arg Ser Leu Thr Asp Gln
    1090                1095                1100
Glu Ile Gln Val Ile Gln Gln Lys Glu Lys Asn Trp Lys Val Lys Val
1105                1110                1115                1120
Asp Arg Glu Tyr Lys Glu Ile Ser Ser Val Val Glu Pro Ile Ile Asn
                1125                1130                1135
Lys Leu Asn Ser Phe Phe Lys Asn Gly Asp Trp Asn Asp Glu Val Leu
            1140                1145                1150
Ser His Val Thr Tyr Gln Asp Val Tyr Ser Ile Val Leu Pro Arg Leu
        1155                1160                1165
Ser Lys Ser Glu His Trp Phe Met Thr Asn Ile Pro Glu Glu Glu Ala
    1170                1175                1180
Val Ile Leu Gln Glu Met Lys Gln Ala Leu Lys Arg Val Leu Phe Tyr
1185                1190                1195                1200
Leu Glu Glu Asn Asn Leu Val His Asn Gly Asn Phe Ile Asp Asp Leu
                1205                1210                1215
Asn Asn Trp Ile Val Glu Gly Thr Val Gln Ile Ile Asn Gly Asp Asn
            1220                1225                1230
Gly Asn Leu Ala Leu Gln Phe Ser Ser Trp Gly Ala Thr Val Ser Gln
        1235                1240                1245
Thr Ile Asn Ile Leu Asn Phe Asp Arg Asp Lys Gln Tyr Lys Leu Arg
    1250                1255                1260
Leu Tyr Gly Lys Gly Lys Gly Thr Val Thr Ile Glu His Gly Glu Glu
1265                1270                1275                1280
Ile Glu Asn Ile Thr Phe Asp Thr Asn Gln Phe Thr Thr Lys Glu His
                1285                1290                1295
Ile Phe Tyr Phe Asp Ala Ser Ser Phe Ile Leu Ser Ile Gln Ser Glu
            1300                1305                1310
```

```
Cys Asp Val Ser Ile Ile Asp Ser Val Glu Val Thr Glu Tyr Leu Asp
        1315                1320                1325
Lys

<210> SEQ ID NO 22
<211> LENGTH: 705
<212> TYPE: PRT
<213> ORGANISM: Bacillus thuringiensis

<400> SEQUENCE: 22

Met Glu Ile Thr Ser Glu Ile Tyr Pro Ile Ala Tyr Asn Val Leu Ala
  1               5                  10                  15

Asn Pro Pro Thr Leu Asp Thr Glu Asp Gln Gln Asn Pro Trp Asp Ala
             20                  25                  30

Tyr Val Asn Trp Arg Lys Gln Leu Asn Asp Thr Trp Leu Thr Tyr Asp
         35                  40                  45

Gln Asn Phe Leu Pro Asp Pro Val Met Ala Ile Asn Asp Met Ala
     50                  55                  60

Asn Ala Tyr Ala Gly Lys Pro Gly Ser Tyr Val Ala Leu Ala Gln Glu
 65                  70                  75                  80

Gly Ile Arg Ile Ala Phe Leu Phe Leu Pro Gly Gly Gln Thr Ala Ala
                 85                  90                  95

Phe Ala Ile Asn Lys Val Ile Gly Leu Phe Phe Pro Thr His Gln Pro
            100                 105                 110

Ser Leu Phe Asp Gln Ile Lys Asp Leu Val Glu Gln Met Ile Asp Gln
        115                 120                 125

Lys Phe Val Glu Gln Glu Ile Asn Ser Asn Ile Asn Gln Leu Asn Gly
130                 135                 140

Leu Ile Thr Gln Leu Gly Gln Phe Ser Asn Ser Met Gln Gln Ala Met
145                 150                 155                 160

Gly Lys Pro Met Asn Phe Pro Val Thr His Ser Ser Ala Thr Thr
                165                 170                 175

Asn Ser Phe Val Asp Thr Asn Glu Leu Asp Ser Tyr Asp Cys Ser Gln
            180                 185                 190

Asp Pro Asp Cys Ser Cys Ser Glu Asp Pro Asn Arg Thr Ser Asn Ser
        195                 200                 205

Pro Val Cys Thr Pro Cys Thr Cys Arg Ile Lys Gly Val Gln Asp Glu
    210                 215                 220

Phe Ile Ala Thr Arg Lys Val Ile Leu Asp Ile Leu Thr Ser Met Lys
225                 230                 235                 240

Thr Ser Leu Thr Asn Val Leu Thr Thr Glu His Ala Thr Thr Tyr Met
                245                 250                 255

Gln Ile Phe Leu Pro Ile Tyr Thr Thr Ala Val Thr Leu Tyr Phe Gly
            260                 265                 270

Met Tyr Lys Ser Tyr Ile Glu Phe Ala Thr Gln Tyr Gly Phe Glu Ile
        275                 280                 285

Gly Val Asn Gly Asn Thr Met Lys Tyr Ala Asn Glu Leu Gln Gln Tyr
    290                 295                 300

Ile Ser Ala Glu Ser Ala Tyr Val Tyr Asn Glu Phe Ala Met Tyr Leu
305                 310                 315                 320

Pro Asn Ser Lys Asn Leu Thr Lys Gly Asp Leu Asn Lys Tyr Ile Gln
                325                 330                 335

Tyr Ser Arg Thr Ile Thr Leu Asn Ala Leu Asp Thr Leu Ser Thr Trp
            340                 345                 350
```

```
Pro Leu Tyr Asn Val Leu Asp Tyr Pro Ile Ser Thr Thr Leu Asn Gln
        355                 360                 365

Thr Arg Leu Val Phe Asn Asp Ile Ile Gly Pro Val Glu Cys Arg Thr
    370                 375                 380

Gly Gly Gln Asn Ser Asp Asn Leu Ser Phe Asn Thr Leu Tyr Asp Tyr
385                 390                 395                 400

Ser Gly Asn Asn Leu Leu Asn Asn Asp Ile Thr Asn Tyr Phe Tyr Glu
                405                 410                 415

Asn Thr Gln Leu Gln Asn Leu Ser Phe Gln Arg Tyr Thr Ser Pro Gln
                420                 425                 430

Gly Asn Met Ile Ala Gln Asp Ile Ile Val Gly Val Ser Ala Asn Tyr
            435                 440                 445

Ser Asn Gly Val Asn Phe Lys Lys Thr Val Ser Trp Asn Pro Leu Lys
        450                 455                 460

Gly Tyr Thr Leu Lys Trp Glu Asn Asn Val Leu Asp Tyr Pro Thr
465                 470                 475                 480

Leu Ser Ile Met Asn Met Ile Ser Asp Gln Asp Ser Ser Gly Phe Ala
                485                 490                 495

Ala Ile Asp Met Ser Val Leu Ser Tyr Asn Thr Ala Val Lys Gly Thr
            500                 505                 510

Cys Val Ser Gln Asn Asn Ile Val Phe Pro Asn Gln Lys Ile Gln Ser
        515                 520                 525

Ile Ser Ser Leu Ile Pro Asn Asn Thr Lys Ser Tyr Ser Tyr Tyr Gly
    530                 535                 540

Asn Ser Asp Lys Leu Gly Leu Ile Thr Thr Leu Ile Ser Asn Asp Thr
545                 550                 555                 560

Thr Ser Ser Ile Ile Leu Ser Asn Thr Gly Ile Asn Thr Phe Pro
                565                 570                 575

Ala Glu Gln Ala Thr Thr Thr Gly Thr Lys Leu Val Glu Tyr Val
                580                 585                 590

Asn Gly Ala Ala Ala Leu Gln Leu Lys Gln Asn Glu Ser Ala Gly Tyr
                595                 600                 605

Ile Ile Asp Thr Ser Ala Ile Pro Ser Gly Arg Tyr Lys Val Arg Phe
    610                 615                 620

Arg Ala Ala Met Asn Gly Pro Tyr Asn Thr Ala Met Leu Ser Phe Thr
625                 630                 635                 640

Ile Asn Asn Tyr Val Glu Asp Ile Thr Val Ser Thr Asp Thr Lys Pro
                645                 650                 655

Leu Glu Ile Ile Gly Lys Gln Gly Ala Tyr Met Leu Ser Ser Ser Thr
                660                 665                 670

Phe Phe Glu Ile Pro Ser Thr Lys Ala Leu Pro Met Thr Ile Leu Asn
            675                 680                 685

Ser Thr Tyr Asn Asp Val Ile Leu Asp Arg Ile Glu Phe Ile Pro Ala
        690                 695                 700

Pro
705

<210> SEQ ID NO 23
<211> LENGTH: 1301
<212> TYPE: PRT
<213> ORGANISM: Bacillus thuringiensis

<400> SEQUENCE: 23

Met Arg Asn Leu Ile Asp Val Pro Val Phe Leu Asp Gln Val Ile Lys
1               5                   10                  15
```

```
Lys Ile Arg Gly Gly Leu Tyr Met Asn Ile Asn Asp Asn Lys Asn Glu
             20                  25                  30

Tyr Glu Ile Leu Asp Ser Gly Asn Leu Ser Tyr Gln Pro Arg Tyr Pro
         35                  40                  45

Leu Ala Arg Ala Pro Gly Ser Glu Cys Gln Lys Pro Asn Ala Lys Asp
 50                  55                  60

Gly Ile Tyr Thr Pro Val Gly Arg Val Asp Thr Ala Leu Gln Asn Ile
 65                  70                  75                  80

Asp Ile Gly Leu Ser Ile Arg Thr Ala Leu Ser Ile Leu Gln Met Leu
                 85                  90                  95

Leu Ser Val Ser Phe Pro Ala Leu Gly Arg Ala Ala Gly Leu Ile Asn
                100                 105                 110

Ile Ile Phe Gly Phe Leu Trp Gly Thr Leu Ala Gly Gln Ser Val Trp
             115                 120                 125

Glu Lys Phe Met Arg Ala Val Glu Ser Leu Val Asn Gln Lys Ile Thr
            130                 135                 140

Asp Ala Val Arg Val Lys Ala Leu Ser Glu Leu Glu Gly Val Gln Asn
145                 150                 155                 160

Ala Leu Glu Leu Tyr Gln Glu Ala Ala Asp Asp Trp Asn Glu Asn Pro
                165                 170                 175

Thr Asp Ala Ser Asn Lys Glu Arg Val Arg Arg Gln Phe Thr Ser Thr
            180                 185                 190

Asn Thr Thr Ile Glu Tyr Ala Met Pro Ser Phe Arg Val Pro Thr Phe
            195                 200                 205

Glu Val Pro Leu Leu Thr Val Tyr Ala Gln Ala Ala Asn Leu His Leu
            210                 215                 220

Gln Leu Leu Arg Asp Ala Val Lys Phe Gly Asn Glu Trp Gly Met Pro
225                 230                 235                 240

Ser Glu Glu Val Glu Asp Met Tyr Asn Arg Leu Thr Arg Arg Thr Ala
                245                 250                 255

Glu Tyr Thr Asp His Cys Val Ala Thr Tyr Asp Lys Gly Leu Lys Glu
            260                 265                 270

Ala Tyr Asp Leu Ala Pro Asn Pro Thr Asp Tyr Asn Lys Tyr Pro Tyr
            275                 280                 285

Leu Asn Pro Tyr Ser Lys Asp Pro Ile Tyr Gly Lys Tyr Tyr Thr Ala
290                 295                 300

Pro Val Asp Trp Asn Leu Phe Asn Asp Tyr Arg Arg Asp Met Thr Leu
305                 310                 315                 320

Met Val Leu Asp Ile Val Ala Val Trp Pro Thr Tyr Asn Pro Arg Ile
                325                 330                 335

Tyr Thr Asn Pro Asn Gly Val Gln Val Glu Leu Ser Arg Glu Val Tyr
            340                 345                 350

Ser Thr Val Tyr Gly Arg Gly Ser Asn Asn Ser Ser Phe Asp Ala
            355                 360                 365

Ile Glu Ser Gln Ile Val Arg Pro Pro His Leu Val Thr Glu Leu Thr
            370                 375                 380

Asn Leu Lys Ile Glu Gln Gly Ala Thr Leu Asp Met Glu Gln Ile Gln
385                 390                 395                 400

Tyr Pro Lys Tyr Met Lys Val Thr Asn Thr Leu His Tyr Val Gly Ser
                405                 410                 415

Ser Ser Thr Trp Glu Gln Ser Ser Ala Ile Pro Ile Arg Pro Ile
            420                 425                 430

Thr Gln Ile His Thr Ile Pro Ala Asn Asn Ile Gly Asn Leu Ser Leu
            435                 440                 445
```

```
Ser Gln Leu Asp Val Pro Tyr Arg Phe Ser Phe Tyr Asn Lys Asp Asp
    450                 455                 460

Ala Leu Ile Ala Ala Val Gly Ala Glu Phe Pro Pro Asn Thr Val Thr
465                 470                 475                 480

Trp Asn Gly Ile Pro Lys Ala Glu Asp Ser Asn Gln Asn Ser His His
                485                 490                 495

Leu Ser Tyr Val Gly Ala Leu Gly Thr Gln Ser Ser Ala Gly Phe Pro
            500                 505                 510

Trp Thr Tyr Pro Thr Glu Leu Leu Gly Glu Trp Gly Phe Gly Trp Leu
        515                 520                 525

His Asn Ser Leu Thr Pro Thr Asn Glu Ile Leu Ser Asp Lys Ile Thr
    530                 535                 540

Gln Ile Pro Ala Val Lys Ala Phe Asn Ile Gln Gly Asn Gly Lys Val
545                 550                 555                 560

Thr Lys Gly Pro Gly Ser Thr Gly Gly Asp Leu Ile Ala Leu Pro Ala
                565                 570                 575

Pro Ser Gly Gln Ile Asn Ile Tyr Leu Lys Glu Thr Ser Thr Lys Asn
            580                 585                 590

Tyr Arg Val Arg Leu Arg Tyr Ala Ala Thr Thr Asp Gly Gln Leu Arg
        595                 600                 605

Val Ala Arg Val Arg Asn Gly Gly Ala Val Arg Trp Phe Glu Asn Ile
610                 615                 620

Lys Tyr Val Thr Thr Gly Ala Ser Glu Asn Ser Leu Ala Tyr Asn Gln
625                 630                 635                 640

Phe Lys Tyr Val Asp Ile Phe Thr Ser Asp Phe Ser Asn Ile Asn Ser
                645                 650                 655

Leu Val Phe Ile Asn Gln Ser Gly Gly Thr Ile Leu Ile Asp Gln Ile
            660                 665                 670

Glu Phe Ile Pro Ile Glu Gly Ser Leu Glu Val Phe Glu Ala Glu Gln
        675                 680                 685

Asp Leu Glu Asn Ala Arg Lys Ala Val Asn Ala Leu Phe Thr Gly Ala
    690                 695                 700

Ala Lys Asp Val Leu Lys Leu Asn Val Thr Asp Tyr Ala Val Asp Gln
705                 710                 715                 720

Ala Ser Asn Leu Val Glu Cys Val Ser Asp Glu Phe His Ala Gln Glu
                725                 730                 735

Lys Met Ile Leu Leu Asp Gln Val Lys Phe Ala Lys Arg Leu Ser Gln
            740                 745                 750

Ala Arg Asn Leu Leu Asn Tyr Gly Asp Phe Glu Ser Ser Asp Trp Ser
        755                 760                 765

Gly Glu Asn Gly Trp Arg Thr Ser His His Val Ser Val Arg Ser Asp
    770                 775                 780

Asn Pro Thr Phe Lys Gly His Tyr Leu His Met Pro Gly Ala Thr Ser
785                 790                 795                 800

Ser Gln Phe Ser Asn Asn Val Tyr Pro Thr Tyr Val Tyr Gln Lys Val
                805                 810                 815

Asp Glu Ser Lys Leu Lys Ser Tyr Thr Arg Tyr Leu Val Arg Gly Phe
            820                 825                 830

Val Gly Asn Ser Lys Asp Leu Glu Leu Val Glu Arg Tyr Gly Lys
        835                 840                 845

Asp Val His Val Glu Met Asp Val Pro Asn Asp Ile Arg Tyr Ser Leu
    850                 855                 860

Pro Met Asn Glu Cys Gly Gly Phe Asp Arg Cys Lys Ser Ala Ser Asp
```

-continued

```
            865                 870                 875                 880
Gln Thr Arg Pro Pro His Thr Cys Thr Cys Lys Asn Thr Ala Val Ala
                    885                 890                 895
His Thr Asp Cys Gln Cys Gln Asp Lys Gly Asn Arg Ile Ser Thr Gly
                    900                 905                 910
Val Tyr Thr Asn Gly Pro Thr Gly Ser Ala Val Tyr Thr Asn Gly Phe
                    915                 920                 925
His Thr His Gln Ser Cys Gly Cys Lys Asn Lys Asn Ser Asp Arg Tyr
                    930                 935                 940
Gln Ser Gly Thr His Pro Gln Lys Ser Gly Cys Lys Asp Pro His
945                 950                 955                 960
Val Phe Ser Tyr His Ile Asp Thr Gly Cys Val Asp Gln Glu Glu Asn
                    965                 970                 975
Leu Gly Leu Trp Phe Ala Leu Lys Val Ala Ser Glu Asn Gly Val Ala
                    980                 985                 990
Asn Ile Asp Asn Leu Glu Ile Ile Glu Ala Gln Pro Leu Thr Gly Glu
                    995                 1000                1005
Ala Leu Ala Arg Val Lys Lys Arg Glu Gln Lys Trp Lys Gln Glu Met
    1010                1015                1020
Ala Gln Lys Arg Leu Gln Thr Asp Lys Ala Val Gln Ala Ala Gln Gly
1025                1030                1035                1040
Ala Ile Gln Pro Leu Phe Thr Asn Ala Gln Tyr Asn Arg Leu Gln Phe
                    1045                1050                1055
Glu Thr Leu Phe Pro Gln Ile Val Asn Ala Glu Met Leu Val Gln Gln
                    1060                1065                1070
Ile Pro Tyr Met Tyr His Pro Phe Leu Ser Gly Ala Leu Pro Thr Val
                    1075                1080                1085
Pro Gly Met Asn Phe Glu Ile Ile Gln Arg Leu Leu Ala Val Thr Gly
                    1090                1095                1100
Asn Ala Arg Gly Leu Tyr Glu Gln Arg Asn Leu Val Arg Asn Gly Thr
1105                1110                1115                1120
Phe Ser Ser Gly Thr Gly Ser Trp His Val Thr Glu Gly Val Glu Val
                    1125                1130                1135
Gln Pro Leu Gln Asn Thr Ser Val Leu Val Leu Ser Glu Trp Ser His
                    1140                1145                1150
Glu Ala Ser Gln Gln Val Arg Ile Asp Pro Asp Arg Gly Tyr Val Leu
                    1155                1160                1165
Arg Val Thr Ala Arg Lys Glu Gly Ala Gly Lys Gly Thr Val Thr Met
                    1170                1175                1180
Ser Asp Cys Ala Asp Tyr Thr Glu Thr Leu Thr Phe Thr Ser Cys Asp
1185                1190                1195                1200
Tyr Asn Thr Val Gly Thr Gln Thr Met Thr Gly Gly Thr Leu Ser Gly
                    1205                1210                1215
Phe Val Thr Lys Thr Leu Glu Ile Phe Pro Glu Thr Asp Arg Ile Arg
                    1220                1225                1230
Ile Asp Ile Gly Glu Thr Glu Gly Thr Phe Lys Ile Glu Ser Val Glu
                    1235                1240                1245
Leu Ile Cys Met Glu Gln Met Glu Asp His Leu Tyr Asp Met Ala Gly
                    1250                1255                1260
Asn Leu Glu Glu Glu Met Leu Asp Leu Gln Ser Ala Arg Ser Gly Ser
1265                1270                1275                1280
Gly Thr Lys Leu Ile Pro Pro Leu Thr Phe Ser Asp Cys Tyr Thr Asn
                    1285                1290                1295
```

```
Asn Glu Tyr Cys Tyr
            1300

<210> SEQ ID NO 24
<211> LENGTH: 678
<212> TYPE: PRT
<213> ORGANISM: Bacillus thuringiensis

<400> SEQUENCE: 24

Met Arg Asn Leu Ile Asp Val Pro Val Phe Leu Asp Gln Val Ile Lys
 1               5                  10                  15

Lys Ile Arg Gly Gly Leu Tyr Met Asn Ile Asn Asp Asn Lys Asn Glu
             20                  25                  30

Tyr Glu Ile Leu Asp Ser Gly Asn Leu Ser Tyr Gln Pro Arg Tyr Pro
         35                  40                  45

Leu Ala Arg Ala Pro Gly Ser Glu Cys Gln Lys Pro Asn Ala Lys Asp
     50                  55                  60

Gly Ile Tyr Thr Pro Val Gly Arg Val Asp Thr Ala Leu Gln Asn Ile
 65                  70                  75                  80

Asp Ile Gly Leu Ser Ile Arg Thr Ala Leu Ser Ile Leu Gln Met Leu
                 85                  90                  95

Leu Ser Val Ser Phe Pro Ala Leu Gly Arg Ala Ala Gly Leu Ile Asn
            100                 105                 110

Ile Ile Phe Gly Phe Leu Trp Gly Thr Leu Ala Gly Gln Ser Val Trp
        115                 120                 125

Glu Lys Phe Met Arg Ala Val Glu Ser Leu Val Asn Gln Lys Ile Thr
    130                 135                 140

Asp Ala Val Arg Val Lys Ala Leu Ser Glu Leu Glu Gly Val Gln Asn
145                 150                 155                 160

Ala Leu Glu Leu Tyr Gln Glu Ala Ala Asp Asp Trp Asn Glu Asn Pro
                165                 170                 175

Thr Asp Ala Ser Asn Lys Glu Arg Val Arg Arg Gln Phe Thr Ser Thr
            180                 185                 190

Asn Thr Thr Ile Glu Tyr Ala Met Pro Ser Phe Arg Val Pro Thr Phe
        195                 200                 205

Glu Val Pro Leu Leu Thr Val Tyr Ala Gln Ala Ala Asn Leu His Leu
    210                 215                 220

Gln Leu Leu Arg Asp Ala Val Lys Phe Gly Asn Glu Trp Gly Met Pro
225                 230                 235                 240

Ser Glu Glu Val Glu Asp Met Tyr Asn Arg Leu Thr Arg Arg Thr Ala
                245                 250                 255

Glu Tyr Thr Asp His Cys Val Ala Thr Tyr Asp Lys Gly Leu Lys Glu
            260                 265                 270

Ala Tyr Asp Leu Ala Pro Asn Pro Thr Asp Tyr Asn Lys Tyr Pro Tyr
        275                 280                 285

Leu Asn Pro Tyr Ser Lys Asp Pro Ile Tyr Gly Lys Tyr Tyr Thr Ala
    290                 295                 300

Pro Val Asp Trp Asn Leu Phe Asn Asp Tyr Arg Arg Asp Met Thr Leu
305                 310                 315                 320

Met Val Leu Asp Ile Val Ala Val Trp Pro Thr Tyr Asn Pro Arg Ile
                325                 330                 335

Tyr Thr Asn Pro Asn Gly Val Gln Val Glu Leu Ser Arg Glu Val Tyr
            340                 345                 350

Ser Thr Val Tyr Gly Arg Gly Ser Asn Asn Ser Phe Asp Ala
        355                 360                 365
```

```
Ile Glu Ser Gln Ile Val Arg Pro His Leu Val Thr Glu Leu Thr
    370                 375                 380

Asn Leu Lys Ile Glu Gln Gly Ala Thr Leu Asp Met Glu Gln Ile Gln
385                 390                 395                 400

Tyr Pro Lys Tyr Met Lys Val Thr Asn Thr Leu His Tyr Val Gly Ser
                405                 410                 415

Ser Ser Thr Trp Glu Gln Ser Ser Ala Ile Pro Ile Arg Pro Ile
            420                 425                 430

Thr Gln Ile His Thr Ile Pro Ala Asn Asn Ile Gly Asn Leu Ser Leu
                435                 440                 445

Ser Gln Leu Asp Val Pro Tyr Arg Phe Ser Phe Tyr Asn Lys Asp Asp
    450                 455                 460

Ala Leu Ile Ala Ala Val Gly Ala Glu Phe Pro Pro Asn Thr Val Thr
465                 470                 475                 480

Trp Asn Gly Ile Pro Lys Ala Glu Asp Ser Asn Gln Asn Ser His His
                485                 490                 495

Leu Ser Tyr Val Gly Ala Leu Gly Thr Gln Ser Ser Ala Gly Phe Pro
            500                 505                 510

Trp Thr Tyr Pro Thr Glu Leu Leu Gly Glu Trp Gly Phe Gly Trp Leu
                515                 520                 525

His Asn Ser Leu Thr Pro Thr Asn Glu Ile Leu Ser Asp Lys Ile Thr
    530                 535                 540

Gln Ile Pro Ala Val Lys Ala Phe Asn Ile Gln Gly Asn Gly Lys Val
545                 550                 555                 560

Thr Lys Gly Pro Gly Ser Thr Gly Gly Asp Leu Ile Ala Leu Pro Ala
                565                 570                 575

Pro Ser Gly Gln Ile Asn Ile Tyr Leu Lys Glu Thr Ser Thr Lys Asn
            580                 585                 590

Tyr Arg Val Arg Leu Arg Tyr Ala Ala Thr Thr Asp Gly Gln Leu Arg
                595                 600                 605

Val Ala Arg Val Arg Asn Gly Gly Ala Val Arg Trp Phe Glu Asn Ile
    610                 615                 620

Lys Tyr Val Thr Thr Gly Ala Ser Glu Asn Ser Leu Ala Tyr Asn Gln
625                 630                 635                 640

Phe Lys Tyr Val Asp Ile Phe Thr Ser Asp Phe Ser Asn Ile Asn Ser
                645                 650                 655

Leu Val Phe Ile Asn Gln Ser Gly Gly Thr Ile Leu Ile Asp Gln Ile
            660                 665                 670

Glu Phe Ile Pro Ile Glu
                675

<210> SEQ ID NO 25
<211> LENGTH: 1241
<212> TYPE: PRT
<213> ORGANISM: Bacillus thuringiensis

<400> SEQUENCE: 25

Met Ala Asn Gln Tyr Gln Asn Glu Phe Glu Ile Leu Asp Ala Asn Pro
1                   5                   10                  15

Ser Lys Asp Pro Ile Ala Asn Gly Ala Leu Arg Tyr Pro Leu Ala Thr
                20                  25                  30

Ser Pro Glu Ser Glu Leu Gln Asn Met Asn Tyr Lys Asp Trp Met Asp
            35                  40                  45

Met Cys Ala Val Gly Asn Ser Thr Gly Glu Ser Leu Ser Thr Lys Asp
    50                  55                  60
```

```
Ala Val Val Thr Ser Ile Asn Ile Thr Ser Tyr Leu Leu Ser Val Gly
 65                  70                  75                  80

Phe Pro Ala Ala Gly Ala Ala Phe Gly Ile Leu Gly Ala Leu Leu Gly
             85                  90                  95

Phe Leu Trp Pro Thr Asn Thr Gln Glu Ile Trp Gln Lys Phe Met Asn
            100                 105                 110

Ala Val Glu Glu Leu Val Asp Gln Lys Ile Glu Thr Phe Ala Arg Asn
            115                 120                 125

Gln Ala Ile Ala Arg Leu Ala Gly Ile His Gly Val Leu Lys Asp Tyr
            130                 135                 140

Gln Gly Ala Val Asn Asp Leu Asn Lys Asp Pro Asn Asn Pro Leu Leu
145                 150                 155                 160

Gln Glu Ile Thr Arg Thr Gln Phe Ile Ala Ala Glu Thr Phe Ile Thr
                165                 170                 175

Gly Ser Met Pro Leu Phe Gln Val Val Gly Gln Glu Val Pro Met Leu
            180                 185                 190

Thr Ile Phe Thr Glu Ala Ala Asn Leu His Leu Pro Leu Leu Arg Asp
            195                 200                 205

Gly Val Thr Phe Gly Ala Ser Trp Gly Val Pro Val Glu Thr Arg Asn
210                 215                 220

Arg Tyr Gln Leu Glu Leu Glu Asn Leu Ser Lys Tyr Thr Asp Tyr
225                 230                 235                 240

Cys Val Asn Ile Tyr Asn Ile Gly Leu Gln Gln Ala His Lys Leu Pro
                245                 250                 255

Pro Asn Tyr Asp Tyr Arg Ser Gly Lys Ile Pro Trp Ile Pro Pro Asn
            260                 265                 270

Leu Ser Asn Ser Ser Tyr Ser Arg Glu Ile Pro Tyr Trp Asn Pro Val
            275                 280                 285

Ile Asp Trp Asn Leu Tyr Asn Asn Tyr Arg Arg Asp Met Thr Leu Met
290                 295                 300

Val Leu Asp Val Val Ala Leu Trp Pro Met Tyr Asn Pro Lys Leu Tyr
305                 310                 315                 320

Ser Lys Pro Val Lys Ser Glu Leu Thr Arg Glu Leu Tyr Ser Glu Leu
            325                 330                 335

Ile Gly Gln Asn Asn Met Glu Asp Gln Asn Ala Ile Glu Asn Met Ile
            340                 345                 350

Val Arg Pro Pro His Leu Phe Thr Trp Leu Asp Thr Met Lys Phe Gly
            355                 360                 365

Phe Gln Ser Pro Lys Pro Asn Pro Gly Asn Gln Arg Gln Tyr Arg Asp
            370                 375                 380

Ile Gln Val Val Leu His Lys Thr Asn Asp Asn Ser Trp Glu Glu
385                 390                 395                 400

Thr Thr Val Ser Cys Tyr Gly Thr Arg Thr Ser Glu Thr Val Leu Asn
                405                 410                 415

Asn Ala Ala Tyr Gly Arg Val Glu Leu Ser Gly Ala Phe Ser Pro Cys
            420                 425                 430

Met Leu Arg Phe Tyr Thr Pro Tyr Asn Gly Gly Tyr Leu Val Gly
            435                 440                 445

Asn Asp Val Pro Asn Val Thr Ala Asp Thr Pro His Ala Gly Gly Gly
450                 455                 460

Asn Leu Val Asn Tyr Gly Thr Ala Arg Trp Tyr Ile Gly Thr Glu Ile
465                 470                 475                 480

Pro Tyr Ser Ser Leu Pro His Asn His Arg Leu Ser Tyr Val Asp Gly
            485                 490                 495
```

```
Cys Ser Thr Trp Phe Ser Tyr Pro Gly Ile Gly Asn Thr Phe Asn Trp
            500                 505                 510
Val Ser Ser Phe Val Phe Ala Trp Thr His Asn Asn Val Asp Pro Asn
            515                 520                 525
Asn Thr Ile Asp Pro Asn Lys Ile Thr Gln Ile Pro Ala Val Lys Gly
530                 535                 540
Tyr Gly Leu Gly Gly Asn Ala Thr Val Ile Arg Gly Pro Gly Ser Thr
545                 550                 555                 560
Gly Gly Asp Leu Val Gln Leu Pro Asn Pro Gly Ser Val Lys Ile Gln
            565                 570                 575
Leu Pro Val Ala Ser Lys Ser Gln Ser Tyr Arg Val Arg Ile Arg Tyr
            580                 585                 590
Ala Ser Ser Gly Asn Gly Thr Leu Arg Val Val Lys Trp Asn His Gly
            595                 600                 605
Tyr Tyr Ser His Ala Tyr Tyr Asn Val Ser Thr Thr Tyr Ser Ser Ala
            610                 615                 620
Leu Thr Tyr Asn Ser Phe Lys Tyr Leu Glu Ser Tyr Ala Ile Thr Met
625                 630                 635                 640
Tyr Pro Ala Asp Asn Asp Leu Glu Ile Trp Leu Glu Asn Ser Gly Gly
            645                 650                 655
Gly Pro Ile Ile Ile Asp Lys Ile Glu Phe Ile Pro Ile Gln Gly Thr
            660                 665                 670
Leu Ala Glu Tyr Glu Ala Asp Gln Ser Leu Glu Lys Ala Arg Lys Ala
            675                 680                 685
Val Asn Ala Leu Phe Thr Asn Asp Val Lys Asn Val Leu Gln Leu Lys
            690                 695                 700
Ile Thr Asp Tyr Glu Val Asp Gln Ala Ala Asn Leu Val Glu Cys Val
705                 710                 715                 720
Ser Glu Glu Phe His Ala Gln Glu Lys Met Ile Leu Leu Asp Gln Val
            725                 730                 735
Lys Phe Ala Lys Arg Leu Ser Gln Ser Arg Asn Leu Leu Asn Tyr Gly
            740                 745                 750
Asp Phe Glu Ser Ser Asp Trp Ser Gly Glu Asn Gly Trp Arg Thr Ser
            755                 760                 765
Ser His Val His Val Ala Ala Asp Asn Pro Ile Phe Lys Gly Arg Tyr
            770                 775                 780
Leu His Met Pro Gly Ala Met Ser Pro Gln Phe Ser Asn Asn Ile Tyr
785                 790                 795                 800
Pro Thr Tyr Ala Tyr Gln Lys Val Asp Glu Ser Lys Leu Lys Ser Tyr
            805                 810                 815
Thr Arg Tyr Leu Val Arg Gly Phe Val Gly Asn Ser Lys Asp Leu Glu
            820                 825                 830
Leu Leu Val Glu Arg Tyr Gly Lys Glu Val His Val Glu Met Asp Val
            835                 840                 845
Gln Asn Asp Ile Gln Tyr Thr Leu Pro Met Asn Glu Cys Gly Gly Phe
850                 855                 860
Asp Arg Cys Lys Pro Ala Ser Tyr Gln Glu Arg Leu Pro His Thr Cys
865                 870                 875                 880
Thr Cys Lys Asn Ala Ala Val Ala His Thr Asp Cys Gln Cys Lys Asp
            885                 890                 895
Lys Val Asn Arg Thr Ser Ala Asp Val Tyr Thr Asn Gly Leu Thr Ser
            900                 905                 910
Arg Gly Met Tyr Ala Asp Gly Phe Pro Ser His Lys Ser Cys Gly Cys
```

915                 920                 925
Lys Asn Gln Asn Ser Asp Met Tyr Gln Asn Gly Thr His Ser His Lys
        930                 935                 940
Ser Cys Gly Cys Lys Asp Pro His Val Phe Thr Tyr His Ile Asp Thr
945                 950                 955                 960
Gly Cys Val Asp Pro Glu Glu Asn Val Gly Leu Phe Phe Ala Leu Lys
                965                 970                 975
Ile Ala Ser Glu Asn Gly Ile Ala Asn Ile Asp Asn Leu Glu Ile Ile
            980                 985                 990
Glu Ala Gln Pro Leu Thr Gly Glu Ala Leu Ala Arg Val Lys Lys Arg
        995                 1000                1005
Glu Gln Lys Trp Lys His Glu Met Ala Gln Lys Arg Leu Gln Thr Glu
    1010                1015                1020
Lys Ala Val Gln Ala Ala Lys Gly Ala Ile Gln Asn Leu Phe Thr Asn
1025                1030                1035                1040
Ala Gln Gln Thr Gln Leu Lys His Lys Thr Leu Phe Pro Glu Ile Leu
                1045                1050                1055
Asn Ala Gly Arg Leu Val Gln His Ile Pro Tyr Val His His Pro Phe
            1060                1065                1070
Leu Ser Gly Ala Leu Pro Ala Val Pro Gly Met Asn Phe Asp Arg Phe
        1075                1080                1085
Gln Gln Phe Ser Phe Leu Val Glu Thr Ala Arg Gly Leu Tyr Glu Gln
    1090                1095                1100
Arg Asn Phe Val Ser Asn Gly Thr Phe Ser Ala Gly Ile Ala Asn Trp
1105                1110                1115                1120
Asn Ala Thr Asp Gly Val Thr Val Gln Pro Glu Gly Pro Thr Ser Val
                1125                1130                1135
Leu Val Leu Ser Asn Trp Ser Asp Lys Thr Phe Gln Asn Leu Arg Leu
            1140                1145                1150
Asp Pro Asp Arg Gly Tyr Val Leu Arg Val Thr Ala Arg Lys Glu Gly
        1155                1160                1165
Ala Gly Lys Gly Thr Val Thr Ile Ser Asp Cys Ala Ala Ser Pro Glu
    1170                1175                1180
Thr Leu Thr Phe Thr Ser Cys Asp Glu Asn Thr Ser Gly Thr Phe Val
1185                1190                1195                1200
Thr Lys Thr Leu Glu Ile Phe Pro Asp Thr Asp Arg Ile Arg Ile Asp
                1205                1210                1215
Ile Gly Glu Thr Glu Gly Thr Phe Arg Val Glu Ser Val Glu Leu Ile
            1220                1225                1230
Cys Met Glu Gln Met Glu Asp Asn Arg
        1235                1240

<210> SEQ ID NO 26
<211> LENGTH: 670
<212> TYPE: PRT
<213> ORGANISM: Bacillus thuringiensis

<400> SEQUENCE: 26

Met Ala Asn Gln Tyr Gln Asn Glu Phe Glu Ile Leu Asp Ala Asn Pro
1               5                   10                  15
Ser Lys Asp Pro Ile Ala Asn Gly Ala Leu Arg Tyr Pro Leu Ala Thr
            20                  25                  30
Ser Pro Glu Ser Glu Leu Gln Asn Met Asn Tyr Lys Asp Trp Met Asp
        35                  40                  45
Met Cys Ala Val Gly Asn Ser Thr Gly Glu Ser Leu Ser Thr Lys Asp

```
                50                  55                  60
Ala Val Val Thr Ser Ile Asn Ile Thr Ser Tyr Leu Leu Ser Val Gly
 65                  70                  75                  80

Phe Pro Ala Ala Gly Ala Ala Phe Gly Ile Leu Gly Ala Leu Leu Gly
                     85                  90                  95

Phe Leu Trp Pro Thr Asn Thr Gln Glu Ile Trp Gln Lys Phe Met Asn
                100                 105                 110

Ala Val Glu Glu Leu Val Asp Gln Lys Ile Glu Thr Phe Ala Arg Asn
                115                 120                 125

Gln Ala Ile Ala Arg Leu Ala Gly Ile His Gly Val Leu Lys Asp Tyr
                130                 135                 140

Gln Gly Ala Val Asn Asp Leu Asn Lys Asp Pro Asn Asn Pro Leu Leu
145                 150                 155                 160

Gln Glu Ile Thr Arg Thr Gln Phe Ile Ala Ala Glu Thr Phe Ile Thr
                165                 170                 175

Gly Ser Met Pro Leu Phe Gln Val Val Gly Gln Glu Val Pro Met Leu
                180                 185                 190

Thr Ile Phe Thr Glu Ala Ala Asn Leu His Leu Pro Leu Leu Arg Asp
                195                 200                 205

Gly Val Thr Phe Gly Ala Ser Trp Gly Val Pro Val Glu Thr Arg Asn
                210                 215                 220

Arg Tyr Gln Leu Glu Leu Glu Asn Leu Ser Lys Tyr Thr Asp Tyr
225                 230                 235                 240

Cys Val Asn Ile Tyr Asn Ile Gly Leu Gln Gln Ala His Lys Leu Pro
                245                 250                 255

Pro Asn Tyr Asp Tyr Arg Ser Gly Lys Ile Pro Trp Ile Pro Pro Asn
                260                 265                 270

Leu Ser Asn Ser Ser Tyr Ser Arg Glu Ile Pro Tyr Trp Asn Pro Val
                275                 280                 285

Ile Asp Trp Asn Leu Tyr Asn Asn Tyr Arg Arg Asp Met Thr Leu Met
                290                 295                 300

Val Leu Asp Val Val Ala Leu Trp Pro Met Tyr Asn Pro Lys Leu Tyr
305                 310                 315                 320

Ser Lys Pro Val Lys Ser Glu Leu Thr Arg Glu Leu Tyr Ser Glu Leu
                325                 330                 335

Ile Gly Gln Asn Asn Met Glu Asp Gln Asn Ala Ile Glu Asn Met Ile
                340                 345                 350

Val Arg Pro Pro His Leu Phe Thr Trp Leu Asp Thr Met Lys Phe Gly
                355                 360                 365

Phe Gln Ser Pro Lys Pro Asn Pro Gly Asn Gln Arg Gln Tyr Arg Asp
                370                 375                 380

Ile Gln Val Val Leu His Lys Thr Asn Asp Asn Asn Ser Trp Glu Glu
385                 390                 395                 400

Thr Thr Val Ser Cys Tyr Gly Arg Thr Ser Glu Thr Val Leu Asn
                405                 410                 415

Asn Ala Ala Tyr Gly Arg Val Glu Leu Ser Gly Ala Phe Ser Pro Cys
                420                 425                 430

Met Leu Arg Phe Tyr Thr Pro Tyr Asn Gly Gly Tyr Leu Val Gly
                435                 440                 445

Asn Asp Val Pro Asn Val Thr Ala Asp Thr Pro His Ala Gly Gly
                450                 455                 460

Asn Leu Val Asn Tyr Gly Thr Ala Arg Trp Tyr Ile Gly Thr Glu Ile
465                 470                 475                 480
```

```
Pro Tyr Ser Ser Leu Pro His Asn His Arg Leu Ser Tyr Val Asp Gly
            485                 490                 495

Cys Ser Thr Trp Phe Ser Tyr Pro Gly Ile Gly Asn Thr Phe Asn Trp
            500                 505                 510

Val Ser Ser Phe Val Phe Ala Trp Thr His Asn Asn Val Asp Pro Asn
            515                 520                 525

Asn Thr Ile Asp Pro Asn Lys Ile Thr Gln Ile Pro Ala Val Lys Gly
            530                 535                 540

Tyr Gly Leu Gly Gly Asn Ala Thr Val Ile Arg Gly Pro Gly Ser Thr
545                 550                 555                 560

Gly Gly Asp Leu Val Gln Leu Pro Asn Pro Gly Ser Val Lys Ile Gln
            565                 570                 575

Leu Pro Val Ala Ser Lys Ser Gln Ser Tyr Arg Val Arg Ile Arg Tyr
            580                 585                 590

Ala Ser Ser Gly Asn Gly Thr Leu Arg Val Val Lys Trp Asn His Gly
            595                 600                 605

Tyr Tyr Ser His Ala Tyr Tyr Asn Val Ser Thr Thr Tyr Ser Ser Ala
            610                 615                 620

Leu Thr Tyr Asn Ser Phe Lys Tyr Leu Glu Ser Tyr Ala Ile Thr Met
625                 630                 635                 640

Tyr Pro Ala Asp Asn Asp Leu Glu Ile Trp Leu Glu Asn Ser Gly Gly
            645                 650                 655

Gly Pro Ile Ile Ile Asp Lys Ile Glu Phe Ile Pro Ile Gln
            660                 665                 670

<210> SEQ ID NO 27
<211> LENGTH: 1312
<212> TYPE: PRT
<213> ORGANISM: Bacillus thuringiensis

<400> SEQUENCE: 27

Met Arg Thr Asn Leu Thr Glu His Arg Lys Ile Lys Lys Gly Gly Leu
  1               5                  10                  15

Tyr Met Asn Pro Asn Tyr Asn Asn Lys His Glu Ile Leu Asp Thr Asn
            20                  25                  30

Asn Arg Ser Tyr Gln Thr Arg Tyr Pro Leu Ala Asn Ala Pro Gly Val
        35                  40                  45

Glu Leu Gln Gln Met Ser Tyr Lys Asp Trp Met Asp Arg Cys Ala Gly
    50                  55                  60

Val Glu Ser Gly Glu Leu Phe Arg Asp Ala Thr Asp Ala Ile Arg Tyr
65                  70                  75                  80

Ser Leu Ile Val Gly Thr Gly Ile Gly Trp Ala Leu Leu Gly Phe Val
                85                  90                  95

Pro Gly Val Gly Pro Ala Leu Ser Ala Ala Ala Gly Val Leu Asn Val
            100                 105                 110

Ile Ile Pro Tyr Leu Trp Pro Glu Glu Val Gly Pro Pro Gly Thr Pro
        115                 120                 125

Gln Ala Gln Leu Thr Trp Glu Gln Leu Met Asn Ala Val Glu Gln Met
    130                 135                 140

Ile Asp Gln Lys Val Asp Thr Leu Ile Arg Arg Ala Ile Glu Thr
145                 150                 155                 160

Thr Arg Ile Leu Gln Ser Arg Leu Arg Asp Tyr Gln Gln Ala Leu Cys
                165                 170                 175

Asn Leu Gln Ser Asp Pro Asn Asn Glu Ala Tyr Lys Ala Asp Val Arg
            180                 185                 190
```

```
Arg Glu Phe Asn Asp Ala Glu Asp Gln Ala Lys Ala Ala Ile Ile Gln
        195                 200                 205

Phe Ser Pro Thr Thr Gly Asn Thr Thr Glu Asp Thr Lys Asn Asn Ile
210                 215                 220

Leu Leu Leu Ala Asp Tyr Thr Gln Ala Thr Asn Val His Leu Ile Leu
225                 230                 235                 240

Leu Arg Asp Val Ile Lys Phe Gly Ser Trp Gly Phe Ser Ser Leu
                245                 250                 255

Glu Val Gln Gln Tyr Tyr Ser Asn Thr Ser Pro Ile Gly Asn Pro Gly
            260                 265                 270

Met Leu Gln Leu Leu Asn Ile Tyr Thr Glu His Cys Leu Asn Trp Tyr
        275                 280                 285

Asp Lys Gly Leu Gln Gln Gln Tyr Gly Thr Gly Asp Trp Asn Lys Phe
290                 295                 300

Asn Asn Phe Arg Arg Asn Met Thr Ile Met Ala Leu Asp Thr Val Ser
305                 310                 315                 320

Val Trp Pro Thr Phe Asn Pro Lys His Tyr Ser Leu Pro Thr Lys Ser
                325                 330                 335

Gln Leu Thr Arg Thr Leu Asn Thr Ser Phe Ile Arg Ala His Gly Asn
            340                 345                 350

Thr Ser Lys Ile Ser Asp Ile Glu Asn Asn Val Val Ala Pro Thr Gly
        355                 360                 365

Leu Phe Lys Trp Leu Arg Lys Val Asp Tyr Tyr Ala Ala Thr Asp Phe
370                 375                 380

Ser His Pro Ala Leu Trp Cys Gly Leu Val Gln Tyr Tyr His Pro Thr
385                 390                 395                 400

Leu Ser Asp Val Leu Glu Glu Asp Val Lys Gly Ser Arg Asp Thr Tyr
                405                 410                 415

Met Gly Ser Leu Thr Val Pro Glu Pro Val Leu Glu Asp Asp Val Ser
            420                 425                 430

Leu Ile Thr Thr Asn Tyr Ser Tyr Met Gly Tyr Pro Pro Asn Glu Glu
        435                 440                 445

Ile Ser Tyr Phe Asn Glu Val Thr Phe His Leu Thr Lys Ser Ala Asp
450                 455                 460

Gln Thr Val Thr Phe Asn Ser Thr Thr Tyr Pro Tyr Ser Arg Lys Phe
465                 470                 475                 480

Gly Phe Pro Cys Arg Pro Asn Asn Ala Thr Ala Cys Asp Pro Cys Asp
                485                 490                 495

Ser Asp Asn Pro Cys Thr Asn Glu Ile Pro Asn Leu Thr Asp Pro Cys
            500                 505                 510

Asp Asp Lys Ser Leu Tyr Ser His Arg Phe Ser Tyr Met Gly Ala Gly
        515                 520                 525

Phe Pro Tyr Asn Leu Gly Gly Phe Ser Phe Gly Trp Thr His Val Ser
530                 535                 540

Ala Asp Ala Asn Asn Leu Ile Asp Pro Lys Lys Ile Thr Gln Ile Pro
545                 550                 555                 560

Ala Val Lys Ala Tyr Asn Leu Glu Asn Ala Arg Val Ile Lys Gly Pro
                565                 570                 575

Gly Ser Thr Gly Gly Asp Leu Val Glu Phe Ser Asn Gly Ala Thr Gln
            580                 585                 590

Gly Lys Met Tyr Met Ala Ile Thr Ser Pro Lys Gly Glu Asp Gln Tyr
        595                 600                 605

Tyr Asn Leu Arg Leu Arg Tyr Ala Ser Asn Asn Pro Thr Thr Thr Ile
610                 615                 620
```

```
Ser Ile Asn Gln Gly Gly Pro Ser Tyr Ala His Ser Thr Ala Thr Asp
625                 630                 635                 640

Ile Thr Asn Leu Thr Tyr Asp Lys Phe Gly Tyr Ala Asn Ile Asn Tyr
            645                 650                 655

Arg Ile Gly Leu Leu Pro Glu Ser Ile Asp Tyr Phe Thr Leu Glu Val
        660                 665                 670

Thr Gly Thr Asp Ser Gly Thr Phe Ile Leu Asp Lys Ile Glu Phe Ile
    675                 680                 685

Pro Ile Glu Gly Ser Val Glu Glu Phe Glu Ala Asn Gln Asp Ile Glu
690                 695                 700

Lys Ala Arg Lys Ala Val Asn Ala Leu Phe Thr Gly Asp Ala Lys Ser
705                 710                 715                 720

Ala Leu Lys Leu Asn Ile Thr Asp Tyr Ala Val Asp Gln Ala Ala Asn
            725                 730                 735

Leu Val Glu Cys Val Ser Glu Glu Phe His Ala Gln Glu Lys Ile Ile
        740                 745                 750

Leu Leu Asp Gln Val Lys Met Ala Lys Arg Leu Ser Gln Val Arg Asn
    755                 760                 765

Leu Leu Asn Tyr Gly Asp Phe Glu Ser Pro Asp Trp Ser Gly Glu Asn
770                 775                 780

Gly Trp Lys Thr Ser Thr His Val Ser Val Arg Ala Asp Asn Pro Val
785                 790                 795                 800

Phe Lys Gly Arg Tyr Leu His Met Pro Gly Gly Met Ser Pro Gln Phe
            805                 810                 815

Ser Asn Asn Ile Tyr Pro Thr Tyr Ala Tyr Gln Lys Val Asp Glu Ser
        820                 825                 830

Lys Leu Lys Ser Tyr Thr Arg Tyr Leu Val Arg Gly Phe Val Gly Asn
    835                 840                 845

Ser Lys Asp Leu Glu Leu Leu Val Glu Arg Tyr Gly Lys Asp Val His
850                 855                 860

Val Glu Met Asp Val Pro Asn Asp Ile Arg Tyr Ser Leu Pro Met Asn
865                 870                 875                 880

Glu Cys Gly Gly Phe Asp Arg Cys Lys Pro Ala Ser Tyr Gln Ala Arg
            885                 890                 895

Thr Arg His Ala Cys Thr Cys Lys Asn Asn Ala Val Ala His Thr Asp
        900                 905                 910

Cys Gln Cys Lys Asp Lys Glu Lys Arg Thr Ser Thr Asn Met Tyr Thr
    915                 920                 925

Asn Val Pro Ala Asp Ser Ala Val Tyr Thr Asn Gly Phe His Ala His
930                 935                 940

Lys Ser Cys Glu Cys Lys Asn Asn Asp Met Tyr Gln Asn Gly Thr Gln
945                 950                 955                 960

Ser His Lys Ser Cys Gly Tyr Lys Asp Pro His Val Phe Thr Tyr His
            965                 970                 975

Ile Asp Thr Gly Cys Val Asp Met Glu Glu Asn Val Gly Leu Phe Phe
        980                 985                 990

Ala Leu Lys Ile Ala Ser Glu Asn Gly Val Ala Asn Ile Asn Asn Leu
    995                 1000                1005

Glu Ile Ile Glu Ala Gln Pro Leu Thr Gly Glu Ala Leu Ala Arg Val
    1010                1015                1020

Lys Lys Arg Glu Gln Lys Trp Lys Gln Glu Ile Ala Gln Lys Arg Leu
1025                1030                1035                1040

Arg Thr Glu Lys Ala Val Gln Ala Ala Lys Gly Ala Leu Gln Thr Leu
```

```
                            1045                1050                1055

Phe Ala Asn Ala Gln Tyr Asn Arg Leu Lys Phe Glu Thr Leu Phe Pro
                1060                1065                1070

Gln Ile Val His Ala Glu Lys Leu Val Gln Gln Ile Pro Tyr Ala Tyr
                1075                1080                1085

His Pro Phe Leu Ser Gly Ala Leu Pro Thr Val Pro Gly Met Asn Phe
                1090                1095                1100

Glu Ile Ile Gln Gln Leu Leu Ala Val Ile Gly Asn Ala Arg Thr Leu
1105                1110                1115                1120

Tyr Glu Lys Arg Asn Leu Val Arg Thr Gly Thr Phe Ser Ser Gly Thr
                1125                1130                1135

Gly Ser Trp Lys Val Thr Glu Gly Val Lys Val Gln Pro Leu Gln Asp
                1140                1145                1150

Thr Ser Val Leu Val Leu Ser Glu Trp Ser His Glu Ala Ser Gln Gln
                1155                1160                1165

Phe Arg Ile Asp Pro Asp Arg Gly Tyr Val Leu Arg Val Thr Ala Arg
                1170                1175                1180

Lys Glu Gly Gly Gly Lys Gly Thr Val Thr Met Ser Asp Cys Ala Asp
1185                1190                1195                1200

Tyr Thr Glu Thr Leu Thr Phe Thr Ser Cys Asp Tyr Asn Thr Tyr Gly
                1205                1210                1215

Pro Pro Thr Leu Thr Ser Gly Thr Leu Ser Gly Phe Val Thr Lys Thr
                1220                1225                1230

Leu Glu Val Phe Pro Asp Thr Asp Arg Ile Arg Ile Asp Met Gly Glu
                1235                1240                1245

Thr Glu Gly Thr Phe Gln Val Glu Ser Val Glu Leu Ile Cys Met Glu
                1250                1255                1260

Gln Met Glu Asp Asp Leu Tyr Asp Met Ala Gly Asn Leu Glu Glu Glu
1265                1270                1275                1280

Met Gln Tyr Leu Glu Gln Ser Arg Ser Met Gly Asn Thr Glu Phe Ile
                1285                1290                1295

Pro Pro Leu Thr Ser Gln Ala Ser Gly Cys Val Asp Thr Ile Trp Cys
                1300                1305                1310

<210> SEQ ID NO 28
<211> LENGTH: 691
<212> TYPE: PRT
<213> ORGANISM: Bacillus thuringiensis

<400> SEQUENCE: 28

Met Arg Thr Asn Leu Thr Glu His Arg Lys Ile Lys Lys Gly Gly Leu
1               5                   10                  15

Tyr Met Asn Pro Asn Tyr Asn Asn Lys His Glu Ile Leu Asp Thr Asn
                20                  25                  30

Asn Arg Ser Tyr Gln Thr Arg Tyr Pro Leu Ala Asn Ala Pro Gly Val
            35                  40                  45

Glu Leu Gln Gln Met Ser Tyr Lys Asp Trp Met Asp Arg Cys Ala Gly
        50                  55                  60

Val Glu Ser Gly Glu Leu Phe Arg Asp Ala Thr Asp Ala Ile Arg Tyr
65                  70                  75                  80

Ser Leu Ile Val Gly Thr Gly Ile Gly Trp Ala Leu Leu Gly Phe Val
                85                  90                  95

Pro Gly Val Gly Pro Ala Leu Ser Ala Ala Ala Gly Val Leu Asn Val
                100                 105                 110

Ile Ile Pro Tyr Leu Trp Pro Glu Glu Val Gly Pro Pro Gly Thr Pro
```

```
                  115                 120                 125
Gln Ala Gln Leu Thr Trp Glu Gln Leu Met Asn Ala Val Glu Gln Met
130                 135                 140

Ile Asp Gln Lys Val Asp Thr Leu Ile Arg Asp Arg Ala Ile Glu Thr
145                 150                 155                 160

Thr Arg Ile Leu Gln Ser Arg Leu Arg Asp Tyr Gln Gln Ala Leu Cys
                165                 170                 175

Asn Leu Gln Ser Asp Pro Asn Asn Glu Ala Tyr Lys Ala Asp Val Arg
            180                 185                 190

Arg Glu Phe Asn Asp Ala Glu Asp Gln Ala Lys Ala Ala Ile Ile Gln
        195                 200                 205

Phe Ser Pro Thr Thr Gly Asn Thr Thr Glu Asp Thr Lys Asn Asn Ile
    210                 215                 220

Leu Leu Leu Ala Asp Tyr Thr Gln Ala Thr Asn Val His Leu Ile Leu
225                 230                 235                 240

Leu Arg Asp Val Ile Lys Phe Gly Glu Ser Trp Gly Phe Ser Ser Leu
                245                 250                 255

Glu Val Gln Gln Tyr Tyr Ser Asn Thr Ser Pro Ile Gly Asn Pro Gly
            260                 265                 270

Met Leu Gln Leu Leu Asn Ile Tyr Thr Glu His Cys Leu Asn Trp Tyr
        275                 280                 285

Asp Lys Gly Leu Gln Gln Gln Tyr Gly Thr Gly Asp Trp Asn Lys Phe
    290                 295                 300

Asn Asn Phe Arg Arg Asn Met Thr Ile Met Ala Leu Asp Thr Val Ser
305                 310                 315                 320

Val Trp Pro Thr Phe Asn Pro Lys His Tyr Ser Leu Pro Thr Lys Ser
                325                 330                 335

Gln Leu Thr Arg Thr Leu Asn Thr Ser Phe Ile Arg Ala His Gly Asn
            340                 345                 350

Thr Ser Lys Ile Ser Asp Ile Glu Asn Asn Val Val Ala Pro Thr Gly
        355                 360                 365

Leu Phe Lys Trp Leu Arg Lys Val Asp Tyr Tyr Ala Ala Thr Asp Phe
    370                 375                 380

Ser His Pro Ala Leu Trp Cys Gly Leu Val Gln Tyr Tyr His Pro Thr
385                 390                 395                 400

Leu Ser Asp Val Leu Glu Glu Asp Val Lys Gly Ser Arg Asp Thr Tyr
                405                 410                 415

Met Gly Ser Leu Thr Val Pro Glu Pro Val Leu Glu Asp Asp Val Ser
            420                 425                 430

Leu Ile Thr Thr Asn Tyr Ser Tyr Met Gly Tyr Pro Pro Asn Glu Glu
        435                 440                 445

Ile Ser Tyr Phe Asn Glu Val Thr Phe His Leu Thr Lys Ser Ala Asp
    450                 455                 460

Gln Thr Val Thr Phe Asn Ser Thr Thr Tyr Pro Tyr Ser Arg Lys Phe
465                 470                 475                 480

Gly Phe Pro Cys Arg Pro Asn Asn Ala Thr Ala Cys Asp Pro Cys Asp
                485                 490                 495

Ser Asp Asn Pro Cys Thr Asn Glu Ile Pro Asn Leu Thr Asp Pro Cys
            500                 505                 510

Asp Asp Lys Ser Leu Tyr Ser His Arg Phe Ser Tyr Met Gly Ala Gly
        515                 520                 525

Phe Pro Tyr Asn Leu Gly Gly Phe Ser Phe Gly Trp Thr His Val Ser
    530                 535                 540
```

```
Ala Asp Ala Asn Asn Leu Ile Asp Pro Lys Lys Ile Thr Gln Ile Pro
545                 550                 555                 560

Ala Val Lys Ala Tyr Asn Leu Glu Asn Ala Arg Val Ile Lys Gly Pro
                565                 570                 575

Gly Ser Thr Gly Gly Asp Leu Val Glu Phe Ser Asn Gly Ala Thr Gln
            580                 585                 590

Gly Lys Met Tyr Met Ala Ile Thr Ser Pro Lys Gly Glu Asp Gln Tyr
        595                 600                 605

Tyr Asn Leu Arg Leu Arg Tyr Ala Ser Asn Asn Pro Thr Thr Thr Ile
    610                 615                 620

Ser Ile Asn Gln Gly Gly Pro Ser Tyr Ala His Ser Thr Ala Thr Asp
625                 630                 635                 640

Ile Thr Asn Leu Thr Tyr Asp Lys Phe Gly Tyr Ala Asn Ile Asn Tyr
                645                 650                 655

Arg Ile Gly Leu Leu Pro Glu Ser Ile Asp Tyr Phe Thr Leu Glu Val
            660                 665                 670

Thr Gly Thr Asp Ser Gly Thr Phe Ile Leu Asp Lys Ile Glu Phe Ile
        675                 680                 685

Pro Ile Glu
    690

<210> SEQ ID NO 29
<211> LENGTH: 1426
<212> TYPE: PRT
<213> ORGANISM: Bacillus thuringiensis

<400> SEQUENCE: 29

Met Asn Leu Asn Gly Asn Lys Asn Glu Phe Glu Ile Leu Asp Thr Gly
1               5                   10                  15

Asn Met Ala Tyr Gln Pro Arg Tyr Pro Leu Thr Gln Ser Pro Ala Ser
                20                  25                  30

Glu Leu Gln Gly Met Asn Tyr Lys Glu Trp Ile Asn Arg Cys Glu Asp
        35                  40                  45

Gln Glu Leu Gly Glu Leu Phe Val Asp Ser Asn Ala Val Arg Asn Ala
    50                  55                  60

Val Val Ile Gly Ala Lys Ile Thr Ala Thr Ile Val Gly Ile Ala Phe
65                  70                  75                  80

Pro Pro Leu Lys Ile Pro Ala Gln Ile Leu Ser Thr Leu Ile Pro Val
                85                  90                  95

Leu Trp Pro Lys Glu Ala Gly Pro Pro Gly Thr Ala Glu Ala Gln Phe
                100                 105                 110

Thr Trp Glu Gln Met Met Ser Ala Val Glu Glu Met Ile Asp Gln Lys
        115                 120                 125

Val Glu Ile Ala Val Lys Asp Arg Ala Ile Glu Thr Leu Gln Ile Leu
130                 135                 140

Gln Ser Arg Ile Arg Asp Tyr Gln Gln Ala Leu Cys Asn Leu Gln Thr
145                 150                 155                 160

Asp Pro Asp Asn Glu Arg Phe Lys Glu Asp Val Arg Arg Glu Phe Asn
                165                 170                 175

Asp Ala Glu Asp Gln Ala Lys Ala Ala Val Ile Gln Phe Gly Asn Pro
            180                 185                 190

Asn Tyr Ala Ile Pro Leu Leu Pro Asp Tyr Ala Gln Ala Ala Asn Ile
        195                 200                 205

His Leu Leu Leu Leu Arg Asp Val Val Gln Tyr Gly Glu Ile Trp Gly
    210                 215                 220
```

-continued

Phe Ser Phe Val Glu Val Gln Gln Tyr Tyr Phe Asn Asn Gln Ile Gly
225                 230                 235                 240

Asn Pro Gly Met Lys Gln Leu Leu Ala Thr Tyr Thr Asp His Cys Val
            245                 250                 255

Arg Trp Tyr Asn Asn Gly Leu Thr Asn Arg Tyr Glu Thr Gly Gly Trp
        260                 265                 270

Asn Thr Phe Asn Asp Phe Arg Arg Asn Met Thr Leu Met Val Met Asp
    275                 280                 285

Val Val Ser Phe Trp Pro Thr Tyr Asp Pro Met Leu Tyr Lys Ile Pro
290                 295                 300

Thr Lys Ser Gln Leu Thr Arg Ile Val Tyr Thr Pro Leu Ile Gly Arg
305                 310                 315                 320

Ala Asp Asp Phe Pro Gly Ile Pro Ala Pro Thr Ile Gly Glu Lys Glu
                325                 330                 335

Ser Thr Leu Thr Gln Pro Pro Arg Leu Phe Ala Trp Leu Arg Glu Leu
            340                 345                 350

Ser Ile Gly Glu Thr Thr Phe Pro Tyr Tyr Phe Ser Thr Gly Phe Cys
        355                 360                 365

Gly Arg Lys Gln Ile Phe Gln Asn Thr Met Asp Asn Asn Leu Trp Glu
    370                 375                 380

Glu Pro Tyr Lys Gly Ser Pro Gly Val Lys Asp Thr Gln Thr Leu Ile
385                 390                 395                 400

Ile Pro Ala Pro Glu Val Asn Asp Asp Val Trp Arg Ile Val Thr Tyr
                405                 410                 415

Leu Lys Lys Met Ala Gly Ser Ile Gln Tyr Asp Glu Ile Met Gly Trp
            420                 425                 430

Asp Phe Ser Phe Thr Lys Ser Leu Asp Gln Arg Leu Tyr Arg Tyr His
        435                 440                 445

Leu Arg Ser Val Ser Ser Gly Met Pro Cys Gly Gly Ser Phe Pro Gly
    450                 455                 460

Pro Cys Asp Pro Cys Asn Ser Val Asp Pro Cys Ser Phe Glu Leu Pro
465                 470                 475                 480

Asn Pro Thr Ile Pro Cys Asp Asp Lys Ala Leu Tyr Ser His Arg Phe
                485                 490                 495

Ala Tyr Met Gly Ala Gly Phe Val Ser Asn Leu Ala Ala Met Thr Tyr
            500                 505                 510

Phe Ser Tyr Gly Trp Thr His Val Ser Ala Asp Ala Asn Asn Leu Ile
        515                 520                 525

Asp Ala Glu Arg Ile Thr Gln Ile Pro Ala Val Lys Gly Ser Glu Met
    530                 535                 540

Glu Gly Thr Ala Lys Val Ile Gln Gly Pro Gly Ser Thr Gly Gly Asp
545                 550                 555                 560

Leu Val Gln Leu Asp Tyr Arg Gly Lys Ile Gln Ile Ser Met Thr Ala
                565                 570                 575

Pro Val Arg Lys Gly Tyr Gln Leu Arg Ile Arg Tyr Ala Thr Ala Ser
            580                 585                 590

Thr Ala Glu Ile His Val Ser Arg Val Ser Ile Arg Glu Asp Asp Ser
        595                 600                 605

Ser Asn Glu Asp Tyr Tyr His Phe Glu Phe Leu Pro Gln Thr Tyr Leu
    610                 615                 620

Ala Gly Ser Leu Asn Phe Asn Ser Phe Gly Tyr Thr Thr Met Ser Ile
625                 630                 635                 640

Pro Leu Pro Pro Gly Ala Gly Glu Gln Trp Asp Met Ser Phe Gln Trp
                645                 650                 655

```
Phe Gly Thr Asp Ser Pro Ile Ile Ile Asp Lys Ile Glu Phe Ile Pro
            660                 665                 670
Ile Glu Gly Ser Val Glu Glu Phe Glu Ala Asn Gln Ala Val Glu Lys
            675                 680                 685
Ala Arg Lys Ala Val Asn Ala Leu Phe Thr Asn Asp Ala Lys Asn Ala
            690                 695                 700
Leu Gln Leu Asn Val Thr Asp Tyr Ala Val Asp Gln Ala Ala Asn Leu
705                 710                 715                 720
Val Glu Cys Val Ser Glu Glu Phe His Ala Gln Glu Lys Met Ile Leu
                725                 730                 735
Leu Asp Gln Val Lys Phe Ala Lys Arg Leu Ser Gln Glu Arg Asn Leu
            740                 745                 750
Leu Asn Tyr Gly Asp Phe Glu Ser Ser Asp Trp Ser Gly Glu Asn Gly
            755                 760                 765
Trp Arg Thr Ser Pro His Val His Val Thr Ser Asp Asn Pro Ile Phe
770                 775                 780
Lys Gly Arg Tyr Leu His Met Pro Gly Ala Met Ser Pro Gln Phe Ser
785                 790                 795                 800
Asn Asn Ile Tyr Leu Thr Tyr Ala Tyr Gln Lys Val Asp Glu Ser Lys
                805                 810                 815
Leu Lys Ser Tyr Thr Arg Tyr Leu Val Arg Gly Phe Val Gly Asn Ser
            820                 825                 830
Lys Asp Leu Glu Leu Leu Val Glu Arg Tyr Gly Lys Glu Val His Val
            835                 840                 845
Glu Met Asp Val Pro Asn Asp Ile Arg Tyr Ser Leu Pro Met Asn Asp
850                 855                 860
Cys Gly Gly Phe Asp Arg Cys Lys Pro Val Ser Tyr Gln Glu Arg Leu
865                 870                 875                 880
Pro His Thr Cys Thr Cys Lys Asp Thr Ala Val Ala His Thr Asp Cys
                885                 890                 895
Glu Cys Lys Asp Lys Val Asn Arg Thr Ser Ala Asp Val Tyr Thr Asn
            900                 905                 910
Met Met Thr Asp His Ala Val Asp Thr Asn Gly Phe His Ser His Gln
            915                 920                 925
Ser Cys Gly Cys Lys Asn Asn Asp Thr Ser Arg Asn Gly Lys His Pro
930                 935                 940
His Lys Ser Cys Gly Cys Gln Asp Pro His Val Phe Thr Tyr His Ile
945                 950                 955                 960
Asp Thr Gly Cys Val Asp Gln Glu Glu Asn Leu Gly Leu Phe Phe Ala
                965                 970                 975
Leu Lys Ile Ala Ser Glu Asn Gly Ile Ala Asn Ile Asp Asn Leu Glu
            980                 985                 990
Ile Ile Glu Ala Gln Pro Leu Thr Gly Glu Ala Leu Ala Arg Val Lys
            995                 1000                1005
Lys Arg Glu His Lys Trp Lys Gln Glu Met Ile Gln Lys Arg Leu Gln
        1010                1015                1020
Thr Glu Lys Ala Val Gln Ala Ala Arg Gly Ala Ile Gln Asn Leu Phe
1025                1030                1035                1040
Thr Asn Ala Gln Gln Thr Gln Leu Lys His Glu Thr Leu Phe Pro Glu
                1045                1050                1055
Ile Leu Asn Ala Gly Lys Leu Val Gln Asp Ile Pro Tyr Val His His
            1060                1065                1070
Pro Phe Leu Ser Gly Ala Leu Leu Thr Val Pro Gly Met Asn Phe Asp
```

```
                    1075                1080                1085

Val Phe Gln Gln Leu Ser Phe Leu Ser Glu Thr Ala Arg Gly Leu Tyr
    1090                1095                1100

Glu Gln Arg Asn Leu Val Ser Asn Gly Thr Phe Gly Ala Gly Ile Ala
1105                1110                1115                1120

Asn Trp Asn Ala Thr Asp Gly Val Thr Val Gln Pro Glu Gly Pro Thr
            1125                1130                1135

Ser Val Leu Val Leu Ser Asn Trp Ser Asp Lys Ala Phe Gln Asn Leu
        1140                1145                1150

Arg Leu Asp Pro Asp Arg Gly Tyr Val Leu Arg Val Thr Ala Arg Lys
    1155                1160                1165

Glu Gly Arg Gly Lys Gly Thr Val Thr Ile Ser Asp Cys Thr Ala Tyr
1170                1175                1180

Pro Glu Thr Leu Leu Phe Thr Ser Cys Asp Lys Asn Thr Ile Asp Thr
1185                1190                1195                1200

Phe Val Thr Lys Thr Leu Glu Ile Phe Pro Asp Thr Asp Arg Ile Arg
            1205                1210                1215

Ile Asp Ile Gly Glu Thr Glu Gly Met Phe Lys Ile Glu Ser Val Glu
        1220                1225                1230

Leu Ile Cys Ile Glu His Met Glu Asp His Ile Tyr Asp Met Ala Arg
    1235                1240                1245

Val Gly Pro Ala Lys Ala Glu His Pro Ile Leu Lys Asp Ala Asn
1250                1255                1260

Gly Ser Pro Val Val Tyr Gly Gln Glu Tyr Tyr Met Glu Pro Tyr Glu
1265                1270                1275                1280

Phe Pro Gly Tyr Lys Leu Gly Glu Ser Ile Asn Val Gly Gly Ile Asn
            1285                1290                1295

Glu Ile Ala Leu Ala Pro Ser Met Tyr Met Lys Pro Met Glu Leu Thr
        1300                1305                1310

Phe Glu Lys Asn Val Thr Thr Pro Glu Asp Met Val Phe Ile Gln His
    1315                1320                1325

Lys Ala Thr Gly Pro Gly Ser Gly Leu His Gly Ile His Tyr Val Ser
1330                1335                1340

Val Phe Asp Ser Ser Thr Ser Tyr Leu Gln Leu Met Tyr Pro Ser Thr
1345                1350                1355                1360

Asp Ala Asn Gln Ser Met Trp Lys Pro Ile Leu Pro Ser Val Asp Met
            1365                1370                1375

Asp Ser Lys Phe Ile Asp Gly Asn Tyr Phe Ala Phe Lys Asn Glu Asn
        1380                1385                1390

Leu Asn Val Phe Leu Ala Tyr Gln Asn Leu Asn Glu Arg His Ser Tyr
    1395                1400                1405

Ala His Val Gly Thr Met Asn Ser Lys Thr Met Trp Arg Leu Ile Pro
1410                1415                1420

Ile Gln
1425

<210> SEQ ID NO 30
<211> LENGTH: 674
<212> TYPE: PRT
<213> ORGANISM: Bacillus thuringiensis

<400> SEQUENCE: 30

Met Asn Leu Asn Gly Asn Lys Asn Glu Phe Glu Ile Leu Asp Thr Gly
1               5                   10                  15

Asn Met Ala Tyr Gln Pro Arg Tyr Pro Leu Thr Gln Ser Pro Ala Ser
```

-continued

```
                20                  25                  30
Glu Leu Gln Gly Met Asn Tyr Lys Glu Trp Ile Asn Arg Cys Glu Asp
             35                  40                  45

Gln Glu Leu Gly Glu Leu Phe Val Asp Ser Asn Ala Val Arg Asn Ala
         50                  55                  60

Val Val Ile Gly Ala Lys Ile Thr Ala Thr Ile Val Gly Ile Ala Phe
65                  70                  75                  80

Pro Pro Leu Lys Ile Pro Ala Gln Ile Leu Ser Thr Leu Ile Pro Val
                 85                  90                  95

Leu Trp Pro Lys Glu Ala Gly Pro Pro Gly Thr Ala Glu Ala Gln Phe
            100                 105                 110

Thr Trp Glu Gln Met Met Ser Ala Val Glu Glu Met Ile Asp Gln Lys
        115                 120                 125

Val Glu Ile Ala Val Lys Asp Arg Ala Ile Glu Thr Leu Gln Ile Leu
    130                 135                 140

Gln Ser Arg Ile Arg Asp Tyr Gln Gln Ala Leu Cys Asn Leu Gln Thr
145                 150                 155                 160

Asp Pro Asp Asn Glu Arg Phe Lys Glu Asp Val Arg Arg Glu Phe Asn
                165                 170                 175

Asp Ala Glu Asp Gln Ala Lys Ala Ala Val Ile Gln Phe Gly Asn Pro
            180                 185                 190

Asn Tyr Ala Ile Pro Leu Leu Pro Asp Tyr Ala Gln Ala Ala Asn Ile
        195                 200                 205

His Leu Leu Leu Leu Arg Asp Val Val Gln Tyr Gly Glu Ile Trp Gly
    210                 215                 220

Phe Ser Phe Val Glu Val Gln Gln Tyr Tyr Phe Asn Asn Gln Ile Gly
225                 230                 235                 240

Asn Pro Gly Met Lys Gln Leu Leu Ala Thr Tyr Thr Asp His Cys Val
                245                 250                 255

Arg Trp Tyr Asn Asn Gly Leu Thr Asn Arg Tyr Glu Thr Gly Gly Trp
            260                 265                 270

Asn Thr Phe Asn Asp Phe Arg Arg Asn Met Thr Leu Met Val Met Asp
        275                 280                 285

Val Val Ser Phe Trp Pro Thr Tyr Asp Pro Met Leu Tyr Lys Ile Pro
    290                 295                 300

Thr Lys Ser Gln Leu Thr Arg Ile Val Tyr Thr Pro Leu Ile Gly Arg
305                 310                 315                 320

Ala Asp Asp Phe Pro Gly Ile Pro Ala Pro Thr Ile Gly Glu Lys Glu
                325                 330                 335

Ser Thr Leu Thr Gln Pro Pro Arg Leu Phe Ala Trp Leu Arg Glu Leu
            340                 345                 350

Ser Ile Gly Glu Thr Thr Phe Pro Tyr Tyr Phe Ser Thr Gly Phe Cys
        355                 360                 365

Gly Arg Lys Gln Ile Phe Gln Asn Thr Met Asp Asn Asn Leu Trp Glu
    370                 375                 380

Glu Pro Tyr Lys Gly Ser Pro Gly Val Lys Asp Thr Gln Thr Leu Ile
385                 390                 395                 400

Ile Pro Ala Pro Glu Val Asn Asp Val Trp Arg Ile Val Thr Tyr
                405                 410                 415

Leu Lys Lys Met Ala Gly Ser Ile Gln Tyr Asp Glu Ile Met Gly Trp
            420                 425                 430

Asp Phe Ser Phe Thr Lys Ser Leu Asp Gln Arg Leu Tyr Arg Tyr His
        435                 440                 445
```

Leu Arg Ser Val Ser Ser Gly Met Pro Cys Gly Gly Ser Phe Pro Gly
            450                 455                 460

Pro Cys Asp Pro Cys Asn Ser Val Asp Pro Cys Ser Phe Glu Leu Pro
465                 470                 475                 480

Asn Pro Thr Ile Pro Cys Asp Asp Lys Ala Leu Tyr Ser His Arg Phe
                485                 490                 495

Ala Tyr Met Gly Ala Gly Phe Val Ser Asn Leu Ala Ala Met Thr Tyr
            500                 505                 510

Phe Ser Tyr Gly Trp Thr His Val Ser Ala Asp Ala Asn Asn Leu Ile
        515                 520                 525

Asp Ala Glu Arg Ile Thr Gln Ile Pro Ala Val Lys Gly Ser Glu Met
530                 535                 540

Glu Gly Thr Ala Lys Val Ile Gln Gly Pro Gly Ser Thr Gly Gly Asp
545                 550                 555                 560

Leu Val Gln Leu Asp Tyr Arg Gly Lys Ile Gln Ile Ser Met Thr Ala
                565                 570                 575

Pro Val Arg Lys Gly Tyr Gln Leu Arg Ile Arg Tyr Ala Thr Ala Ser
            580                 585                 590

Thr Ala Glu Ile His Val Ser Arg Val Ser Ile Arg Glu Asp Asp Ser
        595                 600                 605

Ser Asn Glu Asp Tyr Tyr His Phe Glu Phe Leu Pro Gln Thr Tyr Leu
    610                 615                 620

Ala Gly Ser Leu Asn Phe Asn Ser Phe Gly Tyr Thr Thr Met Ser Ile
625                 630                 635                 640

Pro Leu Pro Pro Gly Ala Gly Glu Gln Trp Asp Met Ser Phe Gln Trp
                645                 650                 655

Phe Gly Thr Asp Ser Pro Ile Ile Ile Asp Lys Ile Glu Phe Ile Pro
            660                 665                 670

Ile Glu

<210> SEQ ID NO 31
<211> LENGTH: 330
<212> TYPE: DNA
<213> ORGANISM: Bacillus thuringiensis

<400> SEQUENCE: 31
gtgaatgggt gcggccctat cggagtcaca ctcaatctct taaaagtggt gggatgtatt      60
ccctatatta caaatgcaac ggtagcaggg gaatgtggca gtaactgtga ttgcgattcg     120
aatgggaaac atcacattcg cgtgtgttgc tcgggcagta tttgcgtaga taatgtactg     180
aaatgtagta tcgaatgttt accacattac gagatgagtt gtcacaatgt tgttgtttca     240
gattttaaag tgacgccact acaagaacat ggctgtcata tgcttcaatt tacgggaacg     300
attgaattca agcacattcc ccatggcgaa                                       330

<210> SEQ ID NO 32
<211> LENGTH: 465
<212> TYPE: DNA
<213> ORGANISM: Bacillus thuringiensis

<400> SEQUENCE: 32
atgaatacaa aaattctatt ttgttttgca gtcaatatcc cacatggctt tgcgtatgtg      60
ccgaatggaa cacataaaat cgcatacaac ctggattgtc tatctggaat aaaagaaaag     120
tgcagaaaaa ccatccaagt agatggttgc ggtcctgtcg aagttacact aaatctctta     180
aaagtcttcg gctgtacacc ctatattaca atgcaacgg tagcaggtga atgtggtagt     240

```
aactttgatt gcgattcgca tgggaaacat cacagtagcg tgtgttgttc gggaagtatt    300
tacgcaaata atgtgctgaa atgtagtatt gaatgtttac cacattacga gatgaattgt    360
cacaatgtta ttgtttcgaa ttttaaaatg aagccactgc aagatcacgg ctttgagatg    420
ttgcagttta cagggacagt tgaatttaag cacattcctt atgaa                    465
```

<210> SEQ ID NO 33
<211> LENGTH: 675
<212> TYPE: DNA
<213> ORGANISM: Bacillus thuringiensis

<400> SEQUENCE: 33

```
atgaacaaaa aagacaaaag atttacatcc cttgtctttt tatatgtcct acactcagga    60
tatatcacaa atttacgcag acaggagggt tttgatttgg agagaaatga atcttttcga   120
gatgccatgt tcatcatga gcaagaatcg ctcaccatcc taccggaaga acctatacac    180
actgacacca aacaggtgtg cttcgaggag gtgaatacaa acatcccatt ttgttgtgca   240
gtcaatatcc cccatggctt tgcgtatgta ccgaatggaa cacataaaat cgcatacaat   300
ctggattgtg tatctgtcgt aaaagaaaca tgcagaaaaa ccattcaagt ggatgggtgc   360
ggtcctgtcg aagtcacact caatctctta aaagtggtgg gatgtattcc ctatattgtg   420
aatgcaacag tagtagggga atgcggcagg aactgtgatt gcgattcgaa tgggaaacat   480
cacattcagg tgtgttgttc aggaagtata tgcgtagata atgtgctgaa atgtagtatt   540
gaatgtttac cacattacga gatgaattgt cacaaggtgg ttgtttcaga tttgaaagtg   600
acgccactgc aagatcatgg ctgtcacatg cttcagttta caggaacgat tgagtttaaa   660
cacattccac atgca                                                    675
```

<210> SEQ ID NO 34
<211> LENGTH: 110
<212> TYPE: PRT
<213> ORGANISM: Bacillus thuringiensis

<400> SEQUENCE: 34

```
Val Asn Gly Cys Gly Pro Ile Gly Val Thr Leu Asn Leu Leu Lys Val
1               5                   10                  15

Val Gly Cys Ile Pro Tyr Ile Thr Asn Ala Thr Val Ala Gly Glu Cys
            20                  25                  30

Gly Ser Asn Cys Asp Cys Asp Ser Asn Gly Lys His His Ile Arg Val
        35                  40                  45

Cys Cys Ser Gly Ser Ile Cys Val Asp Asn Val Leu Lys Cys Ser Ile
    50                  55                  60

Glu Cys Leu Pro His Tyr Glu Met Ser Cys His Asn Val Val Val Ser
65                  70                  75                  80

Asp Phe Lys Val Thr Pro Leu Gln Glu His Gly Cys His Met Leu Gln
                85                  90                  95

Phe Thr Gly Thr Ile Glu Phe Lys His Ile Pro His Gly Glu
            100                 105                 110
```

<210> SEQ ID NO 35
<211> LENGTH: 155
<212> TYPE: PRT
<213> ORGANISM: Bacillus thuringiensis

<400> SEQUENCE: 35

```
Met Asn Thr Lys Ile Leu Phe Cys Phe Ala Val Asn Ile Pro His Gly
1               5                   10                  15
```

```
Phe Ala Tyr Val Pro Asn Gly Thr His Lys Ile Ala Tyr Asn Leu Asp
            20                  25                  30

Cys Leu Ser Gly Ile Lys Glu Lys Cys Arg Lys Thr Ile Gln Val Asp
        35                  40                  45

Gly Cys Gly Pro Val Glu Val Thr Leu Asn Leu Leu Lys Val Phe Gly
    50                  55                  60

Cys Thr Pro Tyr Ile Thr Asn Ala Thr Val Ala Gly Glu Cys Gly Ser
65                  70                  75                  80

Asn Phe Asp Cys Asp Ser His Gly Lys His His Ser Ser Val Cys Cys
                85                  90                  95

Ser Gly Ser Ile Tyr Ala Asn Asn Val Leu Lys Cys Ser Ile Glu Cys
            100                 105                 110

Leu Pro His Tyr Glu Met Asn Cys His Asn Val Ile Val Ser Asn Phe
        115                 120                 125

Lys Met Lys Pro Leu Gln Asp His Gly Phe Glu Met Leu Gln Phe Thr
    130                 135                 140

Gly Thr Val Glu Phe Lys His Ile Pro Tyr Glu
145                 150                 155
```

<210> SEQ ID NO 36
<211> LENGTH: 225
<212> TYPE: PRT
<213> ORGANISM: Bacillus thuringiensis

<400> SEQUENCE: 36

```
Met Asn Lys Lys Asp Lys Arg Phe Thr Ser Leu Val Phe Leu Tyr Val
 1               5                  10                  15

Leu His Ser Gly Tyr Ile Thr Asn Leu Arg Arg Gln Glu Gly Phe Asp
            20                  25                  30

Leu Glu Arg Asn Glu Ser Phe Arg Asp Ala Met Phe His His Glu Gln
        35                  40                  45

Glu Ser Leu Thr Ile Leu Pro Glu Glu Pro Ile His Thr Asp Thr Lys
    50                  55                  60

Gln Val Cys Phe Glu Glu Val Asn Thr Asn Ile Pro Phe Cys Cys Ala
65                  70                  75                  80

Val Asn Ile Pro His Gly Phe Ala Tyr Val Pro Asn Gly Thr His Lys
                85                  90                  95

Ile Ala Tyr Asn Leu Asp Cys Val Ser Val Val Lys Glu Thr Cys Arg
            100                 105                 110

Lys Thr Ile Gln Val Asp Gly Cys Gly Pro Val Glu Val Thr Leu Asn
        115                 120                 125

Leu Leu Lys Val Val Gly Cys Ile Pro Tyr Ile Val Asn Ala Thr Val
    130                 135                 140

Val Gly Glu Cys Gly Arg Asn Cys Asp Cys Asp Ser Asn Gly Lys His
145                 150                 155                 160

His Ile Gln Val Cys Cys Ser Gly Ser Ile Cys Val Asp Asn Val Leu
                165                 170                 175

Lys Cys Ser Ile Glu Cys Leu Pro His Tyr Glu Met Asn Cys His Lys
            180                 185                 190

Val Val Val Ser Asp Leu Lys Val Thr Pro Leu Gln Asp His Gly Cys
        195                 200                 205

His Met Leu Gln Phe Thr Gly Thr Ile Glu Phe Lys His Ile Pro His
    210                 215                 220

Ala
225
```

```
<210> SEQ ID NO 37
<211> LENGTH: 4
<212> TYPE: PRT
<213> ORGANISM: Artificial Sequence
<220> FEATURE:
<223> OTHER INFORMATION: endoplasmic reticulum targeting peptide

<400> SEQUENCE: 37

Lys Asp Glu Leu
  1
```

AXMI218, AXMI219, AXMI220, AXMI226, AXMI227, AXMI228, AXMI229, AXMI230, AND AXMI231, DELTA-ENDOTOXIN GENES AND METHODS FOR THEIR USE

CROSS REFERENCE TO RELATED APPLICATION

This application claims the benefit of U.S. Provisional Application Ser. No. 61/305,808, filed Feb. 18, 2010, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA068US01SEQLIST.txt", created on Jan. 10, 2011, and having a size of 199 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Hemipteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer, and the improvement in yield by controlling insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules are provided that encode a pesticidal protein. Additionally, amino acid sequences corresponding to the pesticidal protein are encompassed. In particular, the present invention provides for an isolated nucleic acid molecule comprising a nucleotide sequence encoding the amino acid sequence shown in SEQ ID NO:21-32 or a nucleotide sequence set forth in SEQ ID NO:1-5, as well as variants and fragments thereof. Nucleotide sequences that are complementary to a nucleotide sequence of the invention, or that hybridize to a sequence of the invention are also encompassed. Synthetic nucleotide sequences encoding the polypeptides disclosed herein are also set forth in SEQ ID NO:6-20.

Methods are provided for producing the polypeptides of the invention, and for using those polypeptides for controlling or killing a lepidopteran, hemipteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling, for example, with members of the Cry1, Cry2, and Cry9 families of endotoxins. The proteins find use in controlling or killing lepidopteran, hemipteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, and Coleoptera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Pesticidal proteins encompass delta-endotoxins. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," on the worldwide web at biols.susx.ac.uk/Home/Neil_Crickmore/Bt/index.

Thus, provided herein are novel isolated nucleotide sequences that confer pesticidal activity. These isolated nucleotide sequences encode polypeptides with homology to known delta-endotoxins or binary toxins. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "recombinant" nucleic acid sequence (or DNA) is used herein to refer to a nucleic acid sequence (or DNA) that is no longer in its natural environment, for example in an in vitro or in a recombinant bacterial or plant host cell. In some embodiments, an isolated or recombinant nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1-20, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the pesticidal protein encoded by this nucleotide sequence are set forth in SEQ ID NO:21-32.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. In another embodiment, the pesticidal activity is hemiptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to SEQ ID NO:21-32. In some embodiments, the fragments encompassed herein result from the removal of the C-terminal crystallization domain, e.g., by proteolysis or by insertion of a stop codon in the coding sequence. See, for example, the truncated amino acid sequences set forth in SEQ ID NO:22, 23, 25, 26, and 32. It will be understood that the truncation site may vary by 1, 2, 3, 4, 5, 6, 7, 8, 9, 10, 11, 12, 13, 14, 15, or more amino acids on either side of the truncation site represented by the terminus of SEQ ID NO:22, 23, 25, 26, and 32 (compared to the corresponding full-length sequence).

Preferred pesticidal proteins of the present invention are encoded by a nucleotide sequence sufficiently identical to the nucleotide sequence of SEQ ID NO:1-20. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1-20). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10. The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal protein sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in SEQ ID NO:21-32. Fragments, biologically active portions, and variants thereof are also provided, and may be used to practice the methods of the present invention. An "isolated protein" is used to refer to a protein that is no longer in its natural environment, for example in vitro or in a recombinant bacterial or plant host cell. An "isolated protein" or a "recombinant protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in SEQ ID NO:21-32, and that exhibit pesticidal activity. A biologically active portion of a pesticidal protein can be a polypeptide that is, for example, 10, 25, 50, 100, 150, 200, 250 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:21-32. The invention encompasses other fragments, however, such as any fragment in the protein greater than about 10, 20, 30, 50, 100, 150, 200, 250, or 300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:21-32. Variants also include polypeptides encoded by a nucleic acid molecule that hybridizes to the nucleic acid molecule of SEQ ID NO:1-20, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. See, for example, the alternate start site for the AXMI223z protein set forth in SEQ ID NO: 28 and the alternate start site for AXMI224z protein set forth in SEQ ID NO:30. These pesticidal proteins are encompassed in the present invention and may be used in the methods of the present invention. It will be understood that, when expressed in plants, it will be necessary to alter the alternate start codon to ATG for proper translation.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:21-32, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265: 20923-20930; Rang et al. 91999) *Appl. Environ. Microbiol.* 65:2918-2925).

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196: 1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In various embodiments, the transgenic plant further comprises one or more additional genes for insect resistance (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families; etc.). It will be understood by one of skill in the art that the transgenic plant may comprise any gene imparting an agronomic trait of interest.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual. Cold Spring Harbor Laboratory Press*, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, *macadamia*, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Pesticidal Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, hemipteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylimidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachimidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2, 2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2 (5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran, Organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino] furan-2(5H)-on.

The following examples are offered by way of illustration and not by way of limitation.

EXPERIMENTAL EXAMPLES

Example 1

Discovery of Novel Pesticidal Genes from *Bacillus thuringiensis*

Novel pesticidal genes were identified from the bacterial strains listed in Table 1 using the following steps:
Preparation of extrachromosomal DNA from the strain. Extrachromosomal DNA contains a mixture of some or all of the following: plasmids of various size; phage chromosomes; genomic DNA fragments not separated by the purification protocol; other uncharacterized extrachromosomal molecules.
Mechanical or enzymatic shearing of the extrachromosomal DNA to generate size-distributed fragments.
Sequencing of the fragmented DNA by high-throughput pyrosequencing methods.
Identification of putative toxin genes via homology and/or other computational analyses.
When required, sequence finishing of the gene of interest by one of several PCR or cloning strategies (e.g. TAIL-PCR).

TABLE 1

Novel genes identified from *Bacillus thuringiensis*

| Gene name | Molecular weight (kD) | Strain | Closest homolog (trun = truncated version) | Nucleotide SEQ ID NO | Amino acid SEQ ID NO |
|---|---|---|---|---|---|
| Axmi218 | 130 | ATX2012 | 44.3% Axmi020<br>44.0% Axmi018<br>24.6% Axmi040 (trun)<br>24.2% Cry12Aa (trun) | 1 | 13<br>14 (trun) |
| Axmi219 | 139.3 | ATX2012 | 31.1% Cry21Ba<br>39.2% Cry21Aa (trun) | 2 | 15<br>16 (trun) |
| Axmi220 | 141.6 | ATX2012 | 61.4% Axmi219<br>36.7% Axmi018<br>66.5% Axmi219 (trun)<br>40.8% Cry21Aa (trun) | 3 | 17<br>18 (trun) |
| Axmi226 | 146.6 | ATX29611 | 66.3% Axmi102<br>64.7% Axmi166<br>63.5% Axmi093<br>57.6% Axmi102 (trun)<br>57.2% Axmi082 (trun)<br>56.1% Axmi166 (trun) | 4 | 19<br>20 (trun) |
| Axmi227 | 148.7 | ATX13039 | 57.3% Axmi169<br>40.2% Axmi155<br>76.2% Axmi169 (trun)<br>39.9% Axmi155 (trun) | 5 | 21<br>22 (trun) |
| Axmi228 | 145.5 | ATX29611 | 92.8% Axmi175<br>56.9% Axmi057<br>90.3% Axmi175 (trun)<br>59.3% Axmi080 (trun) | 6 | 23<br>24 (trun) |
| Axmi229 | 139.1 | ATX29611 | 54.2% Axmi093<br>53.7% Axmi057<br>46.1% Axmi111 (trun)<br>40.5% Cry41Aa (trun) | 7 | 25<br>26 (trun) |
| Axmi230 | 147.4 | ATX29611 | 59.9% Axmi173<br>59.1% Axmi226<br>59.0% Axmi165<br>45.6% Axmi173 (trun)<br>44.6% Axmi079 (trun)<br>43.6% Axmi165 (trun) | 8 | 27<br>28 (trun) |
| Axmi231 | 161 | ATX29611 | 60.3% Axmi082<br>56.8% Axmi102<br>49.7% Axmi165 (trun)<br>49.3% Axmi067 (trun) | 9 | 29<br>30 (trun) |

The toxin gene disclosed herein is amplified by PCR from pAX980, and the PCR product is cloned into the *Bacillus* expression vector pAX916, or another suitable vector, by methods well known in the art. The resulting *Bacillus* strain, containing the vector with axmi gene is cultured on a conventional growth media, such as CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared and tested for activity in bioassays.

Two additional genes were identified upstream of the Axmi229, Axmi230, and Axmi231 coding regions. The nucleotide sequence upstream of the Axmi229 sequence is set forth in SEQ ID NO:31 and the encoded amino acid sequence is set forth in SEQ ID NO:34. The nucleotide sequence upstream of the Axmi230 sequence is set forth in SEQ ID NO:32 and the encoded amino acid sequence is set forth in SEQ ID NO:35. The nucleotide sequence upstream of the Axmi231 sequence is set forth in SEQ ID NO:33 and the encoded amino acid sequence is set forth in SEQ ID NO:36.

Example 2

Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests* and *Journal of Economic Entomology* or by discussion with members of the Entomological Society of America (ESA).

In some embodiments, the DNA regions encoding the toxin domains of delta-endotoxins disclosed herein are cloned into the *E. coli* expression vector pMAL-C4x behind the malE gene coding for Maltose binding protein (MBP). These in-frame fusions result in MBP-Axmi fusion proteins expression in *E. coli*.

For expression in *E. coli*, BL21*DE3 are transformed with individual plasmids. Single colonies are inoculated in LB supplemented with carbenicillin and glucose, and grown overnight at 37° C. The following day, fresh medium is inoculated with 1% of overnight culture and grown at 37° C. to logarithmic phase. Subsequently, cultures are induced with 0.3 mM IPTG overnight at 20° C. Each cell pellet is suspended in 20 mM Tris-Cl buffer, pH 7.4+200 mM NaCl+1 mM DTT+protease inhibitors and sonicated. Analysis by SDS-PAGE can be used to confirm expression of the fusion proteins.

Total cell free extracts are then run over amylose column attached to fast protein liquid chromatography (FPLC) for affinity purification of MBP-axmi fusion proteins. Bound fusion proteins are eluted from the resin with 10 mM maltose solution. Purified fusion proteins are then cleaved with either Factor Xa or trypsin to remove the amino terminal MBP tag from the Axmi protein. Cleavage and solubility of the proteins can be determined by SDS-PAGE.

Example 3

Activity of Protein Expressed from Axmi genes in Bioassays

Full-length and truncated versions of some genes were cloned into vector pRSF-1b as shown in Table 2. By virtue of cloning into this vector, the resulting expressed protein contains an additional six N-terminal histidine residues.

Other genes were cloned into an *E. coli* expression vector pMAL-C4x behind the malE gene coding for Maltose binding protein (MBP) as shown in Table 2. These in-frame fusions resulted in MBP-AXMI fusion proteins expression in *E. coli*. Total cell free extracts were loaded onto an FPLC equipped with an amylose column, and the MBP-AXMI fusion proteins were purified by affinity chromatography. Bound fusion protein was eluted from the resin with 10 mM maltose solution. Purified fusion proteins were then cleaved with either Factor Xa or trypsin to remove the amino terminal MBP tag from the AXMIz protein. Cleavage and solubility of the proteins was determined by SDS-PAGE. Each of the proteins produced from the constructs above were tested in bioassays as a 10× concentrated pellet.

TABLE 2

Axmi constructs

| gene | construct name | backbone vector | SEQ ID NO: of protein encoded by construct |
| --- | --- | --- | --- |
| Axmi218 (truncated) | pAX5074 | pMAL | 14 |
| Axmi218 (truncated) | pAX7603 | pRSF1b | 14 |
| Axmi218 (truncated) | pAX7619 | pAX916 | 14 |
| Axmi218 (truncated) | pAX7619 | pAX916 | 14 |
| Axmi220 (full length) | pAX7628 | pRSF1b | 17 |
| Axmi220 (full length) | pAX7628 | pRSF1b | 17 |
| Axmi220 (truncated) | pAX7621 | pAX916 | 18 |
| Axmi220 (truncated) | pAX7605 | pRSF1b | 18 |
| Axmi220 (truncated) | pAX7605 | pRSF1b | 18 |
| Axmi220 (truncated) | pAX7605 | pRSF1b | 18 |

Bioassay of the expressed Axmiz genes resulted in observance of the insect activities shown in Table 3:

TABLE 3

| Bioassay results | | | | | | |
|---|---|---|---|---|---|---|
| Construct | Gene | BCW* | DBM* | FAW* | SCRW* | WCRW* |
| pAx5074 | Axmi218 (trun) | | 1, 0% | | | |
| pAx7603 | Axmi218 (trun) | 1, 0% | | | | |
| pAX7619 | Axmi218 (trun) | | | | 1, 0% | 1, 0% |
| pAx7605 | Axmi220 (trun) | 1, 0% | 1, 0% | 1, 0% | | |
| pAx7628 | Axmi220 | | 4, 100% | 1, 0% | | |
| pAX7621 | Axmi220 (trun) | | | | 1, 0% | |

BCW: Black cutworm
DBM: Diamondback Moth
FAW: Fall armyworm
SCRW: Southern corn rootworm
WCRW: Western corn rootworm
*= represented as stunt and mortality percent where stunting is scored according to the scale in Table 4:

TABLE 4

| Stunting Score | |
|---|---|
| Score | Definition |
| 0 | No Activity |
| 1 | Slight, non-uniform stunt |
| 2 | Non-uniform stunt |
| 3 | Uniform stunt |
| 4 | Uniform stunt with mortality (expressed as a percentage) |
| 5 | Uniform stunt with 100% mortality |

Example 4

Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

In one aspect of the invention, synthetic DNA sequences are designed and generated. These synthetic sequences have altered nucleotide sequence relative to the parent sequence, but encode proteins that are essentially identical to the parent sequence (e.g., SEQ ID NO:1-9). See, for example, the synthetic nucleotide sequences set forth in SEQ ID NO:10-12.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:37) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 5

Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

TABLE 5

| DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 6

Transformation of genes of the invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant nucleic acid molecule comprising a nucleotide sequence encoding an amino acid sequence having pesticidal activity against a lepidopteran pest, wherein said nucleotide sequence is selected from the group consisting of:
   a) the nucleotide sequence set forth in SEQ ID NO: 3; and
   b) a nucleotide sequence that encodes a polypeptide comprising the amino acid sequence of SEQ ID NO: 17 or 18,
   wherein said nucleotide sequence encoding an amino acid sequence having pesticidal activity is operably linked to a heterologous promoter.

2. The recombinant nucleic acid molecule of claim 1, wherein said nucleotide sequence is a synthetic sequence that has been designed for expression in a plant.

3. The recombinant nucleic acid molecule of claim 1, wherein said heterologous promoter is capable of directing expression of said nucleotide in a plant cell.

4. A vector comprising the recombinant nucleic acid molecule of claim 1.

5. The vector of claim 4, further comprising a nucleic acid molecule encoding a heterologous polypeptide.

6. A host cell that contains the vector of claim 4.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the nucleic acid molecule of claim 1.

12. A recombinant polypeptide with pesticidal activity against a lepidopteran pest, selected from the group consisting of: a polypeptide comprising the amino acid sequence of SEQ ID NO: 17 and 18.

13. The polypeptide of claim 12 further comprising a leader sequence, a signal sequence, or a transit peptide.

14. A composition comprising the polypeptide of claim 12.

15. The composition of claim 14, wherein said composition is selected from the group consisting of a powder, dust, pellet, granule, spray, emulsion, colloid, and solution.

16. The composition of claim 14, wherein said composition is prepared by desiccation, lyophilization, homogenization, extraction, filtration, centrifugation, sedimentation, or concentration of a culture of bacterial cells.

17. The composition of claim 14, comprising from 1% to 99% by weight of said polypeptide.

18. A method for controlling a lepidopteran pest population comprising contacting said population with a pesticidally-effective amount of a polypeptide of claim 12.

19. A method for killing a lepidopteran pest with, or feeding to said pest, a pesticidally-effective amount of a polypeptide of claim 12.

20. A method for producing a polypeptide with pesticidal activity against a lepidopteran pest, comprising culturing the host cell of claim 6 under conditions in which the nucleic acid molecule encoding the polypeptide is expressed.

21. A plant having stably incorporated into its genome a DNA construct comprising a nucleotide sequence that encodes a protein having pesticidal activity against a lepidopteran pest, wherein said nucleotide sequence is selected from the group consisting of:
   a) the nucleotide sequence set forth in SEQ ID NO: 3; and
   b) a nucleotide sequence that encodes a polypeptide comprising the amino acid sequence of SEQ ID NO: 17 or 18.

22. The plant of claim 21, wherein said plant is a plant cell.

23. A method for protecting a plant from a pest, comprising expressing in a plant or cell thereof a nucleotide sequence that encodes a pesticidal polypeptide, wherein said polypeptide has pesticidal activity against a lepidopteran pest, and wherein said nucleotide sequence is selected form the group consisting of:
   a) the nucleotide sequence set forth in SEQ ID NO: 3; and
   b) a nucleotide sequence that encodes a polypeptide comprising the amino acid sequence of SEQ ID NO: 17 or 18.

24. The method of claim 23, wherein said plant produces a pesticidal polypeptide having pesticidal activity against a lepidopteran.

25. A method for increasing yield in a plant comprising growing in a field a plant or a seed thereof having stably incorporated into its genome a DNA construct comprising a nucleotide sequence that encodes a protein having pesticidal activity against a lepidopteran pest, wherein said nucleotide sequence is selected form the group consisting of:
   a) the nucleotide sequence set forth in SEQ ID NO: 3; and
   b) a nucleotide sequence that encodes a polypeptide comprising the amino acid sequence of SEQ ID NO: 17 or 18;
   wherein said field is infested with a pest against which said polypeptide has pesticidal activity.

* * * * *